US012686849B2

(12) United States Patent
Easley, IV et al.

(10) Patent No.: US 12,686,849 B2
(45) Date of Patent: *Jul. 21, 2026

(54) COMPOSITIONS AND METHODS FOR IMPROVING EMBRYO DEVELOPMENT

(71) Applicants: University of Georgia Research Foundation, Inc., Athens, GA (US); Emory University, Atlanta, GA (US)

(72) Inventors: Charles A. Easley, IV, Athens, GA (US); Anthony W.S. Chan, Atlanta, GA (US)

(73) Assignees: University of Georgia Research Foundation, Inc., Athens, GA (US); Emory University, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/440,821

(22) Filed: Feb. 13, 2024

(65) Prior Publication Data

US 2024/0301349 A1 Sep. 12, 2024

Related U.S. Application Data

(63) Continuation of application No. 17/265,157, filed as application No. PCT/US2019/044589 on Aug. 1, 2019, now Pat. No. 11,939,593.

(60) Provisional application No. 62/713,182, filed on Aug. 1, 2018.

(51) Int. Cl.
| | |
|---|---|
| *C12N 5/073* | (2010.01) |
| *C12N 5/076* | (2010.01) |
| *C12N 15/90* | (2006.01) |

(52) U.S. Cl.
CPC ........... *C12N 5/0604* (2013.01); *C12N 5/061* (2013.01); *C12N 15/90* (2013.01); *C12N 2506/02* (2013.01); *C12N 2506/45* (2013.01); *C12N 2510/00* (2013.01); *C12N 2517/10* (2013.01)

(58) Field of Classification Search
None
See application file for complete search history.

(56) References Cited

U.S. PATENT DOCUMENTS

| | | | |
|---|---|---|---|
| 5,034,506 | A | 7/1991 | Summerton et al. |
| 5,142,047 | A | 8/1992 | Summerton et al. |
| 5,166,315 | A | 11/1992 | Summerton et al. |
| 5,217,866 | A | 6/1993 | Summerton et al. |
| 5,356,802 | A | 10/1994 | Chandrasegaran |
| 5,436,150 | A | 7/1995 | Chandrasegaran |
| 5,487,994 | A | 1/1996 | Chandrasegaran |
| 5,506,337 | A | 4/1996 | Summerton et al. |
| 5,521,063 | A | 5/1996 | Summerton et al. |
| 5,527,675 | A | 6/1996 | Coull et al. |
| 5,539,082 | A | 7/1996 | Nielsen et al. |
| 5,623,049 | A | 4/1997 | Loebberding et al. |
| 5,698,685 | A | 12/1997 | Summerton et al. |
| 5,714,331 | A | 2/1998 | Buchardt et al. |
| 5,736,336 | A | 4/1998 | Buchardt et al. |
| 5,773,571 | A | 6/1998 | Nielsen et al. |
| 5,786,571 | A | 7/1998 | Bethel et al. |
| 6,140,081 | A | 10/2000 | Barbas |
| 6,453,242 | B1 | 9/2002 | Eisenberg et al. |
| 6,534,261 | B1 | 3/2003 | Cox et al. |
| 6,610,512 | B1 | 8/2003 | Barbas |
| 6,746,838 | B1 | 6/2004 | Choo et al. |
| 6,866,997 | B1 | 3/2005 | Choo et al. |
| 7,067,617 | B2 | 6/2006 | Barbas et al. |
| 2002/0165356 | A1 | 11/2002 | Barbas et al. |
| 2004/0197892 | A1 | 10/2004 | Moore et al. |
| 2007/0154989 | A1 | 7/2007 | Barbas |
| 2007/0213269 | A1 | 9/2007 | Barbas et al. |

(Continued)

FOREIGN PATENT DOCUMENTS

| | | |
|---|---|---|
| EP | 0502976 B1 | 7/1996 |
| WO | 9853059 A1 | 11/1998 |

(Continued)

OTHER PUBLICATIONS

Maria-Teresa Paramio, Dolors Izquierdo. Assisted reproduction technologies in goats. Small Ruminant Research (2014) 121, 1:21-26. (Year: 2014).*

(Continued)

*Primary Examiner* — Christopher M Babic
*Assistant Examiner* — Alyssa G Weston
(74) *Attorney, Agent, or Firm* — PABST PATENT GROUP LLP

(57) ABSTRACT

Compositions and methods for improving embryo development, treating idiopathic male factor infertility, and enabling infertile/sub-fertile/sterile men to father their own genetic offspring are provided. Typically, the methods include administering into a male or female gamete or fertilized embryo an effective amount of a compound that increases bioavailability of a TET protein to improve development of an embryo resulting from fertilization of the female gamete by a male gamete. The compound can be administered into the gamete or embryo before, during, or after fertilization. The compound can be administered by an injection such as intracytoplasmic injection. The compound and the male gamete can be administered in combination by intracytoplasmic sperm injection. Methods of making male gametes, and methods of modifying the genome of a male gamete or embryo using an effective amount of a gene editing composition to correct a gene mutation or anomaly in the genome thereof are also provided.

20 Claims, 14 Drawing Sheets

Specification includes a Sequence Listing.

(56) References Cited

U.S. PATENT DOCUMENTS

| | | | |
|---|---|---|---|
| 2011/0145940 A1 | 6/2011 | Voytas et al. | |
| 2011/0236894 A1 | 9/2011 | Rao et al. | |
| 2016/0186207 A1 | 6/2016 | Reik et al. | |
| 2021/0340493 A1 | 11/2021 | Easley et al. | |

FOREIGN PATENT DOCUMENTS

| | | | | |
|---|---|---|---|---|
| WO | 03016496 A2 | 2/2003 | | |
| WO | 2010037001 A2 | 4/2010 | | |
| WO | 2011072246 A2 | 6/2011 | | |
| WO | WO-2012029957 A1 * | 3/2012 | ......... | A01K 67/0273 |
| WO | 2013176772 A1 | 11/2013 | | |
| WO | 2014018423 A2 | 1/2014 | | |
| WO | 2014096800 A1 | 6/2014 | | |

OTHER PUBLICATIONS

Bahadur, G, Fertility issues for cancer patients, Mol Cell Endocrinol., vol. 169, No. 1-2, Nov. 27, 2000, pp. 117-122.

Boettcher, et al., Choosing the Right Tool for the Job: RNAi, TALEN, or CRISPR, Mol Cell., vol. 58, No. 4, May 21, 2015, pp. 575-585.

Braasch, et al., Locked nucleic acid (LNA): fine-tuning the recognition of DNA and RNA, Chem. Biol., vol. 8, No. 1, 2001, pp. 1-7.

Byrne, et al., Producing primate embryonic stem cells by somatic cell nuclear transfer, Nature., vol. 450, No. 7169, Nov. 22, 2007, pp. 497-502.

Carillo, et al., The Multiple Sequence Alignment Problem in Biology, SIAM J Applied Math., vol. 48, No. 5, Oct. 1988, pp. 1073-1082.

Cermak, et al., Efficient design and assembly of custom TALEN and other TAL effector-based constructs for DNA targeting, Nucleic Acids Res., vol. 39, No. 12: e82, Jul. 2011.

Chang, et al., Assisted reproductive technology in nonhuman primates, Methods Mol Biol., vol. 770, 2011, pp. 337-363.

Chang, et al., Modification of DNA ends can decrease end joining relative to homologous recombination in mammalian cells, Proc Natl Acad Sci U S A., vol. 84, No. 14, Jul. 1987, pp. 4959-4963.

Chitwood, et al., Transcriptome profiling of individual rhesus macaque oocytes and preimplantation embryos, Biol Reprod., vol. 97, No. 3, Sep. 1, 2017, pp. 353-364.

Cong, et al., Multiplex Genome Engineering using CRISPR/Cas Systems, Science, vol. 339, No. 6121, Feb. 2013, pp. 819-823.

Dawlaty, et al., Combined deficiency of Tet1 and Tet2 causes epigenetic abnormalities but is compatible with postnatal development, Dev Cell., vol. 24, No. 3, Feb. 11, 2013, pp. 310-323.

Deutsch, et al., Sirolimus-associated infertility: case report and literature review of possible mechanisms, Am J Transplant., vol. 7, No. 10, Oct. 2007, pp. 2414-2421.

Duan, et al., The dynamic changes of DNA methylation in primordial germ cell differentiation, Gene., vol. 591, No. 2, Oct. 15, 2016, pp. 305-312.

Easley, IV, et al., Assessing reproductive toxicity of two environmental toxicants with a novel in vitro human spermatogenic model, Stem Cell Res., vol. 14, No. 3, May 2015, pp. 347-355.

Easley, IV, et al., Direct differentiation of human pluripotent stem cells into haploid spermatogenic cells, Cell Rep., vol. 2, No. 3, Sep. 27, 2012, pp. 440-446.

Easley, IV, et al., Using Pluripotent Stem Cells to Treat Male-factor Infertility: Towards a Potential Regenerative Medicine Strategy, RBC Poster, Mar. 8, 2018.

Ehmcke, et al., Spermatogonial stem cells: questions, models and perspectives, Hum Reprod Update., vol. 12, No. 3, 2006, pp. 275-282.

Fayomi, et al., Spermatogonial stem cells and spermatogenesis in mice, monkeys and men, Stem Cell Res., vol. 29, May 2018, pp. 207-214.

Fujimoto, et al., Aberrant genomic imprinting in rhesus monkey embryonic stem cells, Stem Cells., vol. 24, No. 3, Mar. 2006, pp. 595-603.

Fujimoto, et al., Development of a monkey model for the study of primate genomic imprinting, Mol Hum Reprod., vol. 11, No. 6, Jun. 2005, pp. 413-422.

Gao, et al., De novo DNA methylation during monkey pre-implantation embryogenesis, Cell Res., vol. 27, No. 4, Apr. 2017, pp. 526-539.

Gassei, et al., Experimental methods to preserve male fertility and treat male factor infertility, Fertil Steril., vol. 105, No. 2, Feb. 2016, pp. 256-266.

Gu, et al., The role of Tet3 DNA dioxygenase in epigenetic reprogramming by oocytes, Nature., vol. 477, No. 7366, Sep. 4, 2011, pp. 606-610.

Guo, et al., Active and passive demethylation of male and female pronuclear DNA in the mammalian zygote, Cell Stem Cell., vol. 15, No. 4, Oct. 2, 2014, pp. 447-459.

Han, et al., Overexpression of Tet3 in donor cells enhances goat somatic cell nuclear transfer efficiency, FEBS J., vol. 285, No. 14, Jul. 2018, pp. 2708-2723.

Handel, et al., Applying "gold standards" to in-vitro-derived germ cells, Cell., vol. 157, No. 6, Jun. 5, 2014, pp. 1257-1261.

Hayashi, et al., Reconstitution of the mouse germ cell specification pathway in culture by pluripotent stem cells, Cell., vol. 146, No. 4, Aug. 19, 2011, pp. 519-532.

International Search Report received for PCT Patent Application No. PCT/US2019/044589, mailed on Dec. 17, 2019, 6 pages.

Jinek, et al., A Programmable Dual-RNA-Guided DNA Endonuclease in Adaptive Bacterial Immunity, Science, vol. 337, No. 6096, Aug. 2012, pp. 816-821.

Kee, et al., Human DAZL, DAZ and BOULE genes modulate primordial germ-cell and haploid gamete formation, Nature., vol. 462, No. 7270, Nov. 12, 2009, pp. 222-225.

Kim, et al., Chimeric restriction endonuclease, Proc Natl Acad Sci U S A., vol. 91, No. 3, Feb. 1, 1994, pp. 883-887.

Kim, et al., Insertion and deletion mutants of FokI restriction endonuclease, J Biol Chem., vol. 269, No. 50, Dec. 16, 1994, pp. 31978-31982.

Levine, et al., Temporal trends in sperm count: a systematic review and meta-regression analysis, Hum Reprod Update., vol. 23, No. 6, Nov. 1, 2017, pp. 646-659.

Li, et al., Alteration of the cleavage distance of Fok I restriction endonuclease by insertion mutagenesis, Proc Natl Acad Sci U S A., vol. 90, No. 7, Apr. 1, 1993, pp. 2764-2768.

Li, et al., Functional domains in Fok I restriction endonuclease, Proc Natl Acad Sci U S A., vol. 89, No. 10, May 15, 1992, pp. 4275-4279.

Liu, Lin, Linking Telomere Regulation to Stem Cell Pluripotency, Trends Genet., vol. 33, No. 1, Jan. 2017, pp. 16-33.

Long, et al., ZF-CxxC domain-containing proteins, CpG islands and the chromatin connection, Biochem Soc Trans., vol. 41, No. 3, Jun. 2013, pp. 727-740.

Louis, et al., The prevalence of couple infertility in the United States from a male perspective: evidence from a nationally representative sample, Andrology., vol. 1, No. 5, Sep. 2013, pp. 741-748.

Meng, et al., Sperm-induced oocyte activation in the rhesus monkey: nuclear and cytoplasmic changes following intracytoplasmic sperm injection, Hum Reprod., vol. 12, No. 5, May 1997, pp. 1062-1068.

Messerschmidt, et al., DNA methylation dynamics during epigenetic reprogramming in the germline and preimplantation embryos, Genes Dev., vol. 28, No. 8, Apr. 15, 2014, pp. 812-828.

Miller, et al., A TALE nuclease architecture for efficient genome editing, Nat Biotechnol., vol. 29, No. 2, Feb. 2011, pp. 143-148.

Nakamura, et al., Codon usage tabulated from international DNA sequence databases: status for the year 2000, Nucleic Acids Res, vol. 28, No. 1, Jan. 1, 2000, p. 292.

Navara, et al., Pedigreed primate embryonic stem cells express homogeneous familial gene profiles, Stem Cells., vol. 25, No. 11, Nov. 2011, pp. 2695-2704.

Navara, et al., The sperm centrosome during fertilization in mammals: implications for fertility and reproduction, Reprod Fertil Dev., vol. 7, No. 4, 1995, pp. 747-754.

(56) References Cited

OTHER PUBLICATIONS

Needleman, et al., A General Method Applicable to the Search for Similarities in the Amino Acid Sequence of Two Proteins, J. Mol. Biol., vol. 48, No. 3, Mar. 1970, pp. 443-453.

Nehls, et al., Two genetically separable steps in the differentiation of thymic epithelium, Science., vol. 272, No. 5263, May 10, 1996, pp. 886-889.

Ni, et al., TET enzymes are successively expressed during human spermatogenesis and their expression level is pivotal for male fertility, Hum Reprod., vol. 31, No. 7, Jul. 2016, pp. 1411-1124.

Panula, et al., Human germ cell differentiation from fetal- and adult-derived induced pluripotent stem cells, Hum Mol Genet., vol. 20, No. 4, Feb. 15, 2011, pp. 752-762.

Raab, et al., A Comparative View on Human Somatic Cell Sources for iPSC Generation, Stem Cells Int., vol. 768391, 2014.

Rasmussen, et al., Role of TET enzymes in DNA methylation, development, and cancer, Genes Dev., vol. 30, No. 7, Apr. 1, 2016, pp. 733-750.

Schatten, et al., LEGOs® and legacies of centrioles and centrosomes, EMBO Rep., vol. 16, No. 9, Sep. 2015, pp. 1052-1054.

Schlegel, P N., Evaluation of male infertility, Minerva Ginecol., vol. 61, No. 4, Aug. 2009, pp. 261-283.

Shen, et al., Tet3 and DNA replication mediate demethylation of both the maternal and paternal genomes in mouse zygotes, Cell Stem Cell., vol. 15, No. 4, Oct. 2, 2014, pp. 459-471.

Simerly, et al., Nuclear transfer in the rhesus monkey: opportunities and challenges, Cloning Stem Cells., vol. 5, No. 4, 2003, pp. 319-331.

Simerly, et al., The paternal inheritance of the centrosome, the cell's microtubule-organizing center, in humans, and the implications for infertility, Nat Med., vol. 1, No. 1, Jan. 1995, pp. 47-52.

Skrzypek, et al., Azoospermia in a renal transplant recipient during sirolimus (rapamycin) treatment, Andrologia., vol. 39, No. 5, Oct. 2007, pp. 198-199.

Steves, et al., Per- and polyfluoroalkyl substances impact human spermatogenesis in a stem-cell-derived model, Syst Biol Reprod Med., vol. 64, No. 4, Aug. 2018, pp. 225-239.

Steves, et al., Ubiquitous Flame-Retardant Toxicants Impair Spermatogenesis in a Human Stem Cell Model, iScience., vol. 3, May 25, 2018, pp. 161-176.

Stice, et al., Nuclear reprogramming in nuclear transplant rabbit embryos, Biol Reprod., vol. 39, No. 3, Oct. 1988, pp. 657-664.

Stirchak, et al., Uncharged stereoregular nucleic acid analogs. 1. Synthesis of a cytosine-containing oligomer with carbamate internucleoside linkages, J. Organic Chem., vol. 52, No. 19, 1987, pp. 4202-4206.

Stone, et al., Embryo fragmentation as a determinant of blastocyst development in vitro and pregnancy outcomes following embryo transfer, Am J Obstet Gynecol., vol. 192, No. 6, Jun. 2005, pp. 2014-2019.

Swann, K, A cytosolic sperm factor stimulates repetitive calcium increases and mimics fertilization in hamster eggs, Development., vol. 110, No. 4, Dec. 1990, pp. 1295-1302.

Tanaka, et al., Fourteen babies born after round spermatid injection into human oocytes, Proc Natl Acad Sci U S A., vol. 112, No. 47, Nov. 24, 2015, pp. 14629-14634.

Tanaka, et al., Ninety babies born after round spermatid injection into oocytes: survey of their development from fertilization to 2 years of age, Fertil Steril., vol. 110, No. 3, Aug. 2018, pp. 443-451.

Voo, et al., Cloning of a mammalian transcriptional activator that binds unmethylated CpG motifs and shares a CXXC domain with DNA methyltransferase, human trithorax, and methyl-CpG binding domain protein 1, Mol Cell Biol., vol. 20, No. (Mar. 6, 2000, pp. 2108-2121.

Wallace, W Hamish B., Oncofertility and preservation of reproductive capacity in children and young adults, Cancer., vol. 117, No. (10 Suppl), May 15, 20111, pp. 2301-2310.

Zhao, et al., In Vitro Modeling of Human Germ Cell Development Using Pluripotent Stem Cells, Stem Cell Reports., vol. 10, No. 2, Feb. 13, 2018, pp. 509-523.

Zhou, et al., Complete Meiosis from Embryonic Stem Cell-Derived Germ Cells In Vitro, Cell Stem Cell., vol. 18, No. 3, Mar. 3, 2016, pp. 330-340.

* cited by examiner

DNA CONTENT PROFILE nhp2706 H2B GFP ESCs.H19

49.66%            50.34%

□ METHYLATED

□ UNMETHYLATED nhp2706 H2B GFP ESCs.SNRPN 49.66%            48.98%

□ METHYLATED

□ UNMETHYLATED

Human *SHANK3*    CCTGCAGAAACGGGACCACGAGGG
Rhesus *SHANK3*    CCTGCAGAAACGGGACCATGAGGG
                        Target site PAM
gRNA          GCTGCAGAAACGGGACCACGNGG WT Rhesus *SHANK3*  CCTGCAGAAACGGGACCATGAGGGCTTTGGTTTTG
Mutated *SHANK3*  CCTGCAGAAACGGGACCAT..............TTTGGTTTTG

COMPOSITIONS AND METHODS FOR IMPROVING EMBRYO DEVELOPMENT

CROSS-REFERENCE TO RELATED APPLICATIONS

This application is a continuation of U.S. application Ser. No. 17/265,157 filed Feb. 1, 2021, which is a National Phase application under 35 U.S.C. § 371 of International Application No. PCT/US2019/044589, filed on Aug. 1, 2019, which claims the benefit of and priority to U.S. Ser. No. 62/713,182, filed Aug. 1, 2018, which are specifically incorporated by reference herein in their entireties.

STATEMENT REGARDING FEDERALLY SPONSORED RESEARCH

This invention was made with government support under Grant No. OD020182 awarded by the National Institutes of Health. The government has certain rights in the invention.

REFERENCE TO THE SEQUENCE LISTING

The Sequence Listing XML submitted as a file named "UGA_2018-017-05_CON_ST26.xml," created on May 15, 2024 and having a size of 36,401 bytes is hereby incorporated by reference pursuant to 37 C.F.R. § 1.834(c)(1).

FIELD OF THE INVENTION

The invention is generally directed to compositions and methods for improving embryo development during, for example, in vitro fertilization.

BACKGROUND OF THE INVENTION

Infertility is now a progressive global health issue affecting more than 50 million couples worldwide. Since the 1970's, there has been a ~50% decrease in sperm parameters in Western men, sparking global concerns about a "sperm crisis" (Levine et al., *Hum Reprod Update* 23, 646-659, doi: 10.1093/humupd/dmx022 (2017)). Currently, ~15% of couples worldwide and ~12% of men in the United States are subfertile or infertile (Chandra et al., *Natl Health Stat Report,* 1-18, 11 p following 19 (2013), Gassei & Orwig, *Fertil Steril* 105, 256-266, doi:10.1016/j.fertnstert.2015.12.020 (2016), Louis et al., *Andrology* 1, 741-748, doi: 10.1111/j.2047-2927.2013.00110.x (2013)).

Some root causes for this infertility lie in genetic defects, but others are due to exposure to industrial and environmental toxicants, injury, or medical treatments such as alkylating chemotherapies which almost always result in sterility, especially in men (Bahadur, *Mol Cell Endocrinol* 169, 117-122, doi:S0303-7207(00)00364-6 [pii] (2000), Deutsch et al., *Am J Transplant* 7, 2414-2421, doi:AJT1929 [pii]10.1111/j.1600-6143.2007.01929.x (2007), Schlegel, *Minerva Ginecol* 61, 261-283 (2009), Skrzypek & Krause, *Andrologia* 39, 198-199, doi:AND787 [pii]10.1111/j.1439-0272.2007.00787.x (2007), Wallace, *Cancer* 117, 2301-2310, doi: 10.1002/cncr.26045 (2011)). While advances in fertility preservation during cancer therapies has improved fertile outcomes after treatment cessation, there still exists a large number of male patients that have survived cancer but are permanently sterile. Since 1980, Assisted Reproductive Technologies (ART) such as Intracytoplasmic Sperm Injection (ICSI) have aided couples with severe male factor infertility to achieve pregnancies. However, these techniques rely on the production of male gametes (sperm or spermatids) to fertilize a partner's oocyte in vitro. For those patients unable to provide sperm or spermatid samples, no treatment options are available.

Regardless of the root cause, men who are unable to produce gametes useful in ART are unable to father a child with their partner as no cures currently exist to treat their infertility. Thus, there remains a need for improved treatment options for male factor infertility.

It is an object of the invention to provide compositions and methods for increasing fertilization rates of sperm derived from male subjects with reduced fertility.

It is also an object of the present invention to provide compositions and methods for treating idiopathic male factor infertility.

It is another object of the invention to provide feeder cell-free compositions and methods of making functional male gametes.

SUMMARY OF THE INVENTION

Compositions and methods for improving embryo development are provided. Typically, the methods include administering into a female gamete, male gamete, or fertilized embryo an effective amount of a compound that increases bioavailability of a Ten-eleven translocation (TET) protein family to improve fertilization rate, or development of the fertilized embryo or a subsequent embryo resulting from fertilization of the female gamete by the male gamete. For example, the compound can be administered into an oocyte before, during, or after fertilization. The compound can be administered by, for example, an injection such as intracytoplasmic injection or electroporation. In preferred embodiments, the compound and the male gamete are administered into an oocyte in combination by intracytoplasmic sperm injection (ICSI) of sperm, spermatids, or other male gametes. The compositions and methods can increase the number of fertilized oocytes that develop, for example, to the two-cell, four-cell, eight-cell, sixteen-cell, morula, and/or blastocyte stages following fertilization; increase the rate (e.g., speed) at which an individual embryo develops to the two-cell, four-cell, eight-cell, sixteen-cell, morula, and/or blastocyte stages following fertilization; improve the rate of embryo cleavage; or a combination thereof. In some embodiments, the increase and/or improvement is similar to fertilization and subsequent embryo development using normal spermatozoa.

The compositions and methods can be used to treat idiopathic male factor infertility, allowing infertile/sub-fertile/sterile men to father their own genetic offspring. The disclosed methods typically include injecting or otherwise delivering a compound that increases TET bioavailability into a male gamete preferably, spermatids or haploid spermatogenic cells (or a female gamete, or fertilized embryo). In some embodiments, spermatids or haploid spermatogenic cells are from a male subject who does not produce mature spermatozoa. Immature sperm cells such as haploid round spermatids or elongated spermatids from male with low semen quality have lower levels of TET protein compared to mature spermatozoa resulting in insufficient TET bioactivity to achieve efficient fertilization and subsequent development. Thus the increase of TET bioactivity by co-injecting or otherwise delivering haploid round spermatids or elongated spermatids with a compound that increases TET bioactivity can improve fertilization and embryo development with higher quantity and quality embryos for embryo transfer.

The TET protein can be TET1, TET2, TET3, or a combination thereof. The compound for increasing TET bioavailability can be a small molecule, a TET polypeptide or protein, a fusion protein including a TET polypeptide or protein, an isolated nucleic acid encoding a TET polypeptide or protein or TET fusion protein, an agent such as a transcription factor that increases endogenous expression of a TET polypeptide or protein, or a combination thereof.

In preferred embodiments, the compound increases bioavailability of TET3. Exemplary compounds include TET3 polypeptide or protein, a fusion protein including a TET3 polypeptide or protein, an isolated nucleic acid encoding a TET3 polypeptide or protein or TET3 fusion protein, an agent such as a transcription factor or small molecule that increases endogenous expression of a TET3 polypeptide or protein, or a combination thereof. For example, the TET3 polypeptide or protein can be full-length TET3 or a functional fragment thereof. In particular embodiments, the TET3 polypeptide or protein is human TET3, a functional fragment thereof, or a variant thereof having at least 85% sequence identity to human TET3.

The male gamete can be a round spermatid, elongating spermatid, condensing spermatid, or condensed spermatid derived in vitro or in vivo. In some embodiments, the male gamete is prepared by differentiating an embryonic stem cell, induced pluripotent stem cell, or spermatogonia stem cell into a spermatid. Methods for doing so are also provided.

Methods of modifying the genome of a male gamete or an embryo are also provided. In some embodiments, the method includes administering to the induced pluripotent stem cells, male gamete or embryo, an effective amount of a gene editing composition to correct a gene mutation or anomaly in the genome thereof. A preferred gene editing composition is a CRISPR/Cas system but other gene editing methods are not excluded. In some embodiments, the gene editing compositions also includes a donor polynucleotide with sufficient homology to the genomic sequence at the target site to modify the genome at or adjacent to the target site by homology-directed repair. The donor polynucleotide can introduce one or more insertions, deletions, or substitutions in the genome. In some embodiments, the insertions, deletions, or substitutions correct a mutation, such as a mutation associated with genetic disease or condition.

Thus, the compositions and methods disclosed herein include, but are not limited to, composition and methods for increasing the bioavailability/co-injecting TET proteins to, for example, improve ICSI/embryo development rates when injecting immature sperm/spermatids; methods of using patient specific pluripotent stem cells to generate functional gametes in vitro and to treat, e.g., male factor infertility; feeder-free differentiation methods and protocols for generating functional gametes from patient specific stem cells including spermatogonia; and using gene editing tools to correct mutations disease-causing mutations in, for example fibroblasts or iPSCs, prior to differentiation into functional gametes.

BRIEF DESCRIPTION OF THE DRAWINGS

FIG. 6A shows a population distribution showing wild-type (25%) and mutant (75%) genotypes. FIG. 6B shows a distribution of the timing of mutation during early embryonic division. n=96.

DETAILED DESCRIPTION OF THE INVENTION

I. Definitions

Figure 1A:
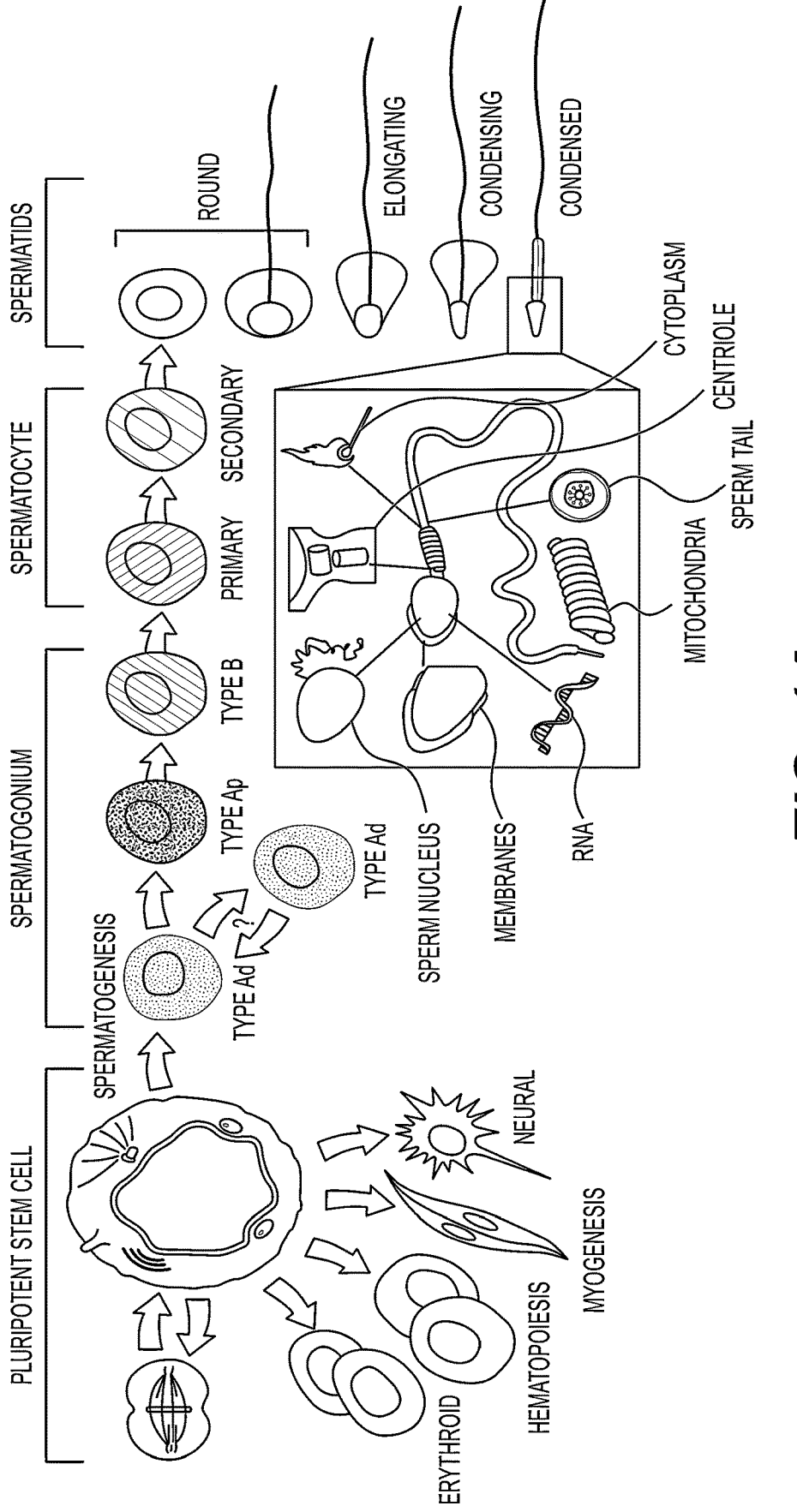
FIG. 1A is a schematic representing various stages of spermatogenesis that can be generated in vitro up to the elongating spermatid stage.
Figure 1B:
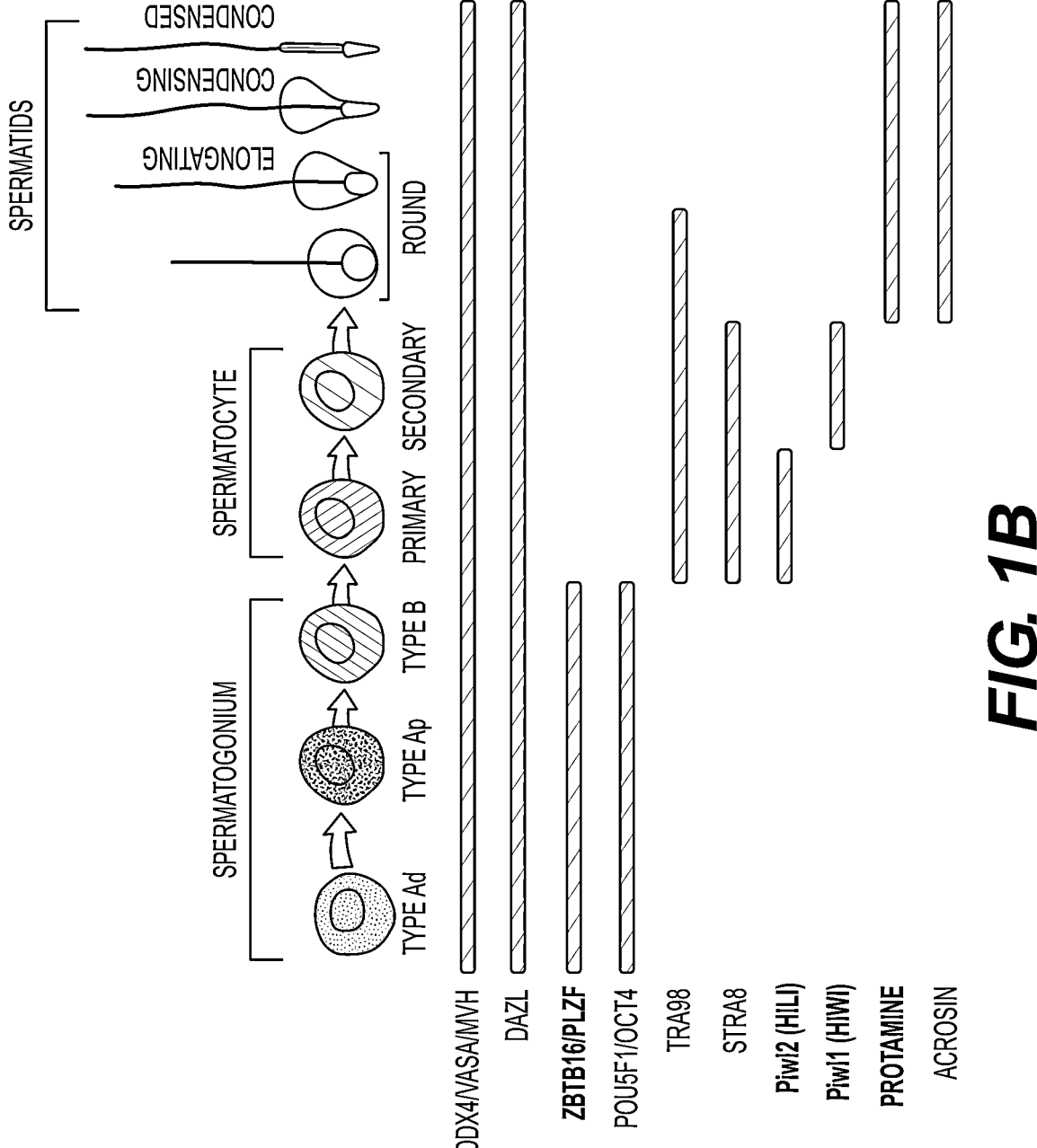
FIG. 1B is an illustration showing differentiating sperm cell markers: DDX4/VASA/: DEAD-Box Helicase 4; DAZL:Deleted in AZoospermia like; ZBTB16/PLZF: promyelocytic leukemia zinc finger; TRA98: Germ cell specific marker; STRA8: Stimulated BY Retinoic Acid 8; Piwil2: piwi like protein 2; Piwil1: Piwi-like protein 1; Protamine and Acrosine, and expression thereof during spermatogenesis.

As used herein, the term "carrier" or "excipient" refers to an organic or inorganic ingredient, natural or synthetic inactive ingredient in a formulation, with which one or more active ingredients are combined.

As used herein, the term "pharmaceutically acceptable" means a non-toxic material that does not interfere with the effectiveness of the biological activity of the active ingredients.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

As used herein, the terms "effective amount" or "therapeutically effective amount" means a dosage sufficient to alleviate one or more symptoms of a disorder, disease, or condition being treated, or to otherwise provide a desired pharmacologic and/or physiologic effect. The precise dosage will vary according to a variety of factors such as subject-dependent variables (e.g., age, immune system health, etc.), the disease or disorder being treated, as well as the route of administration and the pharmacokinetics of the agent being administered.

As used herein, the term "prevention" or "preventing" means to administer a composition to a subject or a system at risk for or having a predisposition for one or more symptom caused by a disease or disorder to cause cessation of a particular symptom of the disease or disorder, a reduction or prevention of one or more symptoms of the disease or disorder, a reduction in the severity of the disease or disorder, the complete ablation of the disease or disorder, stabilization or delay of the development or progression of the disease or disorder.

As used herein, the term "identity," as known in the art, is a relationship between two or more polypeptide sequences, as determined by comparing the sequences. In the art, "identity" also means the degree of sequence relatedness between polypeptide as determined by the match between strings of such sequences. "Identity" and "similarity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073 (1988).

Preferred methods to determine identity are designed to give the largest match between the sequences tested. Methods to determine identity and similarity are codified in publicly available computer programs. The percent identity between two sequences can be determined by using analysis software (i.e., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). The default parameters are used to determine the identity for the polypeptides of the present disclosure.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

As used herein, the terms "subject," "individual," and "patient" refer to any individual who is the target of treatment using the disclosed compositions. The subject can be a vertebrate, for example, a mammal. Thus, the subject can be a human. The subjects can be symptomatic or asymptomatic. The term does not denote a particular age or sex. Thus, adult and newborn subjects, whether male or female, are intended to be covered. A subject can include a control subject or a test subject.

As used herein, the term "operably linked" refers to a juxtaposition wherein the components are configured so as to perform their usual function. For example, control sequences or promoters operably linked to a coding sequence are capable of effecting the expression of the coding sequence, and an organelle localization sequence operably linked to protein will direct the linked protein to be localized at the specific organelle.

As used herein, "treat" means to prevent, reduce, decrease, or ameliorate one or more symptoms, characteristics or comorbidities of an age-related disease, disorder or condition; to reverse the progression of one or more symptoms, characteristics or comorbidities of an age related disorder; to halt the progression of one or more symptoms, characteristics or comorbidities of an age-related disorder; to prevent the occurrence of one or more symptoms, characteristics or comorbidities of an age-related disorder; to inhibit the rate of development of one or more symptoms, characteristics or comorbidities or combinations thereof.

As used herein, the term "construct" refers to a recombinant genetic molecule having one or more isolated polynucleotide sequences. Genetic constructs used for transgene expression in a host organism include in the 5'-3' direction, a promoter sequence; a sequence encoding a gene of interest; and a termination sequence. The construct may also include selectable marker gene(s) and other regulatory elements for expression.

As used herein, the term "gene" refers to a DNA sequence that encodes through its template or messenger RNA a sequence of amino acids characteristic of a specific peptide, polypeptide, or protein. The term "gene" also refers to a DNA sequence that encodes an RNA product. The term gene as used herein with reference to genomic DNA includes intervening, non-coding regions as well as regulatory regions and can include 5' and 3' ends.

As used herein, the term "vector" refers to a replicon, such as a plasmid, phage, or cosmid, into which another DNA segment may be inserted so as to bring about the replication of the inserted segment. The vectors can be expression vectors.

As used herein, the term "expression vector" refers to a vector that includes one or more expression control sequences.

As used herein, the term "expression control sequence" refers to a DNA sequence that controls and regulates the transcription and/or translation of another DNA sequence. Control sequences that are suitable for prokaryotes, for example, include a promoter, optionally an operator sequence, a ribosome binding site, and the like. Eukaryotic cells are known to utilize promoters, polyadenylation signals, and enhancers.

As used herein, the terms "transformed," "transgenic," "transfected" and "recombinant" refer to a host organism into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed," "non-transgenic," or "non-recombinant" host refers to a wild-type organism, e.g., a bacterium or plant, which does not contain the heterologous nucleic acid molecule.

II. Compositions and Methods of Increasing TET Bioavailability

Compositions and methods for treating male factor infertility, improving fertilization rates, and enhancing embryo development are provided. The disclosed compositions and methods can be used to enable infertile/sub-fertile/sterile men to father their own genetic offspring. The compositions and methods are particularly advantageous for male subjects including, but not limited to, those who do not produce mature spermatozoa. Additionally provided are strategies for using genome editing tools such as CRISPR technology to correct inherited mutations and perform thorough genetic assessments in subject-specific induced pluripotent stem cells prior to differentiation into spermatids, thus providing for production and selection of genetically corrected embryos. Any of the disclosed methods can be used alone or in any combination.

There are three TET family proteins, TET1, TET2, and TET3. TET proteins are large (~180- to 230-kDa) multidomain enzymes, each containing a conserved double-stranded β-helix (DSBH) domain, a cysteine-rich domain, and binding sites for the cofactors Fe(II) and 2-oxoglutarate (2-OG) that together form the core catalytic region in the C terminus (Rasmussen and Helin, *Genes Dev.*, 30(7): 733-750 (2016)).

Structural studies indicate that the core catalytic region preferentially binds cytosines in a CpG context but does not interact with surrounding DNA bases and shows little or no specificity for flanking DNA sequences. In addition to their catalytic domain, TET1 and TET3 have an N-terminal CXXC (SEQ ID NO:11) zinc finger domain that can bind DNA (Long, et al., *Biochem Soc Trans.* 41(Pt 3): 727-740 (2013), Voo, et al., *Mol Cell Biol.,* 20(6): 2108-2121 (2000)).

TET proteins catalyze the successive oxidation of 5-methylcytosine (5mC) to 5-hydroxymethylcytosine (5hmC), 5-formylcytosine (5fC), and 5-carboxylcytosine (5caC). These 5mC oxidation products intermediates in the conversion of 5mC to unmodified cytosines, thus providing the first steps in a pathway for active DNA demethylation and indicating that DNA methylation patterns are not as static as initially assumed.

The erasure of methylated marks in zygotes shortly after fertilization, specifically in the male genome of in vitro derived spermatids, might have profound impact on zygotic genome activation (ZGA) and subsequent activation of the embryonic genome. Unlike rodent, rhesus macaque embryonic genome activation (EGA) occurred at the 8-cell stage instead of 2-cell stage in rodents (Chitwoord et al., *Biol Reprod,* 97:353-364, 2017). In mice, shortly after fertilization there is a global loss of 5mC in paternal genome with rapid conversion to 5hmC and its downstream oxidation products including 5fC and 5caC which were further catalyzed by the maternally stored Tet3 proteins (Shen et al., *Cell Stem Cell.* 2; 15(4):459-71 (2014)). In human, TET1-3 proteins are successively expressed during spermatogenesis. With TET2 expressed in the cytoplasm of late pachytene spermatocytes of Stage V, TET1 expressed in the nuclei of Step I round spermatids at Stage 1 and Tet3 started to express in nuclei of Step 3 spermatids at Stage III while 5hmC appears in Step 5 elongated spermatids (Ni et al., *Hum Reprod.,* 31(7); 1411-24, (2016)). The expression levels of TET enzymes are positively correlated with progressive sperm motility which is important for male fertility.

A report on de novo DNA methylation during rhesus pre-implantation development indicated that TET3 is expressed during the major wave of active demethylation in early embryos shortly after fertilization while TET1/2 started to express from 8-cell stage onward when EGA initiated (Gao et al., *Cell Res,* 27:526-539 (2017)).

A. Methods of Increasing TET Bioavailability

The results presented below are consistent with the conclusion that TET3 erases methylated marks shortly in spermatids, and demonstrate the importance of timing of TET3 activity or paternal demethylation during ZGA and subsequent EGA events. Compared to injecting sperm extract alone, co-injection of TET3-pDNA improved cleavage rate while co-injection with Tet3-mRNA further improve development up to 8 cell stage with development to 16 cell stage and morula at low rate. Co-injection with TET3 protein significantly improved cleavage rate with majority of embryo develop beyond 8-cell stage and with close to 12% reached to blastocyst stage. In addition, TET3 improved the morphology and development rate of preimplantation embryos, while reducing fragmentation.

Compositions and method for improving preimplantation embryos are provided. Typically, the methods typically include increasing the bioavailability of a ten eleven translocation (TET) family protein in a preimplantation embryo.

The compositions and methods can increase the number of fertilized oocytes that develop, for example, to the two-cell, four-cell, eight-cell, sixteen-cell, morula, and/or blastocyte stages following fertilization; increase the rate at which an individual embryo develops to the two-cell, four-cell, eight-cell, sixteen-cell, morula, and/or blastocyte stages following fertilization; or a combination thereof. Embryo morphology and reduced fragmentation can be used to measure improved viability. For example, in some embodiments, the rate of embryo cleavage is improved. Also, the development rate or advancement to each subsequent stage can also be used to measure improvement. For example, TET injected embryos show similar development time such as reaching blastocyst stage by Day 7 after fertilization, which is similar to those fertilized using normal spermatozoa.

The TET protein can be increased by, for example, injecting or otherwise delivering a compound that increases the bioavailability of a TET protein into a male gamete, e.g., a haploid spermatocytes, spermatid or spermatozoa; an oocyte; or fertilized embryo, particularly an early stage embryo e.g., a two-cell, four-cell, eight-cell, sixteen-cell, morula, and/or blastocyte stage embryo.

Preferred compounds are discussed in more detail below and include, but are not limited to TET protein; a nucleic acid encoding a TET protein, including but not limited to TET mRNA, or an expression vector encoding TET; or a combination thereof. Chemicals or small molecules that enhance TET expression, for example TET3, in haploid spermatids during in vitro differentiation can be used.

In preferred embodiments, the TET is TET3. A preferred method of increasing the presence of a TET protein such as TET3 includes co-injection a compound that increases bioavailability of a TET along with immature spermatids into oocytes at the time of intercytoplasmic sperm injection (ICSI) to improve preimplantation embryo development and blastocyst rates.

In some embodiments, the methods also include injection of sperm extract. The sperm extract can be prepared from ejaculated sperm as follows. Ejaculated sperm is washed with TH3 medium by centrifugation at 1500 rpm for 5 min. The supernatant is aspirated out the supernatant and the sperm concentration adjusted to 5-10×10^8 sperm/mL. Sperm layer is then be pelleted and washed three times with modified intracellular buffer (ICB) by centrifugation at 1,400 rpm (Eppendorf benchtop centrifuge) for 5 min at RT. This is followed by Lysing by four freeze-thaw cycles. The lysed samples are then be spin at 100,000×g (e.g. 48,000 rpm of Beckman micro-ultracentrifuge) for 1 hour at 4 C. The supernatant is transferred to new clean Eppendorf tube, and kept on ice. It is then concentrated (~3-5 folds) by using centrocon-30 microfiltration membrane (Amicon Cat #4208) and centrifugation at 3000×g for 20 min. Aliquoted 10 uL per vial and stored at –80° C.

TABLE 2

| ICB buffer (pH 7.5) | | | | |
|---|---|---|---|---|
| | Vender/Cat# | Final Conc. | g/50 mL | g/100 mL |
| KCL | Sigma P5405 | 120 mM | 0.44735 | 0.8947 |
| HEPES | Sigma H6147 | 20 mM | 0.2833 | 0.5666 |
| EGTA | Sigma E3889 | 100 μM | 0.0019 | 0.0038 |
| Sodium glycero-phosphate | Sigma G-5422 FW = 216.04 <0.1% alpha-L-isomer | 10 mM | 0.108 | 0.2160 |

In some embodiments, preimplantation embryos, particularly blastocysts, treated with a TET such as TET3 have improved morphology, an improved likelihood of development, reduced rate of fragmentation, or a combination thereof.

The compositions can also include trichostatin A (TSA), and methods can include administering TSA. TSA is an organic compound that selectively inhibits the class I and II mammalian histone deacetylase (HDAC) families of enzymes, but not class III HDACs (i.e., sirtuins). TSA can alter gene expression by interfering with the removal of acetyl groups from histones (histone deacetylases, HDAC), altering the ability of DNA transcription factors to access the DNA molecules inside chromatin.

B. Compounds for Increasing TET Bioavailability

Compounds for increasing the bioactivity of TET protein, and formulations formed therewith are provided. In some embodiments, the compound is a small molecule, a TET polypeptide or protein, a fusion protein including a TET polypeptide or protein, an isolated nucleic acid encoding a TET polypeptide or protein or TET fusion protein, or an agent such as a transcription factor that increases endogenous expression of a TET polypeptide or protein. The compound can increase the expression or bioavailability of a TET.

In some embodiments, the compound has at 70%, at least 75%, at least 80%, at least 85%, at least 90%, at least 95%, at least 98%, at least 99%, or more, sequence identity to TET1, TET2, or TET3, in particular human TET1, TET2, or TET3.

For example, in some embodiments, the compound is a human wildtype TET protein such as SEQ ID NOS:1, 9, or 10, or a functional fragment thereof, or a variant thereof with at least 50, 60, 70, 80, 85, 90, 95, 96, 97, 98, or 99% sequence identity to SEQ ID NOS: 1, 9, or 10, including but not limited to human TET3 isoform 2, 3, or 4. In some embodiments, the compound is a TET protein such as SEQ ID NOS: 13, or a functional fragment thereof, or a variant thereof with at least 50, 60, 70, 80, 85, 90, 95, 96, 97, 98, or 99% sequence identity to SEQ ID NOS: 13.

In some embodiments, the compound is a nucleic acid encoding a human wildtype TET3 protein such as SEQ ID NO:2, or a functional fragment thereof, or a variant thereof with at least 50, 60, 70, 80, 85, 90, 95, 96, 97, 98, or 99% sequence identity to SEQ ID NO:2. In some embodiments, the compound includes a nucleic acid sequence such as SEQ ID NOS:12, or a functional fragment thereof, or a variant thereof with at least 50, 60, 70, 80, 85, 90, 95, 96, 97, 98, or 99% sequence identity to SEQ ID NOS:12.

In some embodiments, the compound is a fragment of a fully length TET protein. Such fragments usually encode proteins of at least 5 amino acids in length. In some embodiments, they may encode proteins of 6 to 10, 11 to 15, 16 to 25, 26 to 50, 51 to 75, 76 to 100 or 101 to 250 or 250 to 500, 500 to 1000, 1000 to 1500 or 1500 to 2000 amino acids. Fragments may include sequences with one or more amino acids removed, for example, C-terminus truncated protein, N-terminus truncated proteins, or a combination thereof. Fragments may also include nucleic acids that encode proteins with or without a particular domain, for example fragments where the CXXC (SEQ ID NO:11) (DNA-binding) domain, or catalytic domain is absent.

In some embodiments, the compound is one that increases bioactivity of an endogenous TET, e.g., endogenous TET3. Such compounds include factors that increase the expression, or increase the half-life, of an endogenous TET. Factors that increase expression of endogenous TET proteins include, for example, TET transcription factors. TET transcription factors can be provided as a recombinant polypeptide, or an isolated nucleic acid encoding the transcription factor.

1. TET Sequences

Protein and nucleic acid sequences for TET proteins are known in the art, and include, for example, Table 1, which provide Uniprot Database Accession numbers for human and rhesus macaque TET1, TET2, and TET3 proteins, the contents of each of which are specifically incorporated by reference in their entireties.

TABLE 1

Exemplary TET Accession Numbers

| Entry | Entry name | Protein names | Gene names | Organism | Length |
|---|---|---|---|---|---|
| Q8NFU7 | TET1_HUMAN | Methylcytosine dioxygenase TET1 | TET1 CXXC6, KIAA1676, LCX | *Homo sapiens* (Human) | 2,136 |
| F7EF05 | F7EF05_MACMU | Tet methylcytosine dioxygenase 1 | TET1 | *Macaca mulatta* (Rhesus macaque) | 2,043 |
| Q6N021 | TET2_HUMAN | Methylcytosine dioxygenase TET2 | TET2 KIAA1546, Nbla00191 | *Homo sapiens* (Human) | 2,002 |
| F7DR39 | F7DR39_MACMU | Tet methylcytosine dioxygenase 2 | TET2 | *Macaca mulatta* (Rhesus macaque) | 2,020 |
| O43151 | TET3_HUMAN | Methylcytosine dioxygenase TET3 | TET3 KIAA0401 | *Homo sapiens* (Human) | 1,660 |
| F7D294 | F7D294_MACMU | Tet methylcytosine dioxygenase 3 | TET3 | *Macaca mulatta* (Rhesus macaque) | 1,795 |
| H9FJH1 | H9FJH1_MACMU | Methylcytosine dioxygenase TET3 | TET3 | *Macaca mulatta* (Rhesus macaque) | 348 |

Sequences, fragments, and derivatives of TET family proteins are also described in U.S. Published Application Nos. 2011/0236894 and 2016/0186207.

In particularly preferred embodiments, the compound that increases TET bioavailability is a TET1, TET2, or TET3 polypeptide or protein, a fusion protein including a TET1, TET2, or TET3 polypeptide or protein, an isolated nucleic acid encoding a TET1, TET2, or TET3 polypeptide or protein or TET1, TET2, or TET3 fusion protein, or any combination thereof. The isolated nucleic acid can be, for example, TET1, TET2, or TET3 mRNA or an expression vector encoding TET1, TET2, or TET3. Variant polypeptides having at least 50%, 60%, 70%, 75%, 80%, 85%, 90%, 95%, or more sequence identity to the TET sequences provided herein by sequence or accession number are also provided.

An exemplary human TET3 amino acid sequence (i.e., 'canonical' isoform 1) is

```
        (SEQ ID NO: 1, UniProtKB - O43151(TET3_HUMAN)
MDSGPVYHGDSRQLSASGVPVNGAREPAGPSLLGTGGPWRVDQKPDWEAA

PGPAHTARLEDAHDLVAFSAVAEAVSSYGALSTRLYETFNREMSREAGNN

SRGPRPGPEGCSAGSEDLDTLQTALALARHGMKPPNCNCDGPECPDYLEW

LEGKIKSVVMEGGEERPRLPGPLPPGEAGLPAPSTRPLLSSEVPQISPQE

GLPLSQSALSIAKEKNISLQTAIAIEALTQLSSALPQPSHSTPQASCPLP

EALSPPAPFRSPQSYLRAPSWPVVPPEEHSSFAPDSSAFPPATPRTEFPE
```

-continued
```
AWGTDTPPATPRSSWPMPRPSPDPMAELEQLLGSASDYIQSVFKRPEALP

TKPKVKVEAPSSSPAPAPSPVLQREAPTPSSEPDTHQKAQTALQQHLKHK

RSLFLEQVHDTSFPAPSEPSAPGWWPPPSSPVPRLPDRPPKEKKKKLPTP
```

-continued
```
AGGPVGTEKAAPGIKPSVRKPIQIKKSRPREAQPLFPPVRQIVLEGLRSP

ASQEVQAHPPAPLPASQGSAVPLPPEPSLALFAPSPSRDSLLPPTQEMRS

PSPMTALQPGSTGPLPPADDKLEELIRQFEAEFGDSFGLPGPPSVPIQDP

ENQQTCLPAPESPFATRSPKQIKIESSGAVTVLSTTCFHSEEGGQEATPT

KAENPLTPTLSGFLESPLKYLDTPTKSLLDTPAKRAQAEFPTCDCVEQIV

EKDEGPYYTHLGSGPTVASIRELMEERYGEKGKAIRIEKVIYTGKEGKSS

RGCPIAKWVIRRHTLEEKLLCLVRHRAGHHCQNAVIVILILAWEGIPRSL

GDTLYQELTDTLRKYGNPTSRRCGLNDDRTCACQGKDPNTCGASFSFGCS

WSMYFNGCKYARSKTPRKFRLAGDNPKEEEVLRKSFQDLATEVAPLYKRL

APQAYQNQVTNEEIAIDCRLGLKEGRPFAGVTACMDFCAHAHKDQHMLYN

GCTVVCTLTKEDNRCVGKIPEDEQLHVLPLYKMANTDEFGSEENQNAKVG

SGAIQVLTAFPREVRRLPEPAKSCRQRQLEARKAAAEKKKIQKEKLSTPE

KIKQEALELAGITSDPGLSLKGGLSQQGLKPSLKVEPQNHFSSFKYSGNA

VVESYSVLGNCRPSDPYSMNSVYSYHSYYAQPSLTSVNGFHSKYALPSFS

YYGFPSSMPVFPSQFLGPGAWGHSGSSGSFEKKPDLHALHNSLSPAYGGA

EFAELPSQAVPTDAHHPTPHHQQPAYPGPKEYLLPKAPLLHSVSRDPSPF

AQSSNCYNRSIKQEPVDPLTQAEPVPRDAGKMGKTPLSEVSQNGGPSHLW

GQYSGGPSMSPKRTNGVGGSWGVFSSGESPAIVPDKLSSFGASCLAPSHF

TDGQWGLFPGEGQQAASHSGGRLRGKPWSPCKFGNSTSALAGPSLTEKPW
```

-continued

ALGAGDFNSALKGSPGFQDKLWNPMKGEEGRIPAAGASQLDRAWQSFGLP

LGSSEKLFGALKSEEKLWDPFSLEEGPAEEPPSKGAVKEEKGGGGAEEEE

EELWSDSEHNFLDENIGGVAVAPAHGSILIECARRELHATTPLKKPNRCH

PTRISLVFYQHKNLNQPNHGLALWEAKMKQLAERARARQEEAARLGLGQQ

EAKLYGKKRKWGGTVVAEPQQKEKKGVVPTRQALAVPTDSAVTVSSYAYT

KVTGPYSRWI, which is specifically incorporated by reference herein in its entirety).

TET 3 Isoform 2 (identifier: 043151-2) differs from the canonical sequence as follows: 1440-1555: Missing.

TET3 Isoform 3 (identifier: 043151-3) differs from the canonical sequence as follows: 728-1660: Missing.

TET3 Isoform 4 (identifier: 043151-4) differs from the canonical sequence as follows: 1-1: M→

(SEQ ID NO: 3)

MSQFQVPLAVQPDLPGLYDFPQRQVMVGSFPGSGLSMAGSESQLRG

GGDGRKKRKRCGTCEPCRRLENCGACTSCTNRRTHQICKLRKCEVL

KKKVGLLKEVEIKAGEGAGPWGQGAAVKTGSELSPVDGPVPGQM.

A nucleic acid sequence encoding human TET3 is (SEQ ID NO: 2 atgagccagtttcaggtgcccctggccgtccagccggacctgccaggcct ttatgacttccctcagcgccaggtgatggtagggagcttcccggggtctg ggctctccatggctgggagtgagtcccaactccgagggggtggagatggt cgaaagaaacggaaacggtgtggtacttgtgagccctgccggcggctgga aaactgtggcgcttgcactagctgtaccaaccgccgcacgcaccagatct gcaaactgcgaaaatgtgaggtgctgaagaaaaaagtagggcttctcaaq gaggtggaaataaaggctggtgaaggagccgggccgtgggacaaggagc ggctgtcaagacaggctcagagctcagcccagttgatggacctgttccag gtcagatggactcagggccagtgtaccatggggactcacggcagctaagc gcctcaggggtgccggtcaatggtgctagagagcccgctggacccagtct gctgggactggggggtccttggcgggtagaccaaaagcccgactgggagg ctgccccaggcccagctcatactgctcgcctggaagatgcccacgatctg gtggcctttttcggctgtggccgaagctgtgtcctcttatggggcccttag caccccggctctatgaaaccttcaaccgtgagatgagtcgtgaggctggga acaacagcaggggacccggccagggcctgagggctgctctgctggcagc gaagaccttgacacactgcagacggccctggccctcgcgcggcatggtat gaaaccacccaactgcaactgcgatgcccagaatgccctgactacctcg agtggctggaggggaagatcaagtctgtggtcatggaaggaggggaggag cggcccaggctcccagggcctctgcctcctggtgaggccggcctcccagc accaagcaccaggccactcctcagctcagaggtgccccagatctctcccc aagagggcctgcccctgtcccagagtgccctgagcattgccaaggaaaaa aacatcagcttgcagaccgccattgccattgaggccctcacacagctctc -continued ctctgccctcccgcagccttctcattccaccccccaggcttcttgccccc ttcctgaggccttgtcacctcctgcccctttcagatctccccagtcttac ctccgggctccctcatggcctgtggttcctcctgaagagcactcatcttt tgctcctgatagctctgccttccctccagcaactcctagaactgagttcc ctgaagcctggggcactgacacccctccagcaacgccccggagctcctgg cccatgcctcgcccaagccccgatcccatggctgaactggagcagttgtt gggcagcgccagtgattacatccagtcagtattcaagcggcctgaggccc tgcctaccaagcccaaggtcaaggtggaggcaccctcttcctccccggcc ccggcccccatccctgtacttcagagggaggctcccacgccatcctcgga gcccgacacccaccagaaggcccagaccgccctgcagcagcacctccacc acaagcgcagcctcttcctagaacaggtgcacgacacctccttccctgct ccttcagagccttctgctcctggctggtggcccccaccaagttcacctgt cccacggcttccagacagaccacccaaggagaagaagaagaagctcccaa caccagctggaggtcccgtgggaacggagaaagctgcccctgggatcaag cccagtgtccgaaagcccattcagatcaagaagtccaggccecgggaagc acagcccctcttcccacctgtccgacagattgtcctggaagggcttaggt ccccagcctcccaggaagtgcaggctcatccaccggcccctctgcctgcc tcacagggctctgctgtgcccctgcccccagaaccttctcttgcgctatt tgcacctagtccctccagggacagcctgctgccccctactcaggaaatga ggtccccagccccatgacagccttgcagccaggctccactggccctctt cccctgccgatgacaagctggaagagctcatccggcagtttgaggctga atttggagatagctttgggcttcccggccccccttctgtgcccattcagg acccccgagaaccagcaaacatgtctcccagcccctgagagcccctttgct acccgttcccccaagcaaatcaagattgagtcttcggggggctgtgactgt gctctcaaccacctgcttccattcagaggagggaggacaggaggccacac ccaccaaggctgagaacccactcacacccaccctcagtggcttcttggag tcacctcttaagtacctggacacacccaccaagagtctgctggacacacc tgccaagagagcccaggccgagttccccacctgcgattgcgtcgaacaaa tagtggagaaagatgaaggtccatattatactcacttgggatctggcccc acggtcgcctctatccgggaactcatggaggagcggtatggagagaaggg gaaagccatccggatcgagaaggtcatctacacggggaaggagggaaaga gctcccgcggttgccccattgcaaagtaggtgatccgcaggcacacgctg gaggagaagctactctgcctggtgcggcaccgggcaggccaccactgcca gaacgctgtgatcgtcatcctcatcctggcctgggagggcattccccgta gcctcggagacaccctctaccaggagctcaccgacaccctccggaagtat gggaaccccaccagccggagatgcggcctcaacgatgaccggacctgcgc ttgccaaggcaaagaccccaacacctgtggtgcctccttctcctttggtt gttcctggagcatgtacttcaacggctgcaagtatgctcggagcaagaca cctcgcaagttccgcctcgcaggggacaatcccaaagaggaagaagtgct ccggaagagtttccaggacctggccaccgaagtcgctcccctgtacaagc gactggcccctcaggcctatcagaaccaggtgaccaacgaggaaatagcg -continued

```
attgactgccgtctggggctgaaggaaggacggcccttcgcggggggtcac ggcctgcatggacttctgtgcccacgcccacaaggaccagcataacctct acaatgggtgcaccgtggtctgcaccctgaccaaggaagacaatcgctgc gtgggcaagattcccgaggatgagcagctgcatgttctccccctgtacaa gatggccaacacggatgagtttggtagcgaggagaaccagaatgcaaagg tgggcagcggagccatccaggtgctcaccgccttcccccgcgaggtccga cgcctgcccgagcctgccaagtcctgccgccagcggcagctggaagccag aaaggcagcagccgagaagaagaagattcagaaggagaagctgagcactc cggagaagatcaagcaggaggccctggagctggcgggcattacgtcggac ccaggcctgtctctgaagggtggattgtcccagcaaggcctgaagccctc cctcaaggtggagccgcagaaccacttcagctccttcaagtacagcggca acgcggtggtggagagctactcggtgctgggcaactgccggccctccgac ccttacagcatgaacagcgtgtactcctaccactcctactatgcacagcc cagcctgacctccgtcaatggcttccactccaagtacgctctcccgtctt ttagctactatggctttccatccagcaacccgtcttccctctcagttc ctgggtcctggtgcctggggggcacagtggcagcagtggcagtttgagaa gaagccagacctccacgctctgcacaacagcctgagcccggcctacggtg gtgctgagtttgccgagctgcccagccaggctgttcccacagacgccac cacccactcctcaccaccagcagcctgcgtacccaggccccaaggagta tctgcttcccaaggcccccctactccactcagtgtccagggacccctccc cctttgcccagagctccaactgctacaacagatccatcaagcaagagcca gtagacccgctgacccaggctgagcctgtgcccagagacgctggcaagat gggcaagacacctctgtccgaggtgtctcagaatggaggacccagtcacc tttggggacagtactcaggagcccaagcatgtcccccaagaggactaac ggtgtgggtggcagctggggtgtgttctcgtctggggagagtcctgccat cgtccctgacaagctcagttcctttggggccagctgcctggcccettccc acttcacagatggccagtggggctgttccccggtgaggggcagcaggca gcttcccactctggaggacggctgcgaggcaaaccgtggagcccctgcaa gtttgggaacagcacctcggccttggctgggcccagcctgactgagaagc cgtgggcgctgggggcagggatttcaactcggccctgaaaggtagtcct gggttccaagacaagctgtggaacccatgaaaggagaggagggcaggat tccagccgcaggggccagccagctggacagggcctggcagtcctttggtc tgcccctgggatccagcgagaagctgtttggggctctgaagtcagaggag aagctgtgggaccccttcagcctggaggaggggccggctgaggagccccc cagcaagggagcggtgaaggaggagaaaggcggtggtggtgcggaggagg aagaggaggagctgtggtcggacagtgaacacaacttcctggacgagaac atcgcggcgtggccgtggccccagcccacggctccatcctcatcgagtg tgcccggcgggagctgcacgccaccacgccgcttaagaagcccaaccgct gccaccccaccgcatctcgctggtcttctaccagcacaagaacctcaac cagcccaaccacgggctggccctctgggaagccaagatgaagcagctggc
```

16

-continued

```
ggagagggcacgggcacgggcaggaggaggctgcccggctgggcctgggcc agcaggaggccaagctctacgggaagaagcgcaagtggggggggcactgtg gttgctgagccccagcagaaagagaagaaggggggtcgtcccccacccggca ggcactggctgtgcccacagactcggcggtcaccgtgtcctcctatgcct acacgaaggtcactggcccctacagccgctggatctag,
```

GenBank: HQ220209.1. *Homo sapiens* putative methayley-
toxine dioxygenase (TET3) mRNA, complete cds, which is
specifically incorporated by reference herein in its entirety).
An exemplary human TET2 amino acid sequence:

```
     (SEQ ID NO: 9, UniProtKB - Q6N021 (TET2_HUMAN)
MEQDRTNHVE GNRLSPFLIP SPPICQTEPL

ATKLQNGSPL PERAHPEVNG

DTKWHSFKSY YGIPCMKGSQ NSRVSPDFTQ

ESRGYSKCLQ NGGIKRTVSE

PSLSGLLQIK KLKQDQKANG ERRNFGVSQE

RNPGESSQPN VSDLSDKKES

VSSVAQENAV KDFTSFSTHN CSGPENPELQ

ILNEQEGKSA NYHDKNIVLL

KNKAVLMPNG ATVSASSVEH THGELLEKTL

SQYYPDCVSI AVQKTTSHIN

AINSQATNEL SCEITHPSHT SGQINSAQTS

NSELPPKPAA VVSEACDADD

ADNASKLAAM LNTCSFQKPE QLQQQKSVFE

ICPSPAENNI QGTTKLASGE

EFCSGSSSNL QAPGGSSERY LKQNEMNGAY

FKQSSVFTKD SFSATTTPPP

PSQLLLSPPP PLPQVPQLPS EGKSTLNGGV

LEEHHHYPNQ SNTTLLREVK

IEGKPEAPPS QSPNPSTHVC SPSPMLSERP

QNNCVNRNDI QTAGTMTVPL

CSEKTRPMSE HLKHNPPIFG SSGELQDNCQ

QLMRNKEQEI LKGRDKEQTR

DLVPPTQHYL KPGWIELKAP RFHQAESHLK

RNEASLPSIL QYQPNLSNQM

TSKQYTGNSN MPGGLPRQAY TQKTTQLEHK

SQMYQVEMNQ GQSQGTVDQH

LQFQKPSHQV HFSKTDHLPK AHVQSLCGTR

FHFQQRADSQ TEKLMSPVLK

QHLNQQASET EPFSNSHLLQ HKPHKQAAQT

QPSQSSHLPQ NQQQQQKLQI

KNKEEILQTF PHPQSNNDQQ REGSFFGQTK

VEECFHGENQ YSKSSEFETH
```

-continued

```
NVQMGLEEVQ NINRRNSPYS QTMKSSACKI

QVSCSNNTHL VSENKEQTTH

PELFAGNKTQ NLHHMQYFPN NVIPKQDLLH

RCFQEQEQKS QQASVLQGYK

NRNQDMSGQQ AAQLAQQRYL IHNHANVFPV

PDQGGSHTQT PPQKDTQKHA

ALRWHLLQKQ EQQQTQQPQT ESCHSQMHRP

IKVEPGCKPH ACMHTAPPEN

KTWKKVTKQE NPPASCDNVQ QKSIIETMEQ

HLKQFHAKSL FDHKALTLKS

QKQVKVEMSG PVTVLTRQTT AAELDSHTPA

LEQQTTSSEK TPTKRTAASV

LNNFIESPSK LLDTPIKNLL DTPVKTQYDF

PSCRCVEQII EKDEGPFYTH

LGAGPNVAAI REIMEERFGQ KGKAIRIERV

IYTGKEGKSS QGCPIAKWVV

RRSSSEEKLL CLVRERAGHT CEAAVIVILI

LVWEGIPLSL ADKLYSELTE

TLRKYGTLTN RRCALNEERT CACQGLDPET

CGASFSFGCS WSMYYNGCKF

ARSKIPRKFK LLGDDPKEEE KLESHLQNLS

TLMAPTYKKL APDAYNNQIE

YEHRAPECRL GLKEGRPFSG VTACLDFCAH

AHRDLHNMQN GSTLVCTLTR

EDNREFGGKP EDEQLHVLPL YKVSDVDEFG

SVEAQEEKKR SGAIQVLSSF

RRKVRMLAEP VKTCRQRKLE AKKAAAEKLS

SLENSSNKNE KEKSAPSRTK

QTENASQAKQ LAELLRLSGP VMQQSQQPQP

LQKQPPQPQQ QQRPQQQQPH

HPQTESVNSY SASGSTNPYM RRPNPVSPYP

NSSHTSDIYG STSPMNFYST

SSQAAGSYLN SSNPMNPYPG LLNQNTQYPS

YQCNGNLSVD NCSPYLGSYS

PQSQPMDLYR YPSQDPLSKL SLPPIHTLYQ

PRFGNSQSFT SKYLGYGNQN

MQGDGFSSCT IRPNVHHVGK LPPYPTHEMD

GHFMGATSRL PPNLSNPNMD

YKNGEHHSPS HIIHNYSAAP GMFNSSLHAL

HLQNKENDML SHTANGLSKM
```

-continued

```
LPALNHDRTA CVQGGLHKLS DANGQEKQPL

ALVQGVASGA EDNDEVWSDS

EQSFLDPDIG GVAVAPTHGS ILIECAKREL

HATTPLKNPN RNHPTRISLV

FYQHKSMNEP KHGLALWEAK MAEKAREKEE

ECEKYGPDYV PQKSHGKKVK

REPAEPHETS EPTYLRFIKS LAERTMSVTT

DSTVTTSPYA FTRVTGPYNR YI,
``` which is specifically incorporated by reference herein in its entirety).

An exemplary human TET1 amino acid sequence:

```
    (SEQ ID NO: 10, UniProtKB - Q8NFU7 (TET1_HUMAN)
MSRSRHARPS RLVRKEDVNK KKKNSQLRKT

TKGANKNVAS VKTLSPGKLK

QLIQERDVKK KTEPKPPVPV RSLLTRAGAA

RMNLDRTEVL FQNPESLTCN

GFTMALRSTS LSRRLSQPPL VVAKSKKVPL

SKGLEKQHDC DYKILPALGV

KHSENDSVPM QDTQVLPDIE TLIGVQNPSL

LKGKSQETTQ FWSQRVEDSK

INIPTHSGPA AEILPGPLEG TRCGEGLFSE

ETLNDTSGSP KMFAQDTVCA

PFPQRATPKV TSQGNPSIQL EELGSRVESL

KLSDSYLDPI KSEHDCYPTS

SLNKVIPDLN LRNCLALGGS TSPTSVIKFL

LAGSKQATLG AKPDHQEAFE

ATANQQEVSD TTSFLGQAFG AIPHQWELPG

ADPVHGEALG ETPDLPEIPG

AIPVQGEVFG TILDQQETLG MSGSVVPDLP

VFLPVPPNPI ATFNAPSKWP

EPQSTVSYGL AVQGAIQILP LGSGHTPQSS

SNSEKNSLPP VMAISNVENE

KQVHISFLPA NTQGFPLAPE RGLFHASLGI

AQLSQAGPSK SDRGSSQVSV

TSTVHVVNTT VVTMPVPMVS TSSSSYTTLL

PTLEKKKRKR CGVCEPCQQK

TNCGECTYCK NRKNSHQICK KRKCEELKKK

PSVVVPLEVI KENKRPQREK

KPKVLKADFD NKPVNGPKSE SMDYSRCGHG

EEQKLELNPH TVENVTKNED

SMTGIEVEKW TQNKKSQLTD HVKGDFSANV
```

-continued

```
PEAEKSKNSE VDKKRTKSPK

LFVQTVRNGI KHVHCLPAET NVSFKKFNIE

EFGKTLENNS YKFLKDTANH

KNAMSSVATD MSCDHLKGRS NVLVFQQPGF

NCSSIPHSSH SIINHHASIH

NEGDQPKTPE NIPSKEPKDG SPVQPSLLSL

MKDRRLTLEQ VVAIEALTQL

SEAPSENSSP SKSEKDEESE QRTASLLNSC

KAILYTVRKD LQDPNLQGEP

PKLNHCPSLE KQSSCNTVVF NGQTTTLSNS

HINSATNQAS TKSHEYSKVT

NSLSLFIPKS NSSKIDTNKS IAQGIITLDN

CSNDLHQLPP RNNEVEYCNQ

LLDSSKKLDS DDLSCQDATH TQIEEDVATQ

LTQLASIIKI NYIKPEDKKV

ESTPTSLVTC NVQQKYNQEK GTIQQKPPSS

VHNNHGSSLT KQKNPTQKKT

KSTPSRDRRK KKPTVVSYQE NDRQKWEKLS

YMYGTICDIW IASKFQNFGQ

FCPHDFPTVF GKISSSTKIW KPLAQTRSIM

QPKTVFPPLT QIKLQRYPES

AEEKVKVEPL DSLSLFHLKT ESNGKAFTDK

AYNSQVQLTV NANQKAHPLT

QPSSPPNQCA NVMAGDDQIR FQQVVKEQLM

HQRLPTLPGI SHETPLPESA

LTLRNVNVVC SGGITVVSTK SEEEVCSSSF

GTSEFSTVDS AQKNFNDYAM

NFFTNPTKNL VSITKDSELP TCSCLDRVIQ

KDKGPYYTHL GAGPSVAAVR

EIMENRYGQK GNAIRIEIVV YTGKEGKSSH

GCPIAKWVLR RSSDEEKVLC

LVRQRTGHHC PTAVMVVLIM VWDGIPLPMA

DRLYTELTEN LKSYNGHPTD

RRCTLNENRT CTCQGIDPET CGASFSFGCS

WSMYFNGCKF GRSPSPRRFR

IDPSSPLHEK NLEDNLQSLA TRLAPIYKQY

APVAYQNQVE YENVARECRL

GSKEGRPFSG VTACLDFCAH PHRDIHNMNN

GSTVVCTLTR EDNRSLGVIP

QDEQLHVLPL YKLSDTDEFG SKEGMEAKIK

SGAIEVLAPR RKKRTCFTQP
```

-continued

```
VPRSGKKRAA MMTEVLAHKI RAVEKKPIPR

IKRKNNSTTT NNSKPSSLPT

LGSNTETVQP EVKSETEPHF ILKSSDNTKT

YSLMPSAPHP VKEASPGFSW

SPKTASATPA PLKNDATASC GFSERSSTPH

CTMPSGRLSG ANAAAADGPG

ISQLGEVAPL PTLSAPVMEP LINSEPSTGV

TEPLTPHQPN HQPSFLTSPQ

DLASSPMEED EQHSEADEPP SDEPLSDDPL

SPAEEKLPHI DEYWSDSEHI

FLDANIGGVA IAPAHGSVLI ECARRELHAT

TPVEHPNRNH PTRLSLVFYQ

HKNLNKPQHG FELNKIKFEA KEAKNKKMKA

SEQKDQAANE GPEQSSEVNE

LNQIPSHKAL TLTHDNVVTV SPYALTHVAG

PYNHWV,
``` which is specifically incorporated by reference herein in its entirety).

2. Isolated Nucleic Acid Molecules

Isolated nucleic acid sequences encoding TET proteins, polypeptides, fusions fragments and variants thereof, and vectors and other expression constructs encoding the foregoing are also disclosed herein. As used herein, "isolated nucleic acid" refers to a nucleic acid that is separated from other nucleic acid molecules that are present in a mammalian genome, including nucleic acids that normally flank one or both sides of the nucleic acid in a mammalian genome (e.g., nucleic acids that encode non-TET proteins). The term "isolated" as used herein with respect to nucleic acids also includes the combination with any non-naturally-occurring nucleic acid sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule independent of other sequences (e.g., a chemically synthesized nucleic acid, or a cDNA or genomic DNA fragment produced by PCR or restriction endonuclease treatment), as well as recombinant DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, a cDNA library or a genomic library, or a gel slice containing a genomic DNA restriction digest, is not to be considered an isolated nucleic acid.

The nucleic acid sequences encoding TET polypeptides include genomic sequences. Also disclosed are mRNA sequences wherein the exons have been deleted. Other nucleic acid sequences encoding TET polypeptides, such polypeptides that include the above-identified amino acid sequences and fragments and variants thereof, are also disclosed. Nucleic acids encoding TET polypeptides may be optimized for expression in the expression host of choice. Codons may be substituted with alternative codons encoding the same amino acid to account for differences in codon usage between the organism from which the TET nucleic acid sequence is derived and the expression host. In this manner, the nucleic acids may be synthesized using expression host-preferred codons.

Nucleic acids can be in sense or antisense orientation, or can be complementary to a reference sequence encoding a TET polypeptide. Nucleic acids can be DNA, RNA, or nucleic acid analogs. Nucleic acid analogs can be modified at the base moiety, sugar moiety, or phosphate backbone. Such modification can improve, for example, stability, hybridization, or solubility of the nucleic acid. Common modifications are discussed in more detail below.

Nucleic acids encoding polypeptides can be administered to subjects in need thereof. Nucleic delivery involves introduction of "foreign" nucleic acids into a cell and ultimately, into a live animal. Compositions and methods for delivering nucleic acids to a subject are known in the art (see Understanding Gene Therapy, Lemoine, N. R., ed., BIOS Scientific Publishers, Oxford, 2008).

a. Vectors and Host Cells

Vectors encoding TET polypeptides, and fusion proteins, fragments, and variants thereof are also provided. Nucleic acids, such as those described above, can be inserted into vectors for expression in cells. As used herein, a "vector" is a replicon, such as a plasmid, phage, virus or cosmid, into which another DNA segment may be inserted so as to bring about the replication of the inserted segment. Vectors can be expression vectors. An "expression vector" is a vector that includes one or more expression control sequences, and an "expression control sequence" is a DNA sequence that controls and regulates the transcription and/or translation of another DNA sequence.

Nucleic acids in vectors can be operably linked to one or more expression control sequences. For example, the control sequence can be incorporated into a genetic construct so that expression control sequences effectively control expression of a coding sequence of interest. Examples of expression control sequences include promoters, enhancers, and transcription terminating regions. A promoter is an expression control sequence composed of a region of a DNA molecule, typically within 100 nucleotides upstream of the point at which transcription starts (generally near the initiation site for RNA polymerase II). To bring a coding sequence under the control of a promoter, it is necessary to position the translation initiation site of the translational reading frame of the polypeptide between one and about fifty nucleotides downstream of the promoter. Enhancers provide expression specificity in terms of time, location, and level. Unlike promoters, enhancers can function when located at various distances from the transcription site. An enhancer also can be located downstream from the transcription initiation site. A coding sequence is "operably linked" and "under the control" of expression control sequences in a cell when RNA polymerase is able to transcribe the coding sequence into mRNA, which then can be translated into the protein encoded by the coding sequence.

Suitable expression vectors include, without limitation, plasmids and viral vectors derived from, for example, bacteriophage, baculoviruses, tobacco mosaic virus, herpes viruses, cytomegalo virus, retroviruses, vaccinia viruses, adenoviruses, and adeno-associated viruses. Numerous vectors and expression systems are commercially available from such corporations as Novagen (Madison, WI), Clontech (Palo Alto, CA), Stratagene (La Jolla, CA), and Invitrogen Life Technologies (Carlsbad, CA).

An expression vector can include a tag sequence. Tag sequences are typically expressed as a fusion with the encoded polypeptide. Such tags can be inserted anywhere within the polypeptide including at either the carboxyl or amino terminus. Examples of useful tags include, but are not limited to, green fluorescent protein (GFP), glutathione S-transferase (GST), polyhistidine, c-myc, hemagglutinin, Flag™ tag (Kodak, New Haven, CT), maltose E binding protein and protein A.

Vectors containing nucleic acids to be expressed can be transferred into host cells. The term "host cell" is intended to include prokaryotic and eukaryotic cells into which a recombinant expression vector can be introduced. As used herein, "transformed" and "transfected" encompass the introduction of a nucleic acid molecule (e.g., a vector) into a cell by one of a number of techniques. Although not limited to a particular technique, a number of these techniques are well established within the art. Prokaryotic cells can be transformed with nucleic acids by, for example, electroporation or calcium chloride mediated transformation. Nucleic acids can be transfected into mammalian cells by techniques including, for example, calcium phosphate co-precipitation, DEAE-dextran-mediated transfection, lipofection, electroporation, or microinjection. Host cells (e.g., a prokaryotic cell or a eukaryotic cell such as a CHO cell) can be used to, for example, produce the TET polypeptides or fusion polypeptides described herein.

The vectors can be used to express TET in cells. An exemplary vector includes, but is not limited to, an adenoviral vector. One approach includes nucleic acid transfer into primary cells in culture followed by autologous transplantation of the ex vivo transformed cells into the host, either systemically or into a particular organ or tissue. Ex vivo methods can include, for example, the steps of harvesting cells from a subject, culturing the cells, transducing them with an expression vector, and maintaining the cells under conditions suitable for expression of the encoded polypeptides. These methods are known in the art of molecular biology. The transduction step can be accomplished by any standard means used for ex vivo gene therapy, including, for example, calcium phosphate, lipofection, electroporation, viral infection, and biolistic gene transfer. Alternatively, liposomes or polymeric microparticles can be used. Cells that have been successfully transduced then can be selected, for example, for expression of the coding sequence or of a drug resistance gene. The cells then can be lethally irradiated (if desired) and injected or implanted into the subject. In one embodiment, expression vectors containing nucleic acids encoding fusion proteins are transfected into cells that are administered to a subject in need thereof.

Nucleic acid molecules encoding polypeptides or fusion proteins may be packaged into retrovirus vectors using packaging cell lines that produce replication-defective retroviruses, as is well-known in the art. Other virus vectors may also be used, including recombinant adenoviruses and vaccinia virus, which can be rendered non-replicating. In addition to naked DNA or RNA, or viral vectors, engineered bacteria may be used as vectors.

Nucleic acids may also be delivered by other carriers, including liposomes, polymeric micro- and nanoparticles and polycations such as asialoglycoprotein/polylysine.

Physical means well-known in the art can be used for direct transfer of DNA, including administration of plasmid DNA and particle-bombardment mediated gene transfer.

b. Oligonucleotide Composition

The disclosed nucleic acids nucleic acids can be DNA or RNA nucleotides which typically include a heterocyclic base (nucleic acid base), a sugar moiety attached to the heterocyclic base, and a phosphate moiety which esterifies a hydroxyl function of the sugar moiety. The principal naturally-occurring nucleotides include uracil, thymine, cytosine, adenine and guanine as the heterocyclic bases, and ribose or deoxyribose sugar linked by phosphodiester bonds.

In some embodiments, the oligonucleotides are composed of nucleotide analogs that have been chemically modified to improve stability, half-life, or specificity or affinity for a target receptor, relative to a DNA or RNA counterpart. The chemical modifications include chemical modification of nucleobases, sugar moieties, nucleotide linkages, or combinations thereof. As used herein 'modified nucleotide" or "chemically modified nucleotide" defines a nucleotide that has a chemical modification of one or more of the heterocyclic base, sugar moiety or phosphate moiety constituents. In some embodiments, the charge of the modified nucleotide is reduced compared to DNA or RNA oligonucleotides of the same nucleobase sequence. For example, the oligonucleotide can have low negative charge, no charge, or positive charge.

Typically, nucleoside analogs support bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). In some embodiments, the analogs have a substantially uncharged, phosphorus containing backbone.

i. Heterocyclic Bases

The principal naturally-occurring nucleotides include uracil, thymine, cytosine, adenine and guanine as the heterocyclic bases. The oligonucleotides can include chemical modifications to their nucleobase constituents. Chemical modifications of heterocyclic bases or heterocyclic base analogs may be effective to increase the binding affinity or stability in binding a target sequence. Chemically-modified heterocyclic bases include, but are not limited to, inosine, 5-(1-propynyl) uracil (pU), 5-(1-propynyl) cytosine (pC), 5-methylcytosine, 8-oxo-adenine, pseudocytosine, pseudoisocytosine, 5 and 2-amino-5-(2'-deoxy-.beta.-D-ribofuranosyl)pyridine (2-aminopyridine), and various pyrrolo- and pyrazolopyrimidine derivatives.

ii. Sugar Modifications

Oligonucleotides can also contain nucleotides with modified sugar moieties or sugar moiety analogs. Sugar moiety modifications include, but are not limited to, 2'-O-aminoetoxy, 2'-O-amonioethyl (2'-OAE), 2'-O-methoxy, 2'-O-methyl, 2-guanidoethyl (2'-OGE), 2'-O,4'-C-methylene (LNA), 2'-O-(methoxyethyl) (2'-OME) and 2'-O—(N-(methyl)acetamido) (2'-OMA). 2'-O-aminoethyl sugar moiety substitutions are especially preferred because they are protonated at neutral pH and thus suppress the charge repulsion between the TFO and the target duplex. This modification stabilizes the C3'-endo conformation of the ribose or dexyribose and also forms a bridge with the i–1 phosphate in the purine strand of the duplex.

In some embodiments, the nucleic acid is a morpholino oligonucleotide. Morpholino oligonucleotides are typically composed of two more morpholino monomers containing purine or pyrimidine base-pairing moieties effective to bind, by base-specific hydrogen bonding, to a base in a polynucleotide, which are linked together by phosphorus-containing linkages, one to three atoms long, joining the morpholino nitrogen of one monomer to the 5' exocyclic carbon of an adjacent monomer. The purine or pyrimidine base-pairing moiety is typically adenine, cytosine, guanine, uracil or thymine. The synthesis, structures, and binding characteristics of morpholino oligomers are detailed in U.S. Pat. Nos. 5,698,685, 5,217,866, 5,142,047, 5,034,506, 5,166,315, 5,521,063, and 5,506,337.

Important properties of the morpholino-based subunits typically include: the ability to be linked in a oligomeric form by stable, uncharged backbone linkages; the ability to support a nucleotide base (e.g. adenine, cytosine, guanine, thymidine, uracil or inosine) such that the polymer formed can hybridize with a complementary-base target nucleic acid, including target RNA, with high $T_m$, even with oligomers as short as 10-14 bases; the ability of the oligomer to be actively transported into mammalian cells; and the ability of an oligomer:RNA heteroduplex to resist RNAse degradation.

In some embodiments, oligonucleotides employ morpholino-based subunits bearing base-pairing moieties, joined by uncharged linkages, as described above.

iii. Internucleotide Linkages

Oligonucleotides connected by an internucleotide bond that refers to a chemical linkage between two nucleoside moieties. Modifications to the phosphate backbone of DNA or RNA oligonucleotides may increase the binding affinity or stability oligonucleotides, or reduce the susceptibility of oligonucleotides nuclease digestion. Cationic modifications, including, but not limited to, diethyl-ethylenediamide (DEED) or dimethyl-aminopropylamine (DMAP) may be especially useful due to decrease electrostatic repulsion between the oligonucleotide and a target. Modifications of the phosphate backbone may also include the substitution of a sulfur atom for one of the non-bridging oxygens in the phosphodiester linkage. This substitution creates a phosphorothioate internucleoside linkage in place of the phosphodiester linkage. Oligonucleotides containing phosphorothioate internucleoside linkages have been shown to be more stable in vivo.

Examples of modified nucleotides with reduced charge include modified internucleotide linkages such as phosphate analogs having achiral and uncharged intersubunit linkages (e.g., Sterchak, E. P. et al., Organic. Chem., 52:4202, (1987)), and uncharged morpholino-based polymers having achiral intersubunit linkages (see, e.g., U.S. Pat. No. 5,034, 506), as discussed above. Some internucleotide linkage analogs include morpholidate, acetal, and polyamide-linked heterocycles.

In another embodiment, the oligonucleotides are composed of locked nucleic acids. Locked nucleic acids (LNA) are modified RNA nucleotides (see, for example, Braasch, et al., Chem. Biol., 8(1):1-7 (2001)). LNAs form hybrids with DNA which are more stable than DNA/DNA hybrids, a property similar to that of peptide nucleic acid (PNA)/DNA hybrids. Therefore, LNA can be used just as PNA molecules would be. LNA binding efficiency can be increased in some embodiments by adding positive charges to it. Commercial nucleic acid synthesizers and standard phosphoramidite chemistry are used to make LNAs.

In some embodiments, the oligonucleotides are composed of peptide nucleic acids. Peptide nucleic acids (PNAs) are synthetic DNA mimics in which the phosphate backbone of the oligonucleotide is replaced in its entirety by repeating N-(2-aminoethyl)-glycine units and phosphodiester bonds are typically replaced by peptide bonds. The various heterocyclic bases are linked to the backbone by methylene carbonyl bonds. PNAs maintain spacing of heterocyclic bases that is similar to conventional DNA oligonucleotides, but are achiral and neutrally charged molecules. Peptide nucleic acids are composed of peptide nucleic acid monomers.

Other backbone modifications include peptide and amino acid variations and modifications. Thus, the backbone constituents of oligonucleotides such as PNA may be peptide linkages, or alternatively, they may be non-peptide peptide linkages. Examples include acetyl caps, amino spacers such as 8-amino-3,6-dioxaoctanoic acid (referred to herein as O-linkers), amino acids such as lysine are particularly useful if positive charges are desired in the PNA, and the like. Methods for the chemical assembly of PNAs are well known. See, for example, U.S. Pat. Nos. 5,539,082, 5,527, 675, 5,623,049, 5,714,331, 5,736,336, 5,773,571 and 5,786, 571.

Oligonucleotides optionally include one or more terminal residues or modifications at either or both termini to increase stability, and/or affinity of the oligonucleotide for its target. Commonly used positively charged moieties include the amino acids lysine and arginine, although other positively charged moieties may also be useful. Oligonucleotides may further be modified to be end capped to prevent degradation using a propylamine group. Procedures for 3' or 5' capping oligonucleotides are well known in the art.

In some embodiments, the nucleic acid can be single stranded or double stranded.

C. Methods of Treatment

The disclosed methods typically include injecting or otherwise delivering a compound that increases TET bioavailability into a male gamete preferably, spermatids or haploid spermatogenic cells, oocyte, fertilized egg, or early stage embryo. In some embodiments, the compound is delivered in combination with a male gamete during, for example, intracytoplasmic sperm injection (ICSI). Thus, as used herein, ICSI refers to intracytoplasmic injection of not only sperm, but additionally or alternatively spermatids and other male gametes.

Methods for ICSI are known in the art. ICSI is an in vitro fertilization (IVF) procedure in which a single male gamete is injected directly into the cytoplasm of an egg. ICSI needs only one male gamete per oocyte, while IVF typically utilizes more than fifty thousand. By delivering the male gamete directly into the oocyte, ICSI avoids the acrosome reaction-mediated sperm entry into an oocyte that typically needs thousands of sperm.

ICSI typically utilizes a laminar flow cabinet, inverted microscope, micromanipulators, microinjectors and anti-vibration table. The procedure is done under a microscope using multiple micromanipulation devices (micromanipulator, microinjectors and micropipettes). A holding pipette stabilizes the mature oocyte with gentle suction applied by a microinjector. The microinjector is typically a hermetic syringe filled with mineral oil, controlled by micromanipulators, and connected to the microinjection pipettes (to aspirate and inject the spermatozoa) by a flexible tube.

From the opposite side a thin, hollow glass micropipette is used to collect a single sperm by applying negative pressure using a microinjector. The sperm has typically been immobilized by pressing its tail with the point of the micropipette. The oocyte is pierced through the oolemma and the sperm is delivered into the cytoplasm of the oocyte. Preferably, the polar body is positioned at the 12 or 6 o'clock position, to ensure that the inserted micropipette does not disrupt the spindle inside the egg. Next, the oocyte is cultured and checked on the following day for signs of fertilization. The method optionally includes an activation step using sperm extract and chemical activation. Sperm extract is co-injected with Tet3 and haploid round spermatids fuding ICSI. Following ICSI, reconstructed oocytes are activated by culturing five minutes in 5 UM ionomycin in TALP-Hepes medium, followed by incubation in 2 mM 6-Dimethylaminopurine (6-DMAP) in HECM-9 for five hours in a humidified atmosphere of 5% $CO_2$, 5% $O_2$ and 90% $N_2$ at 37° C.

In additional or alternative to microinjection, electroporation can be used to deliver TET proteins and/or nucleic acids (e.g., TET3 protein or nucleic acids) into oocyte. In some embodiments, this method of delivering TET constructs is used in combination with classical IVF. Thus, in some embodiments, the procedure can be carried out without an injection step, reducing mechanical damage during the procedure.

The procedure before and after insemination by classical IVF and ICSI are generally the same. For example, once fertilized, the egg is transformed into a proembryo, cultured for about 2-6 days, and transferred to the uterus.

Although compounds for increasing TET bioavailability are particularly advantageous for use with an ICSI-based gamete delivery, the disclosed methods can also be used in combination with classical IVF procedures. In such embodiments, the compound for increasing TET bioavailability may be delivered to the oocyte before or after classical in vitro fertilization, (e.g., before or after the egg is contacted with sperm). In other embodiments, the compound for increasing TET bioavailability may be delivered to a male gamete such as spermatids or haploid spermatogenic cells prior to ICSI or IVF.

Live birth rates are significantly higher with progesterone to assist implantation in ICSI cycles. Also, addition of a GNRH agonist has been estimated to increase success rates. Thus, theses additional compositions and methods can be included in the treatment.

Additionally or alternatively, in some embodiments, the method includes ultra-high magnification sperm injection (IMSI). IMSI includes a selection step referred to as motile sperm organelle morphology examination (MSOME) and the spermatozoa are selected under high magnification (over 6000×) prior to ICSI.

Sperm selection for ICSI can also include testing for binding to hyaluronan, the main constituent of the gel layer (*Cumulus oophorus*) surrounding the oocyte. In an exemplary method, a device (e.g., a PICSI® device) provides microscopic droplets of hyaluronan hydrogel attached to the culture dish. The practitioner places the prepared sperm on the microdot, selects and captures sperm that bind to the dot. Basic research on the maturation of sperm shows that hyaluronan-binding sperm are more mature and show fewer DNA strand breaks and significantly lower levels of aneuploidy than the sperm population from which they were selected.

In some embodiments, the gametes are treated with the compound during differentiation, for example in vitro differentiation.

The disclosed compounds are typically administered into the gamete or embryo in a carrier, preferably a pharmaceutically acceptable carrier. In a preferred embodiment, the compositions are suspended in a suitable sperm extract buffer suitable for injection into oocytes (Simerly et al., (2003) *Cloning and Stem Cells* 5(4) 319-331; Swann (1990) *Development* 110, 1295-1302; Stice et al., (1988) *Biol Reprod* 39,657-664), for example, KCL (Sigma P4505), HEPES (Sigma H6147), EGTA (Sigma E3889), and sodium glycerophoaste (Sigma G-5422). An exemplary buffer formulation is shown in the Table 2.

D. Sources of Gametes

Female gametes are called ova, oocytes, or egg cells. Male gametes are called sperm, however it will be appreciated that male gametes as used herein include both mature sperm, and immature sperm, for example, round spermatids, elongating spermatids, condensing spermatids, or condensed spermatids. Gametes are haploid cells, and each cell carries only one copy of each chromosome.

Like classical IVF, ICSI is generally performed following a transvaginal oocyte retrieval procedure to extract one to several oocytes from a woman or laporascopic aspiration in nonhuman primates. Additional techniques that are routinely used in IVF, and thus can be included as part of the disclosed methods, include ovarian hyperstimulation to generate multiple eggs or ultrasound-guided transvaginal oocyte retrieval directly from the ovaries; after which the ova and sperm are prepared, as well as culture and selection of resultant embryos before embryo transfer into a uterus.

Male gametes for use in the disclosed methods can be obtained in a variety of ways. Sperm can be isolated from a donor subject. For example, a male partner or a donor can provide a sperm sample (e.g., on the same day when the eggs are collected). If no sperm is present in the sample, doctors can extract sperm from the epididymis or testicle. The extraction of sperm from epididymides is also known as percutaneous epididymal sperm aspiration (PESA) and extraction of sperm from testicles is also known as testicular sperm aspiration (TESA).

Many infertile men produce immature spermatids (round spermatids) in their testes. Testis biopsies are standard procedures for obtaining immature spermatids, but the success rates of fertilizing their partner's eggs is typically extremely low. However, it is believed that increasing TET bioavailability will improve fertilize rates and/or viable embryos derived therefrom. Thus, in some embodiments, the male gametes are immature spermatids.

Furthermore, human and non-human primate embryonic (ESCs) and induced pluripotent stem cells (iPSCs) can be induced to differentiate directly into advanced male germ cell lineages including post-meiotic, spermatid-like cells in vitro without genetic manipulation. Such methods are discussed in more detail below.

III. Methods of Making Gametes

Methods of making male gametes in vitro are also provided. The methods can be used alone or in combination with the disclosed methods of increasing TET bioavailability and/or correcting genomic mutations.

Human and non-human primate embryonic (ESCs) and induced pluripotent stem cells (iPSCs) can be induced to differentiate directly into advanced male germ cell lineages. See, e.g., the working Examples below and Easley I V, et al., *Cell Rep.* 2(3): 440-446 (2012) doi: 10.1016/j.celrep.2012.07.015, which along with all of its supplementary material, is specifically incorporated by reference in its entirety. The Examples below show that such spermatid-like cells can be used as a source of male gametes for ICSI, which leads to a fertilized egg and subsequent development through the blastocyst stage.

Briefly, Easley IV, supra, describes that ESCs and iPSCs can be differentiated into spermatid-like cells over 10 days in mouse spermatogonial stem cell (SSC) medium which generally contains some or all of the following: MEMalpha, Bovine Serum Albumin, insulin, transferrin, putrescine, L-glutamine, β-mercaptoethanol, hbFGF (human basic fibroblast growth factor), 20 ng/ml GDNF (glial-derived neurotrophic factor), sodium selenite, palmitic acid, palmitoleic acid, stearic acid, oleic acid, linoleic acid, linolenic acid, HEPES, and penicillin/streptomycin. Spermatid-like cells can be selected from other cells (e.g., undifferentiated), using FACS, morphological analysis, marker expression, or a combination thereof. Post-meiotic, sperm markers include, for example, acrosin, protamine 1, and transition protein 1.

In some preferred embodiments, the culture conditions for differentiation do not include feeder cells for example, mouse STO feeder cells. Preferably, ESCs/iPSCs cells are cultured in hESC conditions for 2-5 days prior to culturing in differentiation medium. In order to compile with Good Manufacturing Practice (GMP), all animal derived products and cells need to be eliminated for clinical application. Therefore, a differentiation protocol which does not rely on the support of the STO feeder cells is highly desirable.

Source of ESCs and iPSCs are known in the art. For example, embryonic stem cells are generally derived from embryos that are three to five days old. Any somatic cell may a source for reprogramming into an iPSC. Preferred sources and basic methods of reprogramming are known in the art, see, e.g., Raab, et al., Stem Cells International, Volume 2014, Article ID 768391, 12 pages, (2014) doi: 10.1155/2014/768391. Exemplary sources include, but are not limited to, fibroblasts, the most commonly used primary somatic cell type for the generation of induced pluripotent stem cells, as well as peripheral blood, umbilical cord blood, cells from urine, multipotent stem cells, cells of hematological origin, cells of embryonic origin, skin derived cells, adipose cells, epithelial cells, endothelial cells, parenchymal cells, neurological cells, and connective tissue. Specific examples include exfoliated renal epithelial cells, keratinocytes, stratified squamous epithelium, multipotent mesenchymal stem cells (MSCs), hepatocytes, synovial cells, mesenchymal stromal cells, adult stem cells, and amniotic epithelial cells.

There are certain infertile male patients who do not produce any gametes but possess spermatogonia stem cells, which are stem cells that in normal patients produce sperm after puberty. For these patients, spermatogonial stem cells can be isolated from their testis tissue and differentiated as disclosed herein to produce spermatids.

IV. Methods of Correcting Mutations

Compositions and methods of correcting genomic mutations are also provided for use alone or in combination with other compositions and methods disclosed herein. Some embodiments include steps of correcting mutations or otherwise modifying the genome of male gamete progenitor cells before they are differentiated into spermatids. For example, in some embodiments somatic cells such as ESCs, iPSCs, or iPSCs source cells (e.g., fibroblasts, etc.) prior to reprogramming can be subjected to a genome editing. Generally, the cells are contacted (e.g., transformed) with an effective amount of a gene editing composition ex vivo to induce a specific genomic modification therein.

Advantageously, the cells can be screened for targeted genetic modification prior to differentiation to spermatids. For example, PCR, whole genome sequencing, or other art-recognized methods can be used to analyze the genetically modified cells prior to the creation of spermatids or embryos to ensure to precise genetics of offspring prior to clinical use. The resulting embryos and offspring are constituted by parental genome contributed through male and female germ cells, thus all resulting offspring will not be a mosaic.

In some embodiments, a fertilized egg or early stage embryo (e.g., a blastocyte) is contacted (e.g, transformed, injected, etc.) with an effective amount of a gene editing composition ex vivo to induce a specific genomic modification therein. In some embodiments, the gene editing composition is delivered to the oocyte in combination with the male gamete and optionally in further combination with a compound that increases TET bioavailability (e.g., by injection during ICSI).

A. Gene Editing Compositions

Gene editing compositions can include nucleic acids that encode an element or elements that induce a single or a double strand break in the target cell's genome, and optionally a polynucleotide. The compositions can be used, for example, to correct disease causing mutations including, but not limited to, those described below.

1. Strand Break Inducing Elements a. CRISPR/Cas

In some embodiments, the element that induces a single or a double strand break in the target cell's genome is a CRISPR/Cas system. CRISPR (Clustered Regularly Interspaced Short Palindromic Repeats) is an acronym for DNA loci that contain multiple, short, direct repetitions of base sequences. The prokaryotic CRISPR/Cas system has been adapted for use as gene editing (silencing, enhancing or changing specific genes) for use in eukaryotes (see, for example, Cong, *Science,* 15:339(6121):819-823 (2013) and Jinek, et al., *Science,* 337(6096):816-21 (2012)). By transfecting a cell with the required elements including a Cas gene and specifically designed CRISPRs, the organism's genome can be cut and modified at any desired location. Methods of preparing compositions for use in genome editing using the CRISPR/Cas systems are described in detail in WO 2013/176772 and WO 2014/018423, which are specifically incorporated by reference herein in their entireties.

In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. One or more tracr mate sequences operably linked to a guide sequence (e.g., direct repeat-spacer-direct repeat) can also be referred to as pre-crRNA (pre-CRISPR RNA) before processing or crRNA after processing by a nuclease.

In some embodiments, a tracrRNA and crRNA are linked and form a chimeric crRNA-tracrRNA hybrid where a mature crRNA is fused to a partial tracrRNA via a synthetic stem loop to mimic the natural crRNA:tracrRNA duplex as described in Cong, *Science,* 15:339(6121):819-823 (2013) and Jinek, et al., *Science,* 337(6096):816-21 (2012)). A single fused crRNA-tracrRNA construct can also be referred to as a guide RNA or gRNA (or single-guide RNA (sgRNA)). Within an sgRNA, the crRNA portion can be identified as the 'target sequence' and the tracrRNA is often referred to as the 'scaffold'.

In some embodiments, one or more elements of a CRISPR system is derived from a type I, type II, or type III CRISPR system. In some embodiments, one or more elements of a CRISPR system is derived from a particular organism including an endogenous CRISPR system, such as *Streptococcus pyogenes.*

In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. A target sequence can be any polynucleotide, such as DNA or RNA polynucleotides. In some embodiments, a target sequence is located in the nucleus or cytoplasm of a cell.

In the target nucleic acid, each protospacer is associated with a protospacer adjacent motif (PAM) whose recognition is specific to individual CRISPR systems. In the *Streptococcus pyogenes* CRISPR/Cas system, the PAM is the nucleotide sequence NGG. In the *Streptococcus thermophiles* CRISPR/Cas system, the PAM is the nucleotide sequence is NNAGAAW. The tracrRNA duplex directs Cas to the DNA target consisting of the protospacer and the requisite PAM via heteroduplex formation between the spacer region of the crRNA and the protospacer DNA.

Typically, in the context of an endogenous CRISPR system, formation of a CRISPR complex (including a guide sequence hybridized to a target sequence and complexed with one or more Cas proteins) results in cleavage of one or both strands in or near (e.g., within 1, 2, 3, 4, 5, 6, 7, 8, 9, 10, 20, 50, or more base pairs from) the target sequence. All or a portion of the tracr sequence may also form part of a CRISPR complex, such as by hybridization to all or a portion of a tracr mate sequence that is operably linked to the guide sequence.

There are many resources available for helping practitioners determine suitable target sites once a desired DNA target sequence is identified. For example, numerous public resources, including a bioinformatically generated list of about 190,000 potential sgRNAs, targeting more than 40% of human exons, are available to aid practitioners in selecting target sites and designing the associate sgRNA to affect a nick or double strand break at the site. See also, crispr.u-psud.fr/, a tool designed to help scientists find CRISPR targeting sites in a wide range of species and generate the appropriate crRNA sequences.

In some embodiments, one or more vectors driving expression of one or more elements of a CRISPR system are introduced into a target cell such that expression of the elements of the CRISPR system direct formation of a CRISPR complex at one or more target sites.

For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element can be located on the same or opposite strand of the coding sequence of a second element, and oriented in the same or opposite direction. In some embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g., each in a different intron, two or more in at least one intron, or all in a single intron). In some embodiments, the CRISPR enzyme, guide sequence, tracr mate sequence, and tracr sequence are operably linked to and expressed from the same promoter.

In some embodiments, a vector includes one or more insertion sites, such as a restriction endonuclease recognition sequence (also referred to as a "cloning site"). In some embodiments, one or more insertion sites (e.g., about or more than about 1, 2, 3, 4, 5, 6, 7, 8, 9, 10, or more insertion sites) are located upstream and/or downstream of one or more sequence elements of one or more vectors. In some embodiments, a vector includes an insertion site upstream of a tracr mate sequence, and optionally downstream of a regulatory element operably linked to the tracr mate sequence, such that following insertion of a guide sequence into the insertion site and upon expression the guide sequence directs sequence-specific binding of a CRISPR complex to a target sequence in a eukaryotic cell. In some embodiments, a vector includes two or more insertion sites, each insertion site being located between two tracr mate sequences so as to allow insertion of a guide sequence at each site. In such an arrangement, the two or more guide sequences can include two or more copies of a single guide sequence, two or more different guide sequences, or combinations of these. When multiple different guide sequences are used, a single expression construct may be used to target CRISPR activity to multiple different, corresponding target sequences within a cell. For example, a single vector can include about or more than about 1, 2, 3, 4, 5, 6, 7, 8, 9, 10, 15, 20 guide sequences. In some embodiments, about or more than about 1, 2, 3, 4, 5, 6, 7, 8, 9, 10, such guide-sequence-containing vectors may be provided, and optionally delivered to a cell.

In some embodiments, a vector includes a regulatory element operably linked to an enzyme-coding sequence encoding a CRISPR enzyme, such as a Cas protein.

Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. In some embodiments, the unmodified CRISPR enzyme has DNA cleavage activity, such as Cas9. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence.

In some embodiments, a vector encodes a CRISPR enzyme that is mutated with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. As a further example, two or more catalytic domains of Cas9 (RuvC I, RuvC II, and RuvC III) can be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a CRISPR enzyme is considered to substantially lack all DNA cleavage activity when the DNA cleavage activity of the mutated enzyme is less than about 25%, 10%, 5%>, 1%>, 0.1%>, 0.01%, or lower with respect to its non-mutated form.

In some embodiments, an enzyme coding sequence encoding a CRISPR enzyme is codon optimized for expression in particular cells, such as eukaryotic cells. The eukaryotic cells can be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules.

The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database", and these tables can be adapted in a number of ways. See Nakamura, Y., et al., *Nucl. Acids Res.,* 28:292 (2000). Computer algorithms for codon optimizing a particular sequence for expression in a particular host cell, for example Gene Forge (Aptagen; Jacobus, PA), are also available. In some embodiments, one or more codons (e.g., 1, 2, 3, 4, 5, 10, 15, 20, 25, 50, or more, or all codons) in a sequence encoding a CRISPR enzyme correspond to the most frequently used codon for a particular amino acid.

In some embodiments, a vector encodes a CRISPR enzyme including one or more nuclear localization sequences (NLSs). When more than one NLS is present, each may be selected independently of the others, such that a single NLS may be present in more than one copy and/or in combination with one or more other NLSs present in one or more copies. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus.

In general, the one or more NLSs are of sufficient strength to drive accumulation of the CRISPR enzyme in a detectable amount in the nucleus of a eukaryotic cell. In general, strength of nuclear localization activity may derive from the number of NLSs in the CRISPR enzyme, the particular NLS(s) used, or a combination of these factors.

Detection of accumulation in the nucleus may be performed by any suitable technique. For example, a detectable marker may be fused to the CRISPR enzyme, such that location within a cell may be visualized, such as in combination with a means for detecting the location of the nucleus (e.g., a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g., assay for DNA cleavage or mutation at the target sequence, or assay for altered gene expression activity affected by CRISPR complex formation and/or CRISPR enzyme activity), as compared to a control no exposed to the CRISPR enzyme or complex, or exposed to a CRISPR enzyme lacking the one or more NLSs.

In some embodiments, one or more of the elements of CRISPR system are under the control of an inducible promoter, which can include inducible Cas, such as Cas9.

Cong, *Science,* 15:339(6121):819-823 (2013) reported heterologous expression of Cas9, tracrRNA, pre-crRNA (or Cas9 and sgRNA) can achieve targeted cleavage of mammalian chromosomes. Therefore, CRISPR system utilized in the methods disclosed herein can be encoded within a vector system which can include one or more vectors which can include a first regulatory element operably linked to a CRISPR/Cas system chimeric RNA (chiRNA) polynucleotide sequence, wherein the polynucleotide sequence includes (a) a guide sequence capable of hybridizing to a target sequence in a eukaryotic cell, (b) a tracr mate sequence, and (c) a tracr sequence; and a second regulatory element operably linked to an enzyme-coding sequence encoding a CRISPR enzyme which can optionally include at least one or more nuclear localization sequences. Elements (a), (b) and (c) can arranged in a 5' to 3 orientation, wherein components I and II are located on the same or different vectors of the system, wherein when transcribed, the tracr mate sequence hybridizes to the tracr sequence and the guide sequence directs sequence-specific binding of a CRISPR complex to the target sequence, and wherein the CRISPR complex can include the CRISPR enzyme complexed with (1) the guide sequence that is hybridized to the target sequence, and (2) the tracr mate sequence that is hybridized to the tracr sequence, wherein the enzyme coding sequence encoding the CRISPR enzyme further encodes a heterologous functional domain. In some embodiment, one or more of the vectors encodes also encodes a suitable Cas enzyme, for example, Cas9. The different genetic elements can be under the control of the same or different promoters.

While the specifics can be varied in different engineered CRISPR systems, the overall methodology is similar. A practitioner interested in using CRISPR technology to target a DNA sequence can insert a short DNA fragment containing the target sequence into a guide RNA expression plasmid. The sgRNA expression plasmid contains the target sequence (about 20 nucleotides), a form of the tracrRNA sequence (the scaffold) as well as a suitable promoter and necessary elements for proper processing in eukaryotic cells. Such vectors are commercially available (see, for example, Addgene). Many of the systems rely on custom, complementary oligos that are annealed to form a double stranded DNA and then cloned into the sgRNA expression plasmid. Co-expression of the sgRNA and the appropriate Cas enzyme from the same or separate plasmids in transfected cells results in a single or double strand break (depending of the activity of the Cas enzyme) at the desired target site.

b. Zinc Finger Nucleases

In some embodiments, the element that induces a single or a double strand break in the target cell's genome is a nucleic acid construct or constructs encoding a zinc finger nucleases (ZFNs). ZFNs are typically fusion proteins that include a DNA-binding domain derived from a zinc-finger protein linked to a cleavage domain.

The most common cleavage domain is the Type IIS enzyme Fok1. Fok1 catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487, 994; as well as Li et al. *Proc., Natl. Acad. Sci. USA* 89 (1992):4275-4279; Li et al. *Proc. Natl. Acad. Sci. USA,* 90:2764-2768 (1993); Kim et al. *Proc. Natl. Acad. Sci. USA.* 91:883-887 (1994a); Kim et al. *J. Biol. Chem.* 269:31,978-31,982 (1994b). One or more of these enzymes (or enzymatically functional fragments thereof) can be used as a source of cleavage domains.

The DNA-binding domain, which can, in principle, be designed to target any genomic location of interest, can be a tandem array of $Cys_2His_2$ zinc fingers, each of which generally recognizes three to four nucleotides in the target DNA sequence. The $Cys_2His_2$ domain has a general structure: Phe (sometimes Tyr)-Cys-(2 to 4 amino acids)-Cys-(3 amino acids)-Phe (sometimes Tyr)-(5 amino acids)-Leu-(2 amino acids)-His-(3 amino acids)-His. By linking together multiple fingers (the number varies: three to six fingers have been used per monomer in published studies), ZFN pairs can be designed to bind to genomic sequences 18-36 nucleotides long.

Engineering methods include, but are not limited to, rational design and various types of empirical selection methods. Rational design includes, for example, using databases including triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, U.S. Pat. Nos. 6,140,081; 6,453,242; 6,534,261; 6,610,512; 6,746,838; 6,866,997; 7,067,617; U.S. Published Application Nos. 2002/0165356; 2004/0197892; 2007/0154989; 2007/0213269; and International Patent Application Publication Nos. WO 98/53059 and WO 2003/016496.

c. Transcription Activator-Like Effector Nucleases

In some embodiments, the element that induces a single or a double strand break in the target cell's genome is a nucleic acid construct or constructs encoding a transcription activator-like effector nuclease (TALEN). TALENs have an overall architecture similar to that of ZFNs, with the main difference that the DNA-binding domain comes from TAL effector proteins, transcription factors from plant pathogenic bacteria. The DNA-binding domain of a TALEN is a tandem array of amino acid repeats, each about 34 residues long. The repeats are very similar to each other; typically they differ principally at two positions (amino acids 12 and 13, called the repeat variable diresidue, or RVD). Each RVD specifies preferential binding to one of the four possible nucleotides, meaning that each TALEN repeat binds to a single base pair, though the NN RVD is known to bind adenines in addition to guanine. TAL effector DNA binding is mechanistically less well understood than that of zinc-finger proteins, but their seemingly simpler code could prove very beneficial for engineered-nuclease design. TAL-ENs also cleave as dimers, have relatively long target sequences (the shortest reported so far binds 13 nucleotides per monomer) and appear to have less stringent requirements than ZFNs for the length of the spacer between binding sites. Monomeric and dimeric TALENs can include more than 10, more than 14, more than 20, or more than 24 repeats.

Methods of engineering TAL to bind to specific nucleic acids are described in Cermak, et al, *Nucl. Acids Res.* 1-11 (2011). US Published Application No. 2011/0145940, which discloses TAL effectors and methods of using them to modify DNA. Miller et al. *Nature Biotechnol* 29: 143 (2011) reported making TALENs for site-specific nuclease architecture by linking TAL truncation variants to the catalytic domain of Fok1 nuclease. The resulting TALENs were shown to induce gene modification in immortalized human cells. General design principles for TALE binding domains can be found in, for example, WO 2011/072246.

2. Gene Altering Polynucleotides

The nuclease activity of the genome editing systems described herein cleave target DNA to produce single or double strand breaks in the target DNA. Double strand breaks can be repaired by the cell in one of two ways: non-homologous end joining, and homology-directed repair. In non-homologous end joining (NHEJ), the double-strand breaks are repaired by direct ligation of the break ends to one another. As such, no new nucleic acid material is inserted into the site, although some nucleic acid material may be lost, resulting in a deletion. In homology-directed repair, a donor polynucleotide with homology to the cleaved target DNA sequence is used as a template for repair of the cleaved target DNA sequence, resulting in the transfer of genetic information from a donor polynucleotide to the target DNA. As such, new nucleic acid material can be inserted/copied into the site.

Therefore, in some embodiments, the genome editing composition optionally includes a donor polynucleotide. The modifications of the target DNA due to NHEJ and/or homology-directed repair can be used to induce gene correction, gene replacement, gene tagging, transgene insertion, nucleotide deletion, gene disruption, gene mutation, etc.

Accordingly, cleavage of DNA by the genome editing composition can be used to delete nucleic acid material from a target DNA sequence by cleaving the target DNA sequence and allowing the cell to repair the sequence in the absence of an exogenously provided donor polynucleotide. Thus, the subject methods can be used to knock out a gene (resulting in complete lack of transcription or altered transcription) or to knock in genetic material into a locus of choice in the target DNA.

Alternatively, if the genome editing composition includes a donor polynucleotide sequence that includes at least a segment with homology to the target DNA sequence, the methods can be used to add, i.e., insert or replace, nucleic acid material to a target DNA sequence (e.g., to "knock in" a nucleic acid that encodes for a protein, an siRNA, an miRNA, etc.), to add a tag (e.g., 6×His, a fluorescent protein (e.g., a green fluorescent protein; a yellow fluorescent protein, etc.), hemagglutinin (HA), FLAG, etc.), to add a regulatory sequence to a gene (e.g., promoter, polyadenylation signal, internal ribosome entry sequence (IRES), 2A peptide, start codon, stop codon, splice signal, localization signal, etc.), to modify a nucleic acid sequence (e.g., introduce a mutation), and the like. As such, the compositions can be used to modify DNA in a site-specific, i.e., "targeted", way, for example gene knock-out, gene knock-in, gene editing, gene tagging, etc. as used in, for example, gene therapy.

In applications in which it is desirable to insert a polynucleotide sequence into a target DNA sequence, a polynucleotide including a donor sequence to be inserted is also provided to the cell. By a "donor sequence" or "donor polynucleotide" or "donor oligonucleotide" it is meant a nucleic acid sequence to be inserted at the cleavage site. The donor polynucleotide typically contains sufficient homology to a genomic sequence at the cleavage site, e.g., 70%, 80%, 85%, 90%, 95%, or 100% homology with the nucleotide sequences flanking the cleavage site, e.g., within about 50 bases or less of the cleavage site, e.g., within about 30 bases, within about 15 bases, within about 10 bases, within about 5 bases, or immediately flanking the cleavage site, to support homology-directed repair between it and the genomic sequence to which it bears homology. The donor sequence is typically not identical to the genomic sequence that it replaces. Rather, the donor sequence may contain at least one or more single base changes, insertions, deletions, inversions or rearrangements with respect to the genomic sequence, so long as sufficient homology is present to support homology-directed repair. In some embodiments, the donor sequence includes a non-homologous sequence flanked by two regions of homology, such that homology-directed repair between the target DNA region and the two flanking sequences results in insertion of the non-homologous sequence at the target region.

Donor sequences can also include a vector backbone containing sequences that are not homologous to the DNA region of interest and that are not intended for insertion into the DNA region of interest. Generally, the homologous region(s) of a donor sequence will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide.

The donor sequence can include certain sequence differences as compared to the genomic sequence, e.g., restriction sites, nucleotide polymorphisms, selectable markers (e.g., drug resistance genes, fluorescent proteins, enzymes etc.), etc., which can be used to assess for successful insertion of the donor sequence at the cleavage site or in some cases may be used for other purposes (e.g., to signify expression at the targeted genomic locus). In some cases, if located in a coding region, such nucleotide sequence differences will not change the amino acid sequence, or will make silent amino acid changes (i.e., changes which do not affect the structure or function of the protein). Alternatively, these sequences differences may include flanking recombination sequences such as FLPs, loxP sequences, or the like, that can be activated at a later time for removal of the marker sequence.

The donor sequence can be a single-stranded DNA, single-stranded RNA, double-stranded DNA, or double-stranded RNA. It can be introduced into a cell in linear or circular form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. *Proc. Natl. Acad. Sci. USA* 84:4959-4963 (1987); Nehls et al. *Science* 272:886-889 (1996). Additional methods for protecting exogenous poly-nucleotides from degradation include, but are not limited to, addition of terminal amino group(s) and the use of modified internucleotide linkages such as, for example, phosphoro-thioates, phosphor amidates, and O-methyl ribose or deoxy-ribose residues.

As an alternative to protecting the termini of a linear donor sequence, additional lengths of sequence can be included outside of the regions of homology that can be degraded without impacting recombination. A donor sequence can be introduced into a cell as part of a vector molecule having additional sequences such as, for example, replication origins, promoters and genes encoding antibiotic resistance.

B. Target Diseases

The disclosed methods of gene editing can be used to treat a variety of genetic diseases and disorders. Embodiments in which the treated cells are ESCs, iPSCs, or male gametes (e.g., spermatids cells), are particularly beneficial for cor-recting paternally inherited dominant genetic diseases and recessive genetic diseases (e.g., that need two mutated copies of parental alleles). By permanently correcting pater-nal mutations, the genetic anomaly causing the problem can be diluted and ultimately eradicated over future generations.

Exemplary inherited dominant genetic disorders include, but are not limited to, Huntington's Disease, Spinocerebellar Ataxia (SCA), Fragile-X syndrome etc. Exemplary reces-sive genetic diseases include, but are not limited to, cystic fibrosis, sickle cell anemia, Tay-Sachs etc.

In some embodiments, the disease is a monogenic disease. Monogenic diseases for which the disease genotype is known include, but are not limited to, achondroplasia, adrenoleukodystrophy, alpha thalassaemia, alpha-1-antit-rypsin deficiency, alport syndrome, amyotrophic lateral scle-rosis, beta thalassemia, Charcot-Marie-Tooth, congenital disorder of glycosylation type 1a, crouzon syndrome, cystic fibrosis, Duchenne and Becker muscular dystrophy, dystonia 1, torsion, Emery-Dreifuss muscular dystrophy, facioscapu-lohumeral dystrophy, familial adenomatous polyposis, familial amyloidotic polyneuropathy, familial dysautono-mia, fanconi anaemia, fragile x, glutaric aciduria type 1, haemophilia a and b, hemophagocytic lymphohistiocytosis, holt-oram syndrome, Huntington's disease, hyperinsuline-mic hypoglycemia, hypokalaemic periodic paralysis, incon-tinentia pigmenti, lynch syndrome, marfan syndrome, men-kes disease, metachromatic leukodystrophy, mucopolysaccharidosis type II (Hunter syndrome), multiple endocrine neoplasia (MEN2), multiple exostosis, myotonic dystrophy, neurofibromatosis type i and ii, non-syndromic sensorineural deafness, Norrie syndrome, osteogenesis imperfecta (brittle bone disease), polycystic kidney-auto-somal dominant, polycystic kidney-autosomal recessive, Pompe's syndrome, sickle cell anaemia, Smith-Lemli-Opitz syndrome, spastic paraplegia 4, spinal and bulbar muscular atrophy, spinal muscular atrophy, spinocerebellar ataxia 1, 2 and 3, spondylometaphyseal dysplasia (schmidt), Tay-Sachs disease, Treacher Collins, tuberous sclerosis, and Von Hip-pel-Lindau syndrome. In some embodiments, a gene editing composition that can correct a mutation or genetic anomaly is delivered (e.g., transfection, injection, etc.) into ESCs, iPSCs, male gametes (e.g., spermatids cells), a fertilized egg, or early stage embryo in an effective amount to correct the mutation or genetic anomaly.

In some embodiments, the disease is an autistic spectrum disorder (ASD), and gene editing composition targets one or more mutations or genetic anomalies associated therewith. There are currently no cures for ASD, and treatments are only available for particular symptoms pertaining to a child's development. It is a devastating disorder that has significant social and economic impact as the number of children affected increases. The diagnosis of ASD is primar-ily based on deficits in all of the following: reciprocal social interaction, communication and stereotyped behaviors. In populations of diagnosed children, 15-70% exhibit intellec-tual impairments. The fundamental diagnosis for ASD is homogeneous, based on the criteria listed above; however, ASD can also co-exist in patients with syndromes such as Fragile X or neurofibromatosis.

Genetic studies of ASD have yielded an intriguing list of select genomic targets with several of the genes directly linked to the regulation of critical synaptic functions, includ-ing FMR1, MECP2, PTEN, UBE3A, NLGN1-NLGN4, NRXN1 and SHANK3. Moreover, some of the candidates, such as SHANK3, are associated to ASD in a gene-dosage-dependent manner. SHANK3, a gene integral to the gluta-matergic pathway, is a binding partner for the neuroligins NLGN3 and NLGN4, which themselves bind neurexins, all of which are genetically associated with ASD progression. Additionally, mutations in genes downstream of SHANK3 signaling, such as DIAPH3, have also been linked to ASD. Consequently, disruption of SHANK3-mediated glutamater-gic transmission appears to play a pivotal role in ASD pathogenesis. Moreover, the chromosomal location of SHANK3 at 22q13 is linked to considerable human pathol-ogy due to genetic deletions which result in SHANK3 haploinsufficiency and strong phenotypes of developmental and language delays.

C. Genetic Testing and Selection

Some embodiments include a step of genetic testing and/or selection of edited cells. Such techniques are known in the art. For example, cells and embryos can be screened using genetic sequencing and/or PCR-based methods for detection of mutations (or correction thereof) and FISH for chromosomal abnormalities. Protocols include, for example, prenatal diagnosis, pre-implantation genetic diagnosis, pre-implantation genetic screening (PGS), oocyte selection, sperm selection, etc.

V. Non-Clinical Applications

Although generally described herein with respect to meth-ods of treatment, the disclosed compositions and methods also have applications outside the clinic. For example, disclosed methods can be used to generate functional sper-matids from rare or endangered animals-species preserva-tion, or otherwise improve methods of assisted reproduction thereof. Spermatids can be generated from male animals that are unable to breed or have gone sterile due to age, thus allowing the preservation of rare or endangered mammals.

The disclosed methods can also be used to prepare gene targeted haploid spermatids for the creation of hemizygotic or semi-cloned embryos by fertilizing mature oocytes (e.g. monkeys), which is an ideal method to create animal models of haploinsufficiency-associated diseases such as Mendelian susceptibility to mycobacterial disease (MSMS) and Ehlers-Danlos syndrome etc. Thus, in some embodiments (and as in the working example below), the gene editing methods are used to induce a disease or dysfunction-causing mutation to, for example, further it study.

In some embodiments, an oocyte activation approach is used to improve somatic cell nuclear transplantation (SCNT), parthenogenic embryos and improve ICSI and ROSI efficiency. Synthetic TET3 or another TET gene family protein treatment could potentially improve efficiency of all of the above applications.

In some embodiments, the compositions and methods are used too improve the making of patient-specific stem cell lines for therapeutic approaches. These stem cells can be used, for example, in combination with somatic cell nuclear transfer (SCNT) for generating patient-specific stem cells.

EXAMPLES

Example 1: In Vitro Differentiated Spermatids can Fertilize Oocytes, Divide and Form Blastocysts in Culture

Materials and Methods

NHP Embryonic Stem Cell Differentiation.

Male Rhesus macaque embryonic stem cell line (Navara et al., *Stem Cells* 25, 2695-2704, doi:2007-0286 [pii] 10.1634/stemcells.2007-0286 (2007)) stably transduced with H2B-GFP was differentiated as previously described (Easley et al., *Cell Rep* 2, 440-446, doi: 10.1016/j.celrep.2012.07.015 (2012)). For FIG. 2A, the same non-transduced line was used in addition to a rhesus induced pluripotent stem cell (nhpiPSC) line and a somatic cell nuclear transfer embryonic stem cell (nhpNT) line (Byrne et al., *Nature* 450, 497-502, doi: 10.1038/nature06357 (2007)). Briefly, nhp pluripotent stem cell lines were cultured for 10 days on STO-feeder cells in mouse spermatogonial stem cell (SSC) medium containing the following: MEMalpha (Thermofisher), 0.2% Bovine Serum Albumin (Sigma), 5 μg/ml insulin (Sigma), 10 μg/ml transferrin (Sigma), 60 μM putrescine (Sigma), 2 mM L-glutamine (Invitrogen), 50 μM β-mercaptoethanol (Sigma), 1 ng/ml hbFGF (human basic fibroblast growth factor, R&D Systems), 20 ng/ml GDNF (glial-derived neurotrophic factor, R&D Systems), 30 nM sodium selenite (Sigma), 2.36 μM palmitic acid (Sigma), 0.21 μM palmitoleic acid (Sigma), 0.88 μM stearic acid (Sigma), 1.02 μM oleic acid (Sigma), 2.71 μM linoleic acid (Sigma), 0.43 μM linolenic acid (Sigma), 10 mM HEPES (Sigma), and 0.5× penicillin/streptomycin (Thermofisher). Cells were refed with fresh medium every other day and SSC medium was gassed with a blood gas mixture (5% $CO_2$, 5%02, 90% nitrogen gas) prior to use. For comparison in FIG. 2A, nhpESC H2B-GFP cells were differentiated with a BMP mixture as described (Kee et al., *Nature* 462, 222-225, doi:nature08562 [pii]10.1038/nature08562 (2009)) without the addition of DAZL, DAZ, and BOULE.

Haploid Cell Isolation, Cell Cycle Profiling, Fluorescence In Situ Hybridization (FISH).

To isolate haploid cells during fluorescence-activated cell sorting (FACS), differentiated H2B-GFP nhpESCs were trypsinized and stained with RedDot1 DNA stain (Biotium) as per manufacturer's instructions in the SSC medium listed above. Haploid cells were then cultured on poly-d-lysine-coated coverslips and fixed with 4% para-formaldehyde prior to immunostaining (see below).

For cell cycle profiling, differentiated cultures were trypsinized and stained using the Cell Cycle Kit for the Millipore MUSE cell analyzer as per manufacturer's instructions (EMD Millipore).

To determine diploidy and haploidy on interphase cells, hPSCs or isolated haploid cells were attached to microscope slides by cytospin at 180×g for 6 minutes. Slides were then fixed in Carnoy's fixative (3:1 methanol to glacial acetic acid) for 5 minutes at room temperature and then air-dried. Slides were dehydrated by successive ice-cold ethanol treatments for 2 minutes each (100%, 80% and 70%) and then air-dried. Cytogenetic preparations were then denatured at 75° C. in 70% formamide for 5 minutes while the custom LNA probe against satellite DNA on chromosomes 1 and Y (Exiqon) was simultaneously denatured at 75° C. in hybridization buffer (50% formamide/2×SSC, pH 7.0/10% dextran sulfate) for 5 minutes. LNA probe was hybridized onto samples overnight at 37° C. Following hybridization, slides were washed in 0.25×SSC for 5 minutes at 60° C. followed by a second wash in 2×SSC/0.1% Tween-20 for 5 minutes at 60° C. Samples were then mounted with Vectashield with DAPI and imaged.

Immunostaining and RT-PCR.

nhpESCs cultured in conditions described above were fixed in 4% paraformaldehyde (Sigma) for 15 minutes and then blocked with buffer containing 1× Phosphate-buffered Saline Solution (PBS) (Thermofisher), 0.25% Triton X (Sigma), 5% bovine serum albumin (BSA) (Fisher Scientific) and 5% normal goat serum (NGS) or donkey serum (Sigma) overnight at 4° C. Primary antibody incubation occurred overnight at 4° C. in blocking buffer followed by 3 washes in 1×PBS with 0.25% Triton-X for 10 minutes each at room temperature. Secondary antibody (Thermofisher 1:2000 dilution) incubation was performed at room temperature for 2 hours followed by 3 washes as described above. Samples were co-stained with Hoechst. For FACS-obtained haploid cells, isolated cells were seeded onto poly-d-lysine coated coverslips for 10 minutes at 37° C. Coverslips were then fixed in 4% paraformaldehyde and stained as described above. Additionally, rhesus testis cell suspensions were seeded onto poly-d-lysine coated coverslips for 10 minutes at 37° C. VASA, UTF1, and PLZF antibodies were from R&D Systems. PIWIL1 and PIWIL2 antibodies were from Abcam. Acrosin, Protamine 1, and Transition Protein 1 were from Santa Cruz Biotechnology. Acetylated tubulin antibody was from Thermofisher. All fluorescent secondary antibodies were from Thermofisher. All images shown are representative of at least 5 separate immunostaining experiments. For VASA+counts, 5000 cells were counted for each differentiation and each differentiation was performed 5 times (n=5). Percentages of total cell counts were calculated and averaged for the 5 trials.

For RT-PCR, custom PrimePCR arrays (Bio-Rad) were designed with validated PCR primers to primate genes DAZL, DDX4, GFRA1, GPR125, PIWIL1, PIWIL2, ZBTB16, SYCP3, THY1, CKIT, ACR, PRM1, PRM2, GAPDH, ACTB, and TNP1. Assays were run according to manufacturer's instructions. For each plate, there were 2 replicates and 3 plates were run representing 3 separate and distinct biological replicates. Normalized fold change (2^δCT) is shown.

Genomic Imprint Analyses for H19 and SNRPN.

Genomic DNA from diploid nhpESCs and haploid cells obtained from FACS were obtained using the DNeasy Blood and Tissue kit from Qiagen following manufacturer's instructions. Samples were prepared for imprint control region methylation analyses with the Epitect Methyl DNA Restriction Kit (Qiagen) as per manufacturer's instructions. For qPCR-based analyses of imprint control region methylation for H19 and SNRPN for each sample, the following Epitect qPCR Methyl Promoter Primers were used: H19-catalog number: 335002 EPHS102101-1A, SNRPN-335002 EPHS104389-1A. % Methylation for H19 and SNRPN imprint control regions were calculated for each sample as per manufacturer's instructions (Qiagen).

Round Spermatid Isolation, Oocyte Collection, and Intracytoplasmic Sperm(atid) Injection (ICSI).

Hyperstimulation of female rhesus monkeys exhibiting regular menstrual cycles was induced with exogenous gonadotropins. Beginning at menses, females were given recombinant human FSH (r-hFSH; Organon Inc., West Orange, NJ; 35 IU, i.m.) for six days, administered twice daily, followed by one-to-three days of r-hFSH+r-hLH (r-hLH; Ares Serono; 30 IU each, i.m.), twice daily, and subcutaneous injections of a GnRH antagonist (Acyline; NICHD/NIH; 75 mg/kg body weight), once daily. Ultrasonography was performed on day seven of the stimulation to confirm adequate follicular response. When there were follicles 3-4 mm in diameter, an i.m. injection of 1500 IU r-hCG (Serono, Randolph, MA) was administered for ovulation and metaphase II (MII) oocytes were retrieved at ~35 hours post-r-hCG injection for intracytoplasmic spermatid injection (ICSI) (Arthur Chang, & Chan, *Methods Mol Biol* 770, 337-363, doi: 10.1007/978-1-61779-210-6_13 (2011)).

After 10 day differentiations, round spermatids were isolated by trypsinizing cultures and spotting cells into ICSI injection medium. Round spermatids were picked for ICSI using morphological characteristics outlined by Tanaka et al. (Tanaka et al., *Proc Natl Acad Sci USA* 112, 14629-14634, doi: 10.1073/pnas. 1517466112 (2015), Tanaka et al., *Fertil Steril* 110, 443-451, doi: 10.1016/j.fertnstert.2018.04.033 (2018)). In a vertical array, round spermatids were resuspended in 5 μl drop of SSC differentaition medium and placed onto a petri dish. A second 5 μl drop contain a mixture 1 μl (TET3 protein), 1 μl of TET3 plasmid DNA (~1 ng/μl) and 3 μl of sperm cytoplasmic factor (SCF) (Simerly & Navara, *Cloning Stem Cells,* 5, 319-331, doi: 10.1089/153623003772032826 (2003)). The third 5 μl drop of TL-HEPES was placed at the bottom where oocytes were placed for ICSI. A ICSI micropipette (~9 μm inner diameter) was used to aspirate round spermatids, washed in TET3-SCF mixture, followed by cytoplamic injection into MII oocytes at position 90 degree away from the first polar body. After ICSI, fertilized oocytes were placed into HECM-9 culture medium with 10 nM of Trichostatin A (TSA; Sigma T1952) for 10 hours followed by thorough wash and placed in HECM-9 media for in vitro culture.

In vitro fertilization using spermatids is similar to intracytoplasmic sperm injection (ICSI). In brief, sorted haploid round spermatids can be co-injected with sperm extract and Tet3 protein into mature oocyte followed by in vitro culture using established assisted reproduction protocols. Preimplantation embryos can be in vitro cultured until blastocyst for developmental assessment.

Statistics.

2-tailed, unequal variance t-tests were performed to establish significance for various experiments within this study. Significance was determined as $p<0.5$. Graphical analyses shown are indicative of average values+/−standard deviation. For all experiments, greater than 3 trials were performed, and data are representative of all trials.

Results

Human pluripotent stem cells (hPSCs) have been differentiated, including into human embryonic (hESCs) and induced pluripotent stem cells (hiPSCs), into germ cell lineages (Easley et al., *Cell Rep* 2, 440-446, doi:10.1016/j.celrep.2012.07.015 (2012), Hayashi et al., *Cell* 146, 1-14, doi:10.1016/j.cell.2011.06.052 (2011), Kee et al., *Nature*

462, 222-225, doi:nature08562 [pii] 10.1038/nature08562 (2009), Panula et al., *Hum Mol Genet* 20, 752-762, doi: ddq520 [pii]10.1093/hmg/ddq520 (2011), Zhao et al., *Stem Cell Reports* 10, 509-523, doi:10.1016/j.stemcr.2018.01.001 (2018)). In some cases, production of spermatogonia-like cells, primary and secondary spermatocyte-like cells, and haploid spermatid-like cells were shown (Easley et al., *Cell Rep* 2, 440-446, doi: 10.1016/j.celrep.2012.07.015 (2012), Zhao et al., *Stem Cell Reports* 10, 509-523, doi:10.1016/j.stemcr.2018.01.001 (2018)). However, in these studies the "Gold Standard" (Handel et al., *Cell* 157, 1257-1261, doi: 10.1016/j.cell.2014.05.019 (2014)) for producing functional gametes that could fertilize an oocyte was not assessed. Work in rodents has demonstrated the ability to produce live offspring from sperm cells generated by testicular grafts of in vitro differentiated mouse precursor germ cells (Hayashi et al., *Cell* 146, 1-14, doi: 10.1016/j.cell.2011.06.052 (2011)). Additionally, complete meiosis from differentiating mouse embryonic stem cells has been achieved (Zhou, et al., *Cell Stem Cell,* 18, 330-340, doi: 10.1016/j.stem.2016.01.017 (2016)). Yet there are distinct biological and kinetic differences between rodents and humans (Ehmcke et al., *Hum Reprod Update* 12, 275-282, doi: 10.1093/humupd/dmk001 (2006), Fayomi & Orwig, *Stem Cell Res* 29, 207-214, doi:10.1016/j.scr.2018.04.009 (2018)). Additionally, functional male gametes have not been derived completely in vitro from rodent pluripotent stem cells.

To test whether functional gametes can be derived completely in vitro from pluripotent stem cells, a model more relevant to humans was used: a non-human primate (NHP), rhesus macaque model. Unlike rodents, NHP such as rhesus macaque share similar biological mechanisms to human spermatogenesis, fertilization, early embryo and fetal development (Ehmcke et al., *Hum Reprod Update* 12, 275-282, doi: 10.1093/humupd/dmk001 (2006), Fayomi & Orwig, *Stem Cell Res* 29, 207-214, doi:10.1016/j.scr.2018.04.009 (2018)). Spermatogenesis in NHPs is more kinetically similar to humans than rodents. Fertilization is also different in rodents versus primates in that successful fertilization requires paternal centriole inheritance in both nonhuman primates and humans but not in rodents (Navara, *Reprod Fertil Dev* 7, 747-754 (1995), Schatten & Simerly, *EMBO* reports 16, 1052-1054, doi: 10.15252/embr.201540875 (2015), Simerly et al., *Nat Med* 1, 47-52 (1995)). Taken together, NHP models of spermatogenesis are more similar to humans than rodent models and thus represent an ideal and necessary model for exploring stem cell-based therapies for male infertility prior to clinical use.

Figures 2A, 2B:
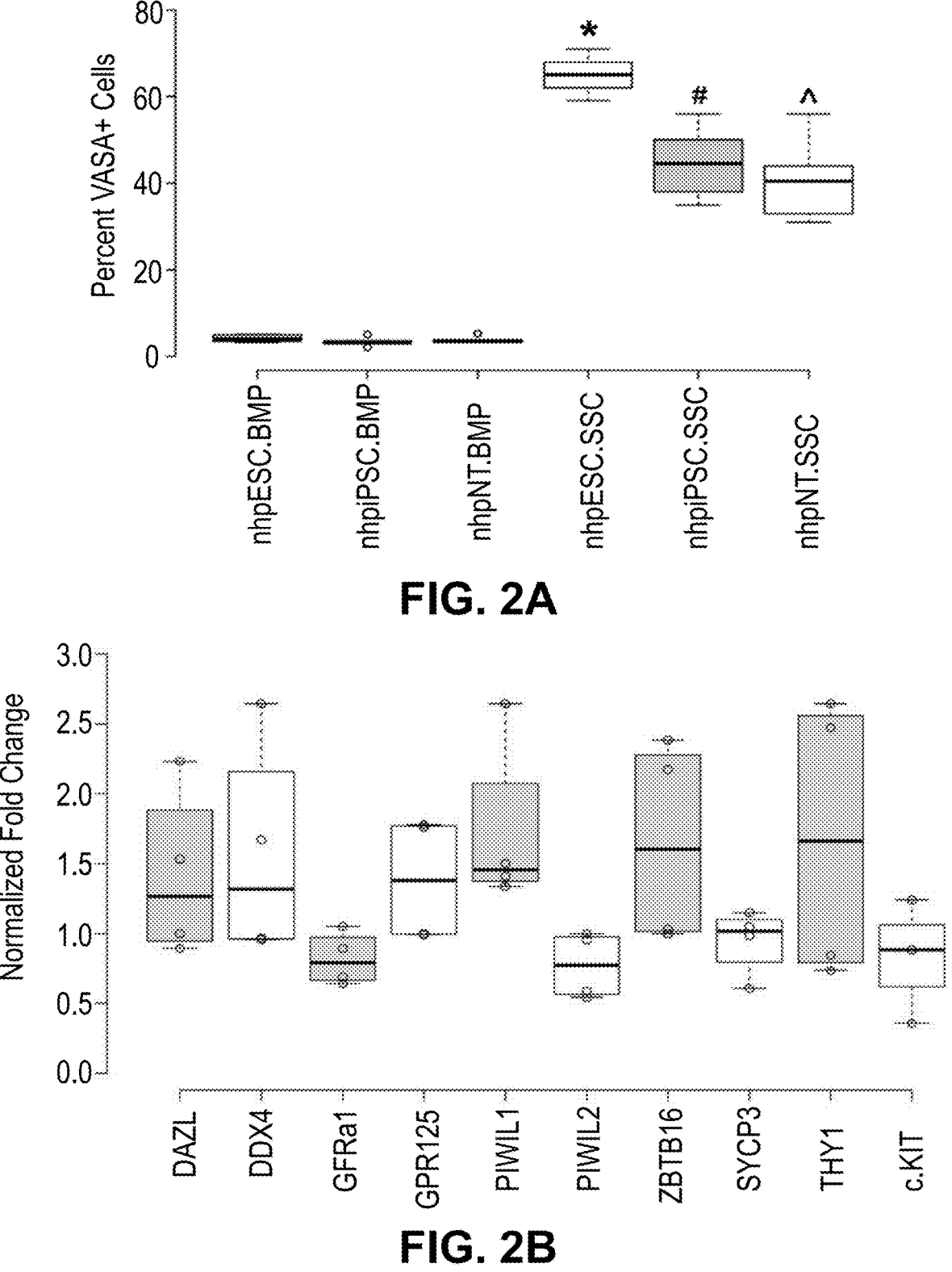
FIG. 2A is a graph showing VASA protein expression in nhpESCs, nhpiPSCs, and nhpNT-ESCs (nuclear transfer derived ESCs) cultured in mouse SSC culture conditions for 10 days compared to cells differentiated for 14 days using a BMP cocktail. *, #, and ^ all represent statistical significance $p < 0.01$.
FIG. 2B is a graph showing normalized fold change ($2^{\delta CT}$) for germline-related genes (DAZL, DDX4, GFRa1, GPR125, PIWIL1, PIWIL2, ZBTB16, SYCP3, THY1, cKit) in nhpESC H2B-GFP cells differentiated for 10 days in SSC conditions.
Figure 2C:
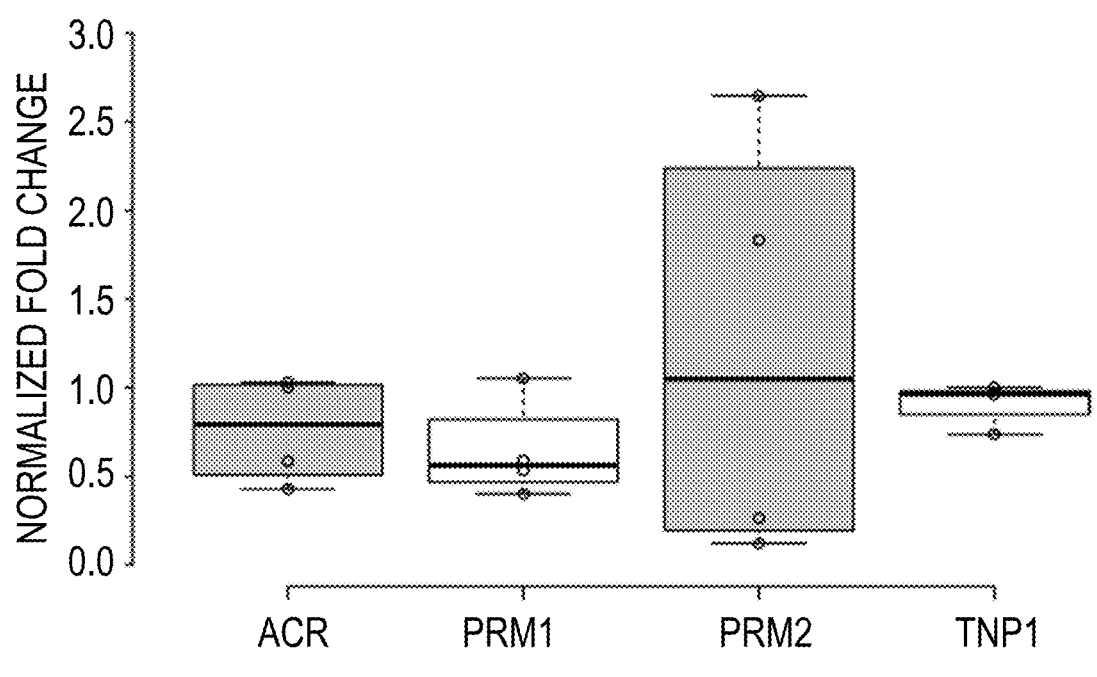
FIG. 2C is a graph showing normalized fold change ($2^{\delta CT}$) for haploid spermatid-related genes (ACR, PRM1, PRM2, THP1) in nhpESC H2B-GFP cells differentiated for 10 days in SSC conditions.
Figure 2D:
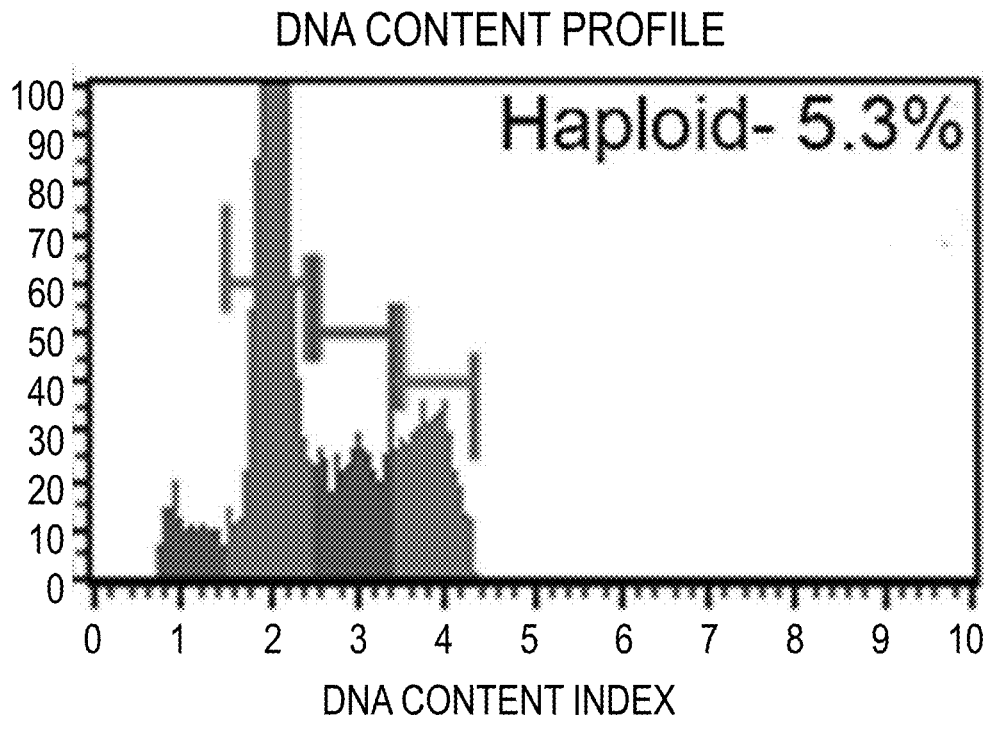
FIG. 2D is a histogram showing a representative cell cycle flow cytometry profile of nhpESC H2B GFP cells differentiated in SSC conditions for 10 days. The first peak represents the 1N peak, the second peak represents the 2N peak, the third peak represents S phase, and the fourth peak represents the 4N peak. Fluorescence in situ hybridization (FISH) confirmed haploidy of round spermatid like cells.
Figure 3A:
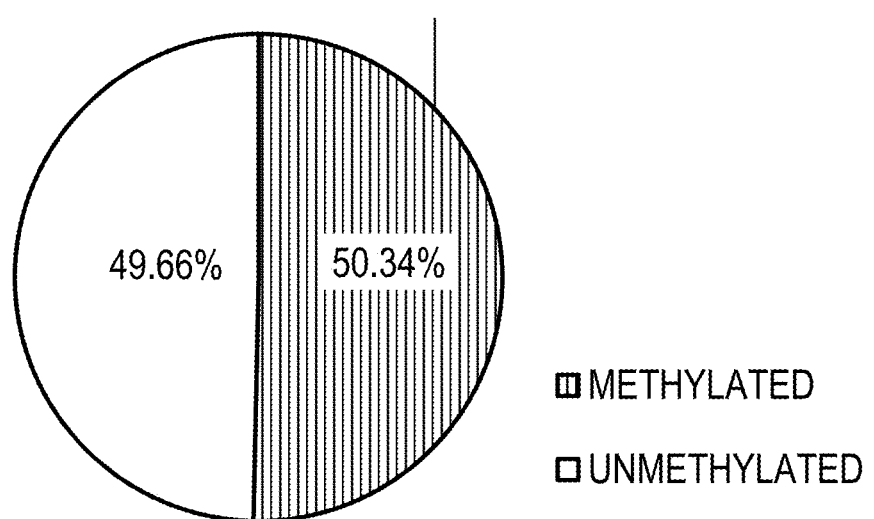
FIGS. 3A-3D are pie graphs comparing DNA methylation on imprint control regions (ICRs) for H19 (paternally silenced) and SNRPN (paternally expressed) in haploid spermatids and diploid cells. Diploid parent nhpESC H2B-GFP cells show ~50% methylation for both H19 (3A) and SNRPN (3B) whereas haploid round spermatid-like cells show high levels of DNA methylation on the paternally silenced ICR H19 (3C) and low levels of DNA methylation on the paternally expressed ICR SNRPN (3D) similar to rhesus sperm.
Figure 3B:
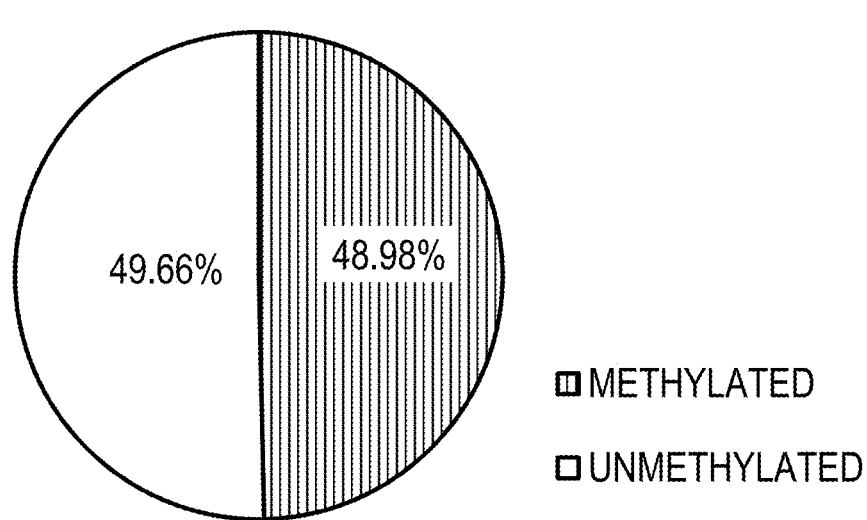
Figure 3C:
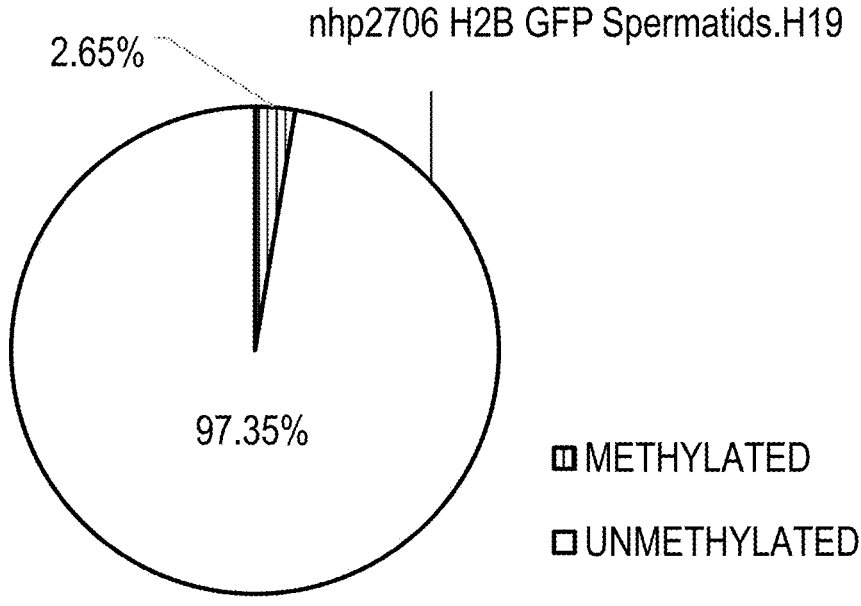
Figure 3D:
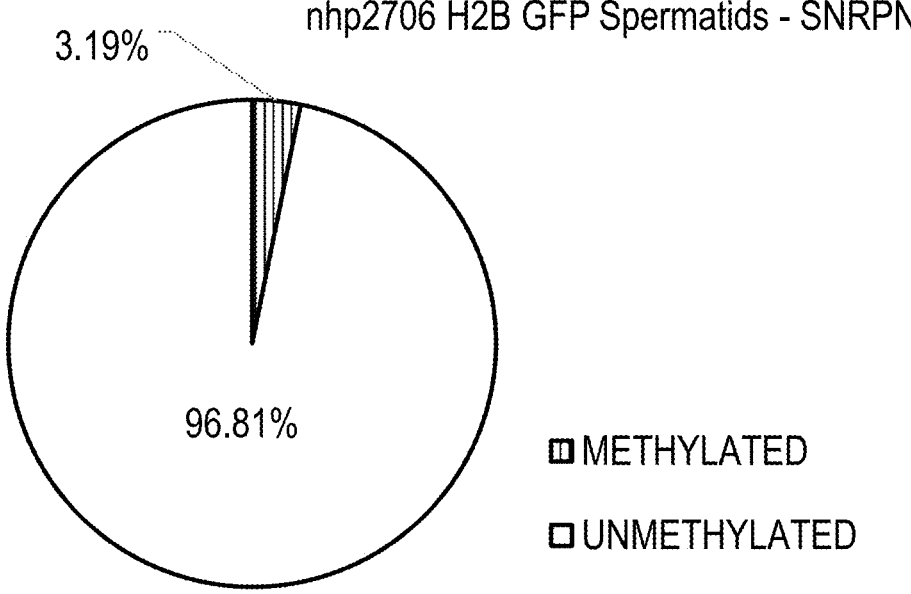

To first determine whether nhpESCs differentiate into spermatogenic cells similar to hESCs and hiPSCs, nhpESCs were first differentiated in a spermatogonial stem cell (SSC) differentiation protocol as previously described (Easley et al., *Cell Rep* 2, 440-446, doi: 10.1016/j.celrep.2012.07.015 (2012), Zhao et al., *Stem Cell Reports* 10, 509-523, doi: 10.1016/j.stemcr.2018.01.001 (2018), Easley et al., *Stem Cell Res* 14, 347-355, doi: 10.1016/j.scr.2015.03.002 (2015), Steves et al., iScience 3, 161-176, doi: 10.1016/j.isci.2018.04.014 (2018), Steves et al., *Syst Biol Reprod Med* 64, 225-239, doi: 10.1080/19396368.2018.1481465 (2018)). A Histone 2B-GFP nhpESC (nhpESC H2B-GFP) line was chosen for downstream analyses, but all lines tested (FIG. 2A) differentiated in spermatogonia-like cells, primary and secondary spermatocyte-like cells, and haploid spermatid-like similarly to differentiations using hESCs and hiPSCs (FIGS. 2B-2D). Moreover, haploid spermatid-like cells produced by the differentiation protocol demonstrated expression of acrosin, protamine 1, and transition protein 1 (FIG. 2C); showed morphological similarities to endogenous NHP round spermatids; and showed proper imprint establishment on two confirmed parent-of-origin imprints in NHPs (Fujimoto et al., *Mol Hum Reprod* 11, 413-422, doi: 10.1093/molehr/gah180 (2005), Fujimoto et al., *Stem Cells* 24, 595-603, doi: 10.1634/stemcells.2005-0301 (2006)) (FIGS. 3A-3D). Confirmation of haploidy by fluorescence in situ hybridization demonstrated that both X and Y round spermatid-like cells were produced (FIG. 2D).

Figure 4A:
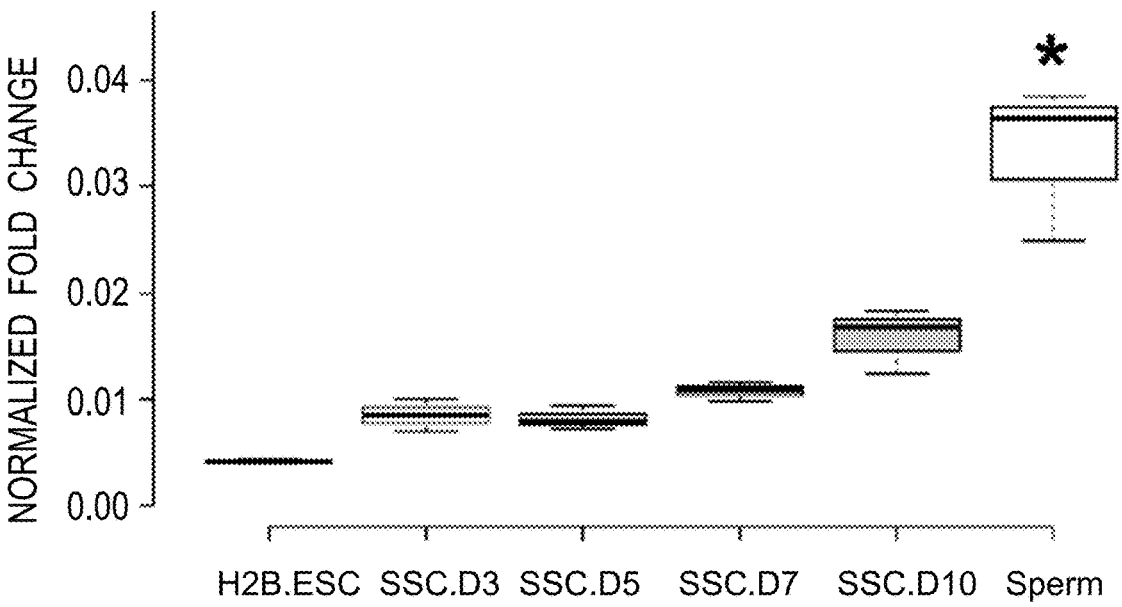
FIG. 4A is a graph illustrating the expression of Tet3 in embryonic stem cells (ESCs), differentiating sperm cells at Day 3, 5, 7 and 10 of in vitro SSC differentiation, and mature spermatozoa collected from rhesus macaque. While progressive increased expression of Tet3 was observed as ESCs differentiated to haploid spermatids on Day 10, a significantly lower expression compared to mature spermatozoa was observed. Normalized fold change ($2^{\delta CT}$) for TET3 is shown. * $p < 0.001$.
Figure 4B:
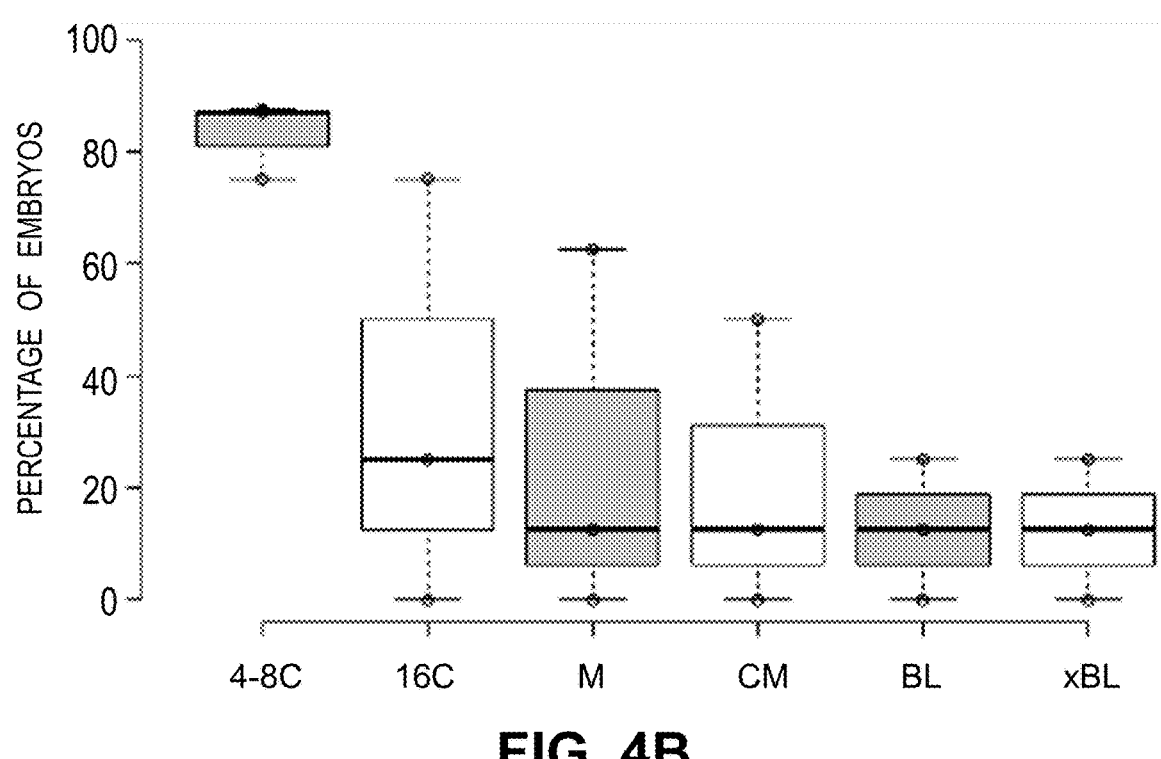
FIGS. 4B-4G are graphs of the percentage of embryos that reach each developmental/post fertilization stage including the 4-8 cell stage (4-8C), 16 cell stage (16C), morula (M), compacted morula (CM), early blastocyst (BL), and expanded blastocyst (xBL) stages when in vitro-derived round spermatid-like cells are co-injected with TET3 protein and activated by sperm cell factor (SCF) (4B), ococyte activation by DMAP/ionomycin treatment (4C), oocyte activation by sperm cell factor (SCF) (4D), SCF plus TET3 plasmid DNA (4E), SCF plus TET3 plasmid DNA plus TET3 mRNA (4F), fertilization by ICSI with rhesus sperm (4G).
Figures 4C, 4D:
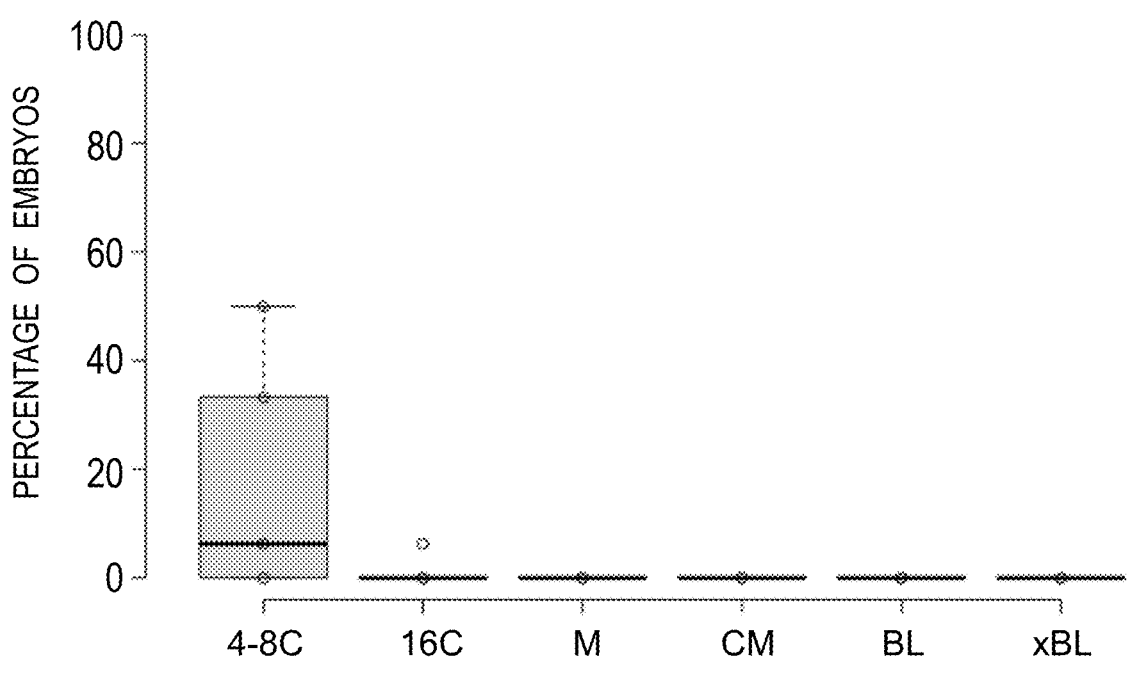
Figure 4E:
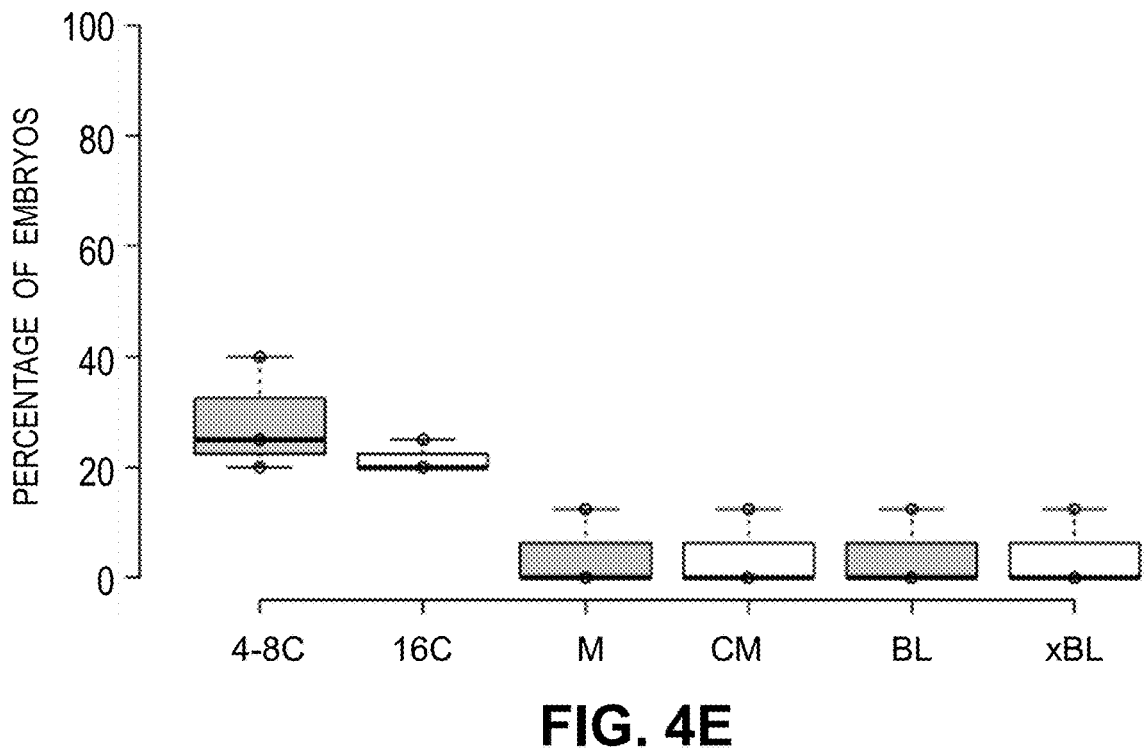
Figure 4F:
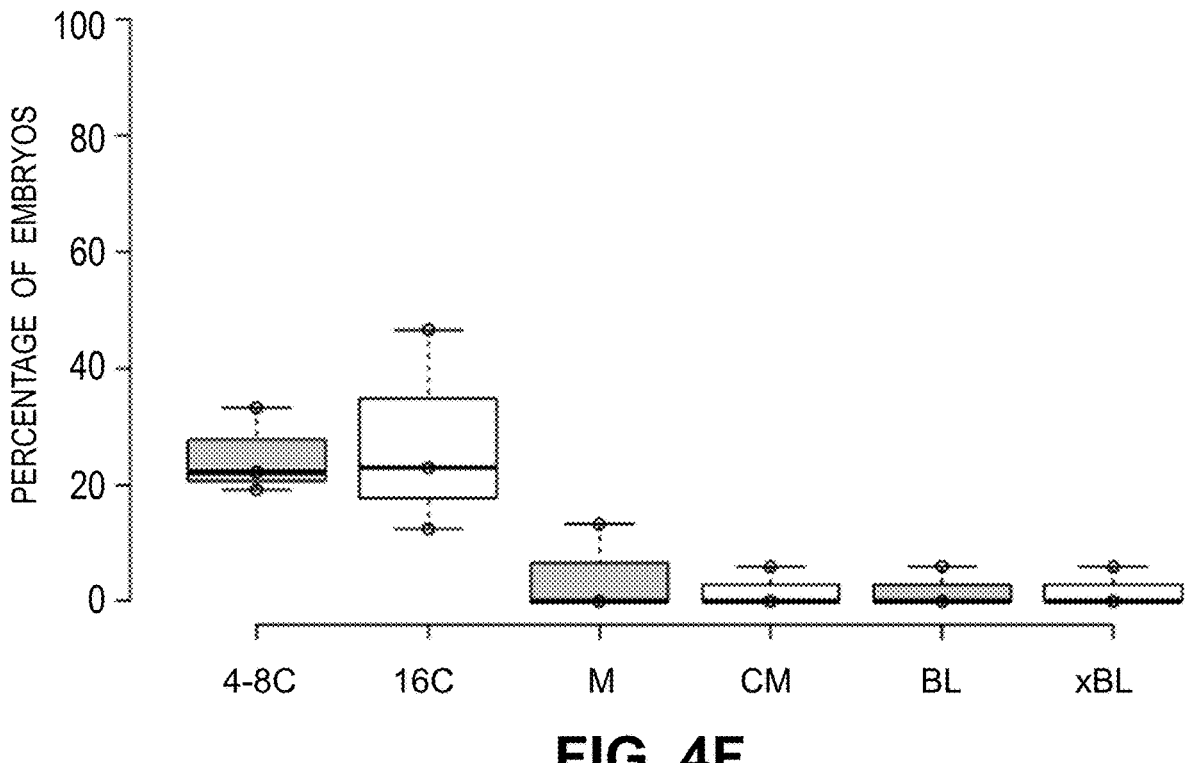
Figures 4G, 5A:
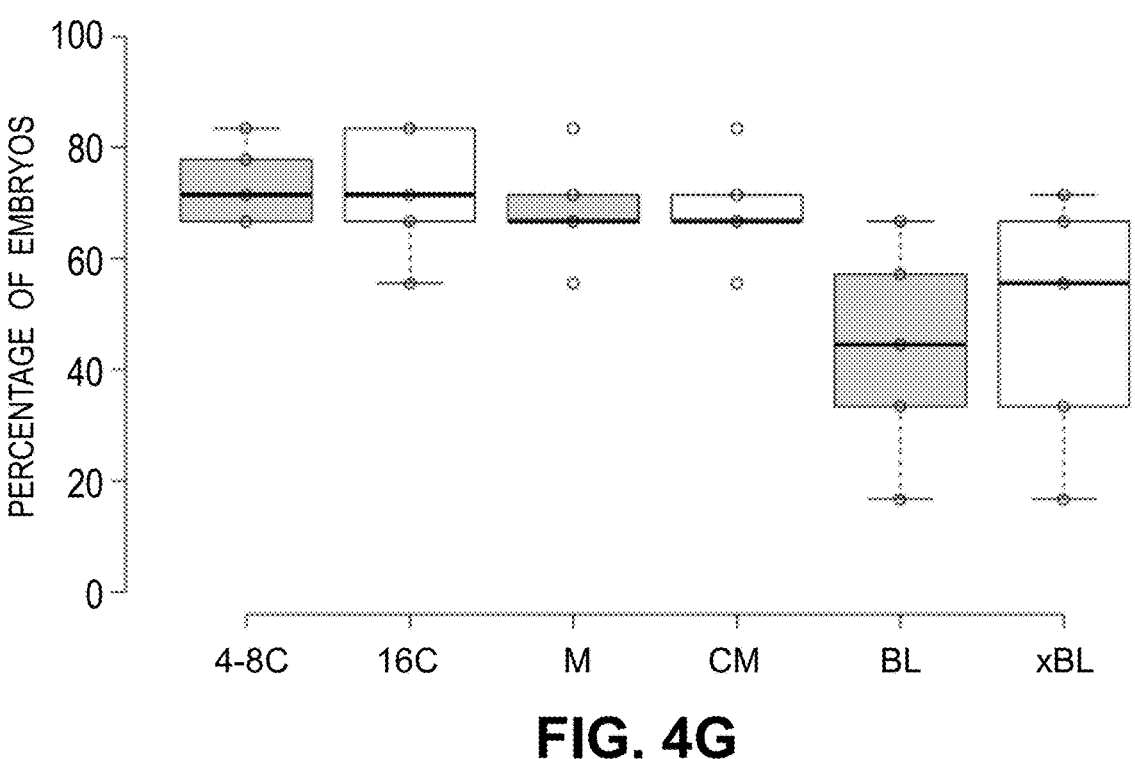
FIG. 5A is an illustration of SHANK3 target sequences (SEQ ID NOS:4 and 5) and an exemplary gRNA (SEQ ID NO:6).

Similar to hESCs and hiPSCs (Easley et al., *Cell Rep* 2, 440-446, doi:10.1016/j.celrep.2012.07.015 (2012)), nhpESC-derived spermatogenic cells, including round spermatid-like cells, exhibited many of the hallmarks of the "Gold Standards" of in vitro-derived gametes. To explore whether NHP in vitro-derived round spermatid-like cells (rSLCs) have functional gamete ability, rhesus oocytes were fertilized by intracytoplasmic sperm injection (ICSI). Like clinical ART applications using endogenous round spermatids, in vitro derived round spermatid-like cells could not activate oocytes for in vitro development, but these round spermatid-like cells did undergo DNA decondensation and pronucleus formation, generally arresting at the 4-8 cell developmental stage (FIGS. 4A and 4B). Upon oocyte activation using a crude sperm extract (Meng & Wolf, *Hum Reprod* 12, 1062-1068, doi: 10.1093/humrep/12.5.1062 (1997)), ICSI of rSLCs induced further development DNA decondensation, male and female pronuclei formation, and cleavage. While most embryos arrested at the 8-16 cell stage, the stage where non-human primates undergo maternal to zygotic transcription control, some did progress to the blastocyst stage (FIGS. 4A and 4B). GFP-H2B expression in the nuclei of cells throughout the developing embryo demonstrate that the male genome from the nhpESC-derived rSLCs contributed to the developing embryo.

Example 2: Tet3 Enhances the Morphology and Development Rate of Preimplantation Embryos

Materials and Methods

TET3 Gene Expression and In Vitro Transcription/Translation of TET3.

TET3 Gene Expression and in vitro Transcription/Translation of TET3. Full length human TET3 (FH-TET-pEF; Addgene #49446, the sequence of which is specifically incorporated by reference herein in its entirety) plasmid DNA was used to generate TET3 protein supplements for ICSI. TET3 protein was generated using the Promega TnT (Transcription and Translation) kit as per manufacturer's instructions. Following generation of TET3 protein, TET3 was immunopurifed from the reticulocyte lysate using the Dynabeads Protein A Immunoprecipitation kit (Thermofisher) per manufacturer's instructions using an immunoprecipitating-capable TET3 antibody (Abcam) with the following modification: immunoprecipitation was incubated overnight at 4° C. Following elution from Dynabeads, purified TET3 protein was diluted in ICB buffer (KCL 120 mM, HEPES 20 mM, EGTA 100 µM, Sodium glycerophosphate 10 mM; pH 7.5)36 compatible with ICSI.

TET3 RNA levels were measured in nhpESCs, Day 3, Day 5, Day 7, Day 10 differentiation cultures, and in mature wild-type sperm. RNA from all samples listed above was isolated by RNeasy RNA isolation kit (Qiagen) per manufacturer's instructions. cDNA was generated as described above using iScript Reverse Transcription Supermix for RT-qPCR (Bio-Rad) per manufacturer's instructions. 3 distinct biological replicates were used for analyses with average Normalized fold change ($2^{\delta CT}$) shown. PCR primer sequences for TET3: Forward-5' CCCAAAGAG-GAAGAAGTG 3' (SEQ ID NO:14); Reverse-5' GCAGT-CAATCGCTATTTC 3' (SEQ ID NO:15).

Addgene #49446 provides a nucleic acid sequence insert:

(SEQ ID NO: 12)

```
atggactacaaggacgacgatgacaagctcgatggaggatacccctacgac
gtgcccgactacgccggaggactcgacagccagtttcaggtgcccctggcc
gtccagccggacctgccaggcctttatgacttccctcagcgccaggtgatg
gtagggagcttcccgggggtctgggctctccatggctgggagtgagtcccaa
ctccgaggggggtggagatggtcgaaagaaacggaaacggtgtggtacttgt
gagccctgccggcggctggaaaactgtggcgcttgcactagctgtaccaac
cgccgcacgcaccagatctgcaaactgcgaaaatgtgaggtgctgaagaaa
aaagtagggcttctcaaggaggtggaaataaaggctggtgaaggagccggg
ccgtggggacaaggagcggctgtcaagacaggctcagagctcagcccagtt
gatggacctgttccaggtcagatggactcagggccagtgtaccatggggac
tcacggcagctaagcgcctcaggggtgccggtcaatggtgctagagagccc
gctggacccagtctgctgggggactgggggtccttggcgggtagaccaaaag
cccgactgggaggctgccccaggcccagctcatactgctcgcctggaagat
gcccacgatctggtggccttttcggctgtggccgaagctgtgtcctcttat
ggggcccttagcacccggctctatgaaaccttcaaccgtgagatgagtcgt
gaggctgggaacaacagcaggggacccggccagggcctgagggctgctct
gctggcagcgaagaccttgacacactgcagacggccctggccctcgcgcgg
catggtatgaaaccacccaactgcaactgcgatggcccagaatgccctgac
tacctcgagtggctggaggggaagatcaagtctgtggtcatggaaggaggg
gaggagcggcccaggctcccagggcctctgcctcctggtgaggccggcctc
ccagcaccaagcaccaggccactcctcagctcagaggtgccccagatctct
ccccaagagggcctgcccctgtcccagagtgccctgagcattgccaaggaa
aaaaacatcagcttgcagaccgccattgccattgaggccctcacacagctc
tcctctgccctcccgcagccttctcattccacccccaggcttcttgcccc
cttcctgaggccttgtcacctcctgcccctttcagatctccccagtcttac
ctccgggctccctcatggcctgtggttcctcctgaagagcactcatctttt
gctcctgatagctctgccttccctccagcaactcctagaactgagttccct
gaagcctggggcactgacacccctccagcaacgccccggagctcctggccc
atgcctcgcccaagcccccgatcccatggctgaactggagcagttgttgggc
agcgccagtgattacatccagtcagtattcaagcggcctgaggccctgcct
accaagcccaaggtcaaggtggaggcaccctcttcctccccggccccggcc
ccatccctgtacttcagagggaggctcccacgccatcctcggagcccgac
acccaccagaaggcccagaccgccctgcagcagcacctccaccacaagcgc
agcctcttcctagaacaggtgcacgacacctccttccctgctccttcagag
ccttctgctcctggctggtggcccccaccaagttcacctgtcccacggctt
ccagacagaccacccaaggagaagaagaagaagctcccaacaccagctgga
```

-continued ggtcccgtgggaacggagaaagctgccctgggatcaagcccagtgtccga aagcccattcagatcaagaagtccaggccccgggaagcacagcccctcttc ccacctgtccgacagattgtcctggaagggcttaggtccccagcctcccag gaagtgcaggctcatccaccggcccctctgcctgcctcacagggctctgct gtgcccctgccccagaaccttctcttgcgctatttgcacctagtccctcc agggacagcctgctgcccctactcaggaaatgaggtcccccagccccatg acagccttgcagccaggctccactggccctcttcccctgccgatgacaag ctggaagagctcatccggcagtttgaggctgaatttggagatagctttggg cttcccggcccccttctgtgcccattcaggaccccgagaaccagcaaaca tgtctcccagccctgagagcccctttgctacccgttcccccaagcaaatc aagattgagtcttcggggctgtgactgtgctctcaaccacctgcttccat tcagaggagggaggacaggaggccacacccaccaaggctgagaacccactc acacccaccctcagtggcttcttggagtcacctcttaagtacctggacaca cccaccaagagtctgctggacacacctgccaagagagcccaggccgagttc cccacctgcgattgcgtcgaacaaatagtggagaaagatgaaggtccatat tatactcacttgggatctggccccacggtcgcctctatccgggaactcatg gaggagcggtatggagagaaggggaaagccatccggatcgagaaggtcatc tacacgggggaaggaggggaaagagctcccgcggttgccccattgcaaagtgg gtgatccgcaggcacacgctggaggagaagctactctgcctggtgcggcac cgggcaggccaccactgccagaacgctgtgatcgtcatcctcatcctggcc tgggagggcattccccgtagcctcggagacaccctctaccaggagctcacc gacaccctccggaagtatgggaaccccaccagccggagatgcggcctcaac gatgaccggacctgcgcttgccaaggcaaagaccccaacacctgtggtgcc tccttctcctttggttgttcctggagcatgtacttcaacggctgcaagtat gctcggagcaagacacctcgcaagttccgcctcgcaggggacaatcccaaa gaggaagaagtgctccggaagagtttccaggacctggccaccgaagtcgct cccctgtacaagcgactggcccctcaggcctatcagaaccaggtgaccaac gaggaaatagcgattgactgccgtctggggctgaaggaaggacggcccttc gcggggggtcacggcctgcatggacttctgtgcccacgcccacaaggaccag cataacctctacaatgggtgcaccgtggtctgcaccctgaccaaggaagac aatcgctgcgtgggcaagattcccgaggatgagcagctgcatgttctcccc ctgtacaagatggccaacacggatgagtttggtagcgaggagaaccagaat gcaaaggtgggcagcggagccatccaggtgctcaccgccttcccccgcgag gtccgacgcctgcccgagcctgccaagtcctgccgccagcggcagctggaa gccagaaaggcagcagccgagaagaagaagattcagaaggagaagctgagc actccggagaagatcaagcaggaggccctggagctggcgggcattacgtcg gacccaggcctgtctctgaagggtggattgtcccagcaaggcctgaagccc tccctcaaggtggagccgcagaaccacttcagctccttcaagtacagcggc aacgcggtggtggagagctactcggtgctgggcaactgccggccctccgac ccttacagcatgaacagcgtgtactcctaccactcctactatgcacagccc -continued agcctgacctccgtcaatggcttccactccaagtacgctctcccgtctttt agctactatggcttttccatccagcaacccgtcttcccctctcagttcctg ggtcctggtgcctgggggcatagtggcagcagtggcagttttgagaagaag ccagacctccacgctctgcacaacagcctgagcccggcctacggtggtgct gagtttgccgagctgcccagccaggctgttcccacagacgcccaccacccc actcctcaccaccagcagcctgcgtacccaggccccaaggagtatctgctt cccaaggcccccctactccactcagtgtccagggacccctcccccttttgcc cagagctccaactgctacaacagatccatcaagcaagagccagtagacccg ctgacccaggctgagcctgtgcccagagacgctggcaagatgggcaagaca cctctgtccgaggtgtctcagaatggaggacccagtcacctttggggacag tactcaggagcccaagcatgtccccaagaggactaacggtgtgggtggc agctggggtgtgttctcgtctggggagagtcctgccatcgtccctgacaag ctcagttcctttggggccagctgcctggccccttcccacttcacagatggc cagtggggggctgttccccggtgaggggcagcaggcagcttcccactctgga ggacggctgcgaggcaaaccgtggagcccctgcaagtttgggaacagcacc tcggccttggctgggcccagcctgactgagaagccgtgggcgctgggggca ggggatttcaactcggccctgaaaggtagtcctgggttccaagacaagctg tggaaccccatgaaaggagaggaggggcaggattccagccgcaggggccagc cagctggacagggcctggcagtccttttggtctgcccctgggatccagcgag aagctgtttggggctctgaagtcagaggagaagctgtgggacccccttcagc ctggaggaggggccggctgaggagccccccagcaagggagcggtgaaggag gagaagggcggtggtggtgcggaggaggaagaggaggagctgtggtcggac agtgaacacaacttcctggacgagaacatcggcggcgtggccgtggcccca gcccacggctccatcctcatcgagtgtgcccggcgggagctgcacgccacc acgccgcttaagaagcccaaccgctgccaccccacccgcatctcgctggtc ttctaccagcacaagaacctcaaccagcccaaccacgggctggccctctgg gaagccaagatgaagcagctggcggagagggcacgggcacggcaggaggag gctgcccggctgggcctgggccagcaggaggccaagctctacgggaagaag cgcaagtggggggggcactgtggttgctgagccccagcagaaagagaagaag ggggtcgtccccacccggcaggcactggctgtgcccacagactcggcggtc accgtgtcctcctatgcctacacgaaggtcactggcccctacagccgctgg atctagtctaga SEQ ID NO:12 encodes the open reading frame:

```
                                      (SEQ ID NO: 13)
MDYKDDDDKLDGGYPYDVPDYAGGLDSQFQVPLAVQPDLPGLYDFPQRQVM

VGSFPGSGLSMAGSESQLRGGGDGRKKRKRCGTCEPCRRLENCGACTSCTN

RRTHQICKLRKCEVLKKKVGLLKEVEIKAGEGAGPWGQGAAVKTGSELSPV

DGPVPGQMDSGPVYHGDSRQLSASGVPVNGAREPAGPSLLGTGGPWRVDQK

PDWEAAPGPAHTARLEDAHDLVAFSAVAEAVSSYGALSTRLYETFNREMSR

EAGNNSRGPRPGPEGCSAGSEDLDTLQTALALARHGMKPPNCNCDGPECPD
```

-continued

```
YLEWLEGKIKSVVMEGGEERPRLPGPLPPGEAGLPAPSTRPLLSSEVPQIS

PQEGLPLSQSALSIAKEKNISLQTAIAIEALTQLSSALPQPSHSTPQASCP

LPEALSPPAPFRSPQSYLRAPSWPVVPPEEHSSFAPDSSAFPPATPRTEFP

EAWGTDTPPATPRSSWPMPRPSPDPMAELEQLLGSASDYIQSVFKRPEALP

TKPKVKVEAPSSSPAPAPSPVLQREAPTPSSEPDTHQKAQTALQQHLHHKR

SLFLEQVHDTSFPAPSEPSAPGWWPPPSSPVPRLPDRPPKEKKKKLPTPAG

GPVGTEKAAPGIKPSVRKPIQIKKSRPREAQPLFPPVRQIVLEGLRSPASQ

EVQAHPPAPLPASQGSAVPLPPEPSLALFAPSPSRDSLLPPTQEMRSPSPM

TALQPGSTGPLPPADDKLEELIRQFEAEFGDSFGLPGPPSVPIQDPENQQT

CLPAPESPFATRSPKQIKIESSGAVTVLSTTCFHSEEGGQEATPTKAENPL

TPTLSGFLESPLKYLDTPTKSLLDTPAKRAQAEFPTCDCVEQIVEKDEGPY

YTHLGSGPTVASIRELMEERYGEKGKAIRIEKVIYTGKEGKSSRGCPIAKW

VIRRHTLEEKLLCLVRHRAGHHCQNAVIVILILAWEGIPRSLGDTLYQELT

DTLRKYGNPTSRRCGLNDDRTCACQGKDPNTCGASFSFGCSWSMYFNGCKY

ARSKTPRKFRLAGDNPKEEEVLRKSFQDLATEVAPLYKRLAPQAYQNQVTN

EEIAIDCRLGLKEGRPFAGVTACMDFCAHAHKDQHNLYNGCTVVCTLTKED

NRCVGKIPEDEQLHVLPLYKMANTDEFGSEENQNAKVGSGAIQVLTAFPRE

VRRLPEPAKSCRQRQLEARKAAAEKKKIQKEKLSTPEKIKQEALELAGITS

DPGLSLKGGLSQQGLKPSLKVEPQNHFSSFKYSGNAVVESYSVLGNCRPSD

PYSMNSVYSYHSYYAQPSLTSVNGFHSKYALPSFSYYGFPSSNPVFPSQFL

GPGAWGHSGSSGSFEKKPDLHALHNSLSPAYGGAEFAELPSQAVPTDAHHP

TPHHQQPAYPGPKEYLLPKAPLLHSVSRDPSPFAQSSNCYNRSIKQEPVDP

LTQAEPVPRDAGKMGKTPLSEVSQNGGPSHLWGQYSGGPSMSPKRTNGVGG

SWGVFSSGESPAIVPDKLSSFGASCLAPSHFTDGQWGLFPGEGQQAASHSG

GRLRGKPWSPCKFGNSTSALAGPSLTEKPWALGAGDFNSALKGSPGFQDKL

WNPMKGEEGRIPAAGASQLDRAWQSFGLPLGSSEKLFGALKSEEKLWDPFS

LEEGPAEEPPSKGAVKEEKGGGGAEEEEEELWSDSEHNFLDENIGGVAVAP

AHGSILIECARRELHATTPLKKPNRCHPTRISLVFYQHKNLNQPNHGLALW

EAKMKQLAERARARQEEAARLGLGQQEAKLYGKKRKWGGTVVAEPQQKEKK

GVVPTRQALAVPTDSAVTVSSYAYTKVTGPYSRWI
```

Embryo Development Assessments.

Fertilized embryos were cultured in HECM-9 media (Arthur Chang & Chan, *Methods Mol Biol,* 770, 337-363, doi: 10.1007/978-1-61779-210-6_13 (2011)) and were monitored daily until Day 7-8 when blastocysts were formed. To minimize the exposure of fluorescent light that might affect emrbyo development, selected embryos were used for fluorescent imaging. Embryo development rates were calculated based on fertilized embryos that had achieved the first division, 4-8 cells, 16 cells, morula, compacted morula, blastocyst, and expanded blastocyst stages.

Intracytoplasmic Spermatid Injection (ICSI) of Spermatids, Sperm Extract and Tet3 into Mature Rhesus Macaque Oocyte.

Sperm extract and Tet3 protein can be mixed while spermatids are prepared in a separate microdrop in a petri-dish covered with sterile mineral oil. MII mature rhesus oocytes can be placed in a separate drop on the same petri-dish. For ICSI, a micropipette mounted onto a micro-manipulator and connected with a microinjector can be used to aspirate spermatids followed by the aspiration of Tet3 and sperm extract. The mixture of spermatids, Tet3 and sperm extract can then be injected into the cytoplasm of each oocyte. Following ICSI, oocytes can be activated by cultur-ing five minutes in 5 µM ionomycin in TALP-Hepes medium, followed by incubation in 2 mM 6-Dimethylami-nopurine (6-DMAP) in HECM-9 for five hours in a humidi-fied atmosphere of 5% $CO_2$, 5% $O_2$ and 90% $N_2$ at 37° C.

In-Vitro Culture of NHP Embryo.

Oocytes are washed in equilibrated TALP and returned to culture in 100 µl HECM-9, monkey embryo culture medium, under oil. Fertilization is assessed within 3-6 h by detection of the second polar body using Hoffmann Modulation Con-trast optics. The number of pronuclei is assessed between 12-16 h post injection. After completion of the second cleavage division, 4-8 cell embryos are co-cultured in HECM-9+10% FCS.

Preparation of Monkey Sperm Extract.

1. Ejaculated sperm is washed with TH3 medium by centrifugation at 1500 rpm for 5 min. The supernatant is aspirated out the supernatant and the sperm concen-tration adjusted to 5-10×10^8 sperm/mL.
2. Sperm layer is then be pelleted and washed three times with modified intracellular buffer (ICB) by centrifuga-tion at 1,400 rpm (Eppendorf benchtop centrifuge) for 5 min at RT.
3. This is followed by Lysing by four freeze-thaw cycles.
4. The lysed samples are then be spin at 100,000×g (e.g. 48,000 rpm of Beckman micro-ultracentrifuge) for 1 hour at 4 C.
5. The supernatant is transferred to new clean Eppendorf tube, and kept on ice.
6. It is then concentrated (~3-5 folds) by using centrocon-30 microfiltration membrane (Amicon Cat #4208) and centrifugation at 3000×g for 20 min.
7. Aliquoted 10 uL per vial and stored at −80° C.

ICB buffer (pH 7.5) is shown in Table 2 (above).

Results

Most of the embryos arrested at the 8-16 cell stage when the embryonic genome engages. TET3 expression (ten-eleven translocation 3) was examined. TET3 is an enzyme responsible for DNA demethylation, which is an important step in early fertilization (Guo et al., *Cell Stem Cell* 15, 447-459, doi: 10.1016/j.stem.2014.08.003 (2014), Navara et al., *Stem Cells* 25, 2695-2704, doi:2007-0286 [pii] 10.1634/ stemcells.2007-0286 (2007)).

Experiments were designed to determine if Tet3 is respon-sible for prompt erasure of methylated marks shortly after injection of the spermatids. Like endogenous round sper-matids, and unlike mature sperm, in vitro-derived rSLCs show reduced TET3 expression (FIG. 4A). Addition of purified TET3 protein and trichostatin A (TSA) at the time of rSLC injection resulted in improved fertilization rates, higher quality of embryos based on improved embryo mor-phology (i.e. low fragmentation), and improved develop-ment rates (e.g., elevated blastocyst rates) compared to TET3 cDNA+TSA, TET3 cDNA+mRNA+TSA, or oocyte activation alone (FIG. 4B-4H).

Figure 4H:
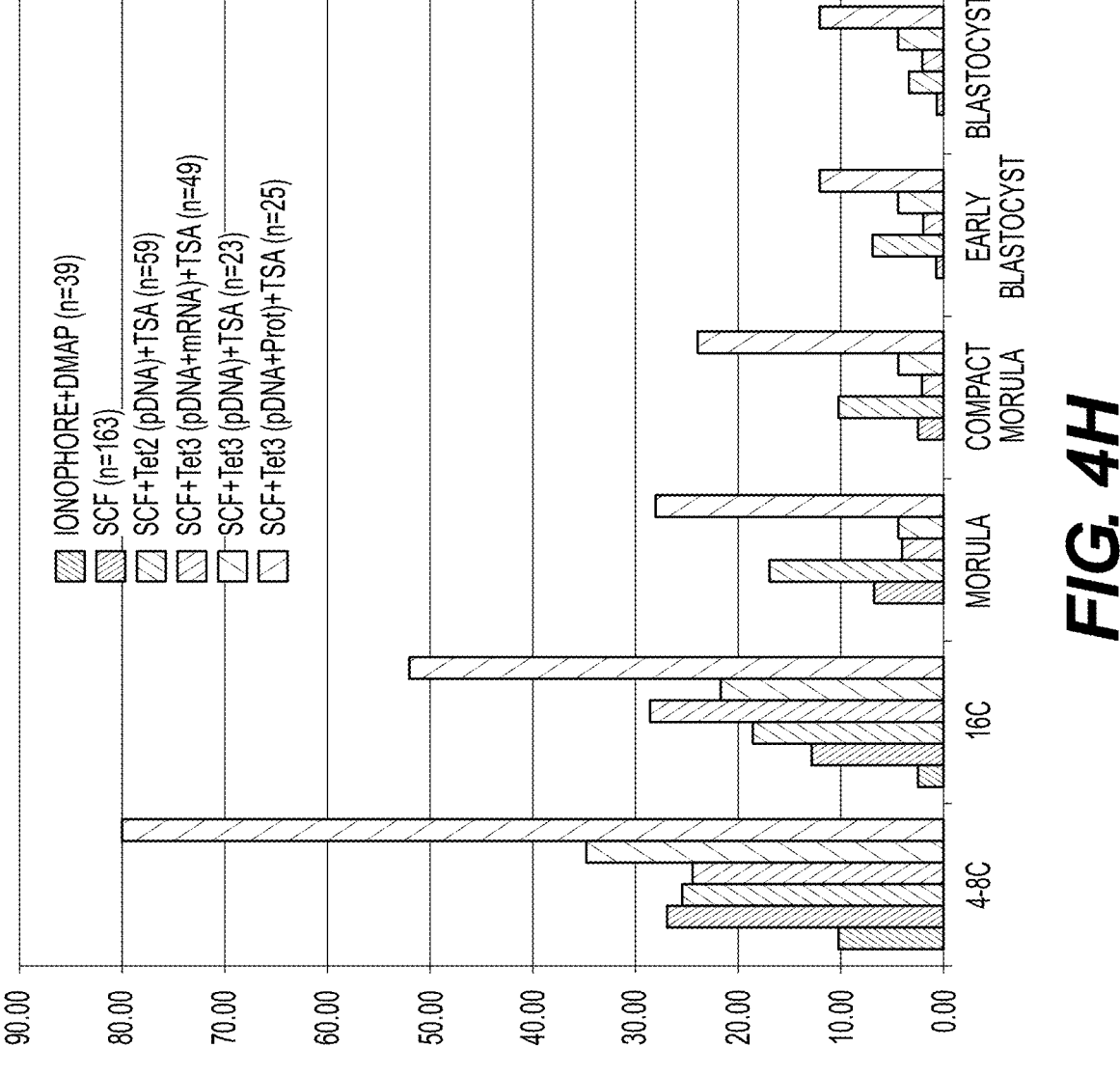
FIG. 4H is a bar graph showing the effect of various factors on in vitro procreated embryo development. Each cluster of bars (e.g., 4-8 cell, 16 cell, morula, compact morula, early blastocyst, blastocyst) represents, from left-to-right: ionophore+DMAP, SCF, SCF+Tet2 (pDNA)+TSA, SCF+Tet3 (pDNA+mRNA)+TSA, SCF+Tet3 (pDNA)+TSA, and SCF+Tet3 (pDNA+Protein)+TSA.

Co-injection of sperm extract and in vitro derived sper-matids with Tet3 plasmid DNA (Tet3-pDNA), Tet3 mRNA, or Tet3 protein indicated the importance on timing of Tet3 activity or paternal demethylation during ZGA and subsequent EGA events (FIGS. 4A-4H). Compared to injecting sperm extract alone, co-injection of Tet3-pDNA improved cleavage rate while co-injection with Tet3-mRNA further improve development up to 8 cell stage with development to 16 cell stage and morula at low rate. Co-injection with Tet3 protein significantly improved cleavage rate with majority of embryo develop beyond 8-cell stage and close to 12% reached to blastocyst stage (FIG. 4H).

In addition, morphology and development rate of preimplantation embryos in Tet3 protein group was comparable to normal embryos fertilized with ejaculated spermatozoa, while high level of fragmentation was observed in all other treatment groups which indicates abnormal development in such embryos (see, e.g., Stone et al., *Am J Obstet Gynecol.*, 192(6):2014-9 (2005)). Although fragmentation is commonly seen in natural conception, the degree of fragmentation was also used as guideline for determining embryo quality and predictor of pregnancy (Stone et al., 2005).

These experiments are believed to represent the first report to generate functional male gametes from non-human primate pluripotent stem cells. While complete in vitro spermatogenesis resulting in mature spermatozoa has not been accomplished in any species, these results are the first to show that functional haploid spermatids can be generated completely in vitro. Spermatids derived from the protocol are immature and not capable of activating oocytes on their own. However, the addition of activation factors coupled with TET3 augmentation (e.g., purified TET3 protein) increased the efficiency of generating healthy embryos. These results support feasibility of regenerative medicine-based therapies whereby patient-specific pluripotent stem cells are differentiated into functional gametes for patients unable to produce their own gametes, particularly where such gametes are needed for managing their infertility through ART.

Example 3: CRISPR/Cas9 Efficiently and Specifically Modifies a Target Gene in Pre-Implantation Embryos In Vitro

Materials and Methods

Gene targeting will be achieved in pluripotent stem cells or skin fibroblast followed by reprogramming to pluripotent state or induced pluripotent stem cells (iPSCs). In brief, gRNA that target a specific target gene will be transfected into aforementioned cell types either in the form of RNA or plasmid DNA that express the gRNA. Cas9 mRNA or protein or expression vector that express Cas9 will be co-transfected with gRNA into aforementioned cell types. Successful targeting will be confirmed in clonal cell line by sequencing and identified for in vitro production of haploid spermatids for fertilization. To further confirm on- and off-target effect, whole genome sequencing can be performed on the selected cell lines prior to the derivation of haploid spermatids for fertilization, embryo production or production of offspring.

Intracytoplasmic Spermatid Injection (ICSI) of Spermatids, Sperm Extract and Tet3 into Mature Rhesus Macaque Oocyte:

Sperm extract and Tet3 protein will be mixed while spermatids will be prepared in a separate microdrop in a petri-dish covered with sterile mineral oil. MII mature rhesus oocytes will be placed in a separate drop on the same petri-dish. For ICSI, a micropipette mounted onto a micro-manipulator and connected with a microinjector will be used to aspirate spermatids followed by the aspiration of Tet3 and sperm extract. The mixture of spermatids, Tet3 and sperm extract will then be injected into the cytoplasm of each oocyte. Following ICSI, oocytes will then be activated by culturing five minutes in 5 M ionomycin in TALP-Hepes medium, followed by incubation in 2 mM 6-Dimethylaminopurine (6-DMAP) in HECM-9 for five hours in a humidified atmosphere of 5% $CO_2$, 5% $O_2$ and 90% $N_2$ at 37° C.

In-Vitro Culture of NHP Embryo:

Oocytes are washed in equilibrated TALP and returned to culture in 100 µl HECM-9, monkey embryo culture medium, under oil. Fertilization is assessed within 3-6 h by detection of the second polar body using Hoffmann Modulation Contrast optics. The number of pronuclei is assessed between 12-16 h post injection. After completion of the second cleavage division, 4-8 cell embryos are co-cultured in HECM-9+10% FCS (Hyclone Laboratories, Inc., Logan, UT).

Results

All gene targeted embryos generated from gene targeted pluripotent stem cells derived spermatids are expected to carry the same genetic modification. If the gene target is genetic mutation linked to inherited genetic disease such as Huntington's disease, genetically corrected embryos can be generated with no off-target effect.

There are currently no cures for Autistic Spectrum Disorders (ASD), and treatments are only available for particular symptoms pertaining to a child's development. It is a devastating disorder that has significant social and economic impact as the number of children affected increases. An estimated lifetime cost for an individual with an ASD is $3.2 million, which is largely attributable to loss of productivity and the cost of adult care. The diagnosis of ASD is primarily based on deficits in all of the following: reciprocal social interaction, communication and stereotyped behaviors. In populations of diagnosed children, 15-70% exhibit intellectual impairments. The fundamental diagnosis for ASD is homogeneous, based on the criteria listed above; however, ASD can also co-exist in patients with syndromes such as Fragile X or neurofibromatosis.

Genetic studies of ASD have yielded an intriguing list of select genomic targets with several of the genes directly linked to the regulation of critical synaptic functions, including FMR1, MECP2, PTEN, UBE3A, NLGN1-NLGN4, NRXN1 and SHANK3. Moreover, some of the candidates, such as SHANK3, are associated to ASD in a gene-dosage-dependent manner. SHANK3, a gene integral to the glutamatergic pathway, is a binding partner for the neuroligins NLGN3 and NLGN4, which themselves bind neurexins, all of which are genetically associated with ASD progression. Additionally, mutations in genes downstream of SHANK3 signaling, such as DIAPH3, have also been linked to ASD. Consequently, disruption of SHANK3-mediated glutamatergic transmission appears to play a pivotal role in ASD pathogenesis. Moreover, the chromosomal location of SHANK3 at 22q13 is linked to considerable human pathology due to genetic deletions which result in SHANK3 haploinsufficiency and strong phenotypes of developmental and language delays. Because of the dose dependent nature (or haploinsufficiency) of SHANK3, it is an ideal target to test CRISPR/Cas as means for inducing genetic changes in pre-implantation embryos.

Figures 5B, 5C:
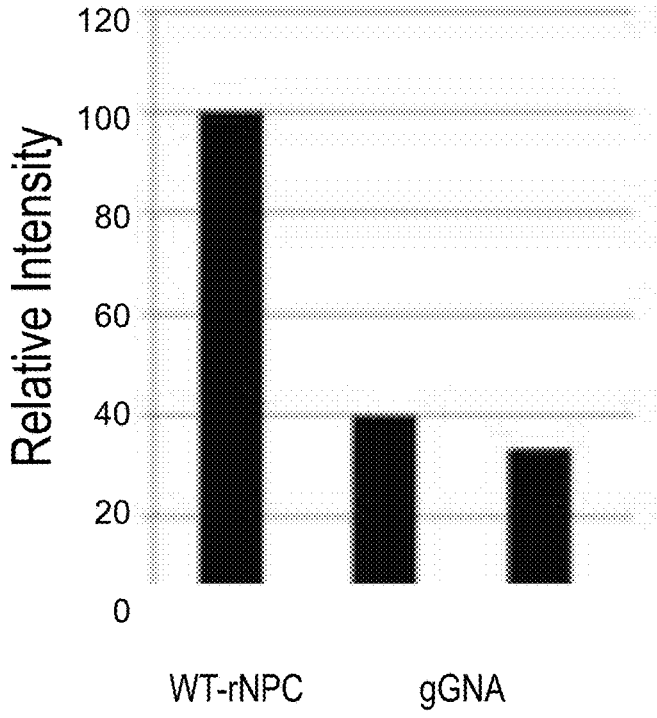
FIG. 5B is a bar graph illustrating the results of Western blot analysis of SHANK3 protein.
FIG. 5C is an illustration of the sequence of mutant cells showing deletion at the target site (SEQ ID NO:8) relative to wildtype (SEQ ID NO:7).

First, an in vitro approach was used to evaluate targeting efficiency and specificity of the SHANK3-gRNA/Cas9 systems in rhesus neural progenitor cells (NPCs). The SHANK3-gRNA-Cas9 plasmid (FIG. 5A) was transfected into NPCs and was recovered at 72 hours post-transfection for western blot (FIG. 5B) and sequence analyses (FIG. 5C). SHANK3-gRNA can effectively reduce the expression of SHANK3 in rhesus NPCs with at least 60% reduction to close to 70% loss of SHANK3 protein which was determined by using SHANK3 specific antibody in western blot analysis. This result indicates the SHANK3 gene was successfully targeted by SHANK3-gRNA, and SHANK3 protein was significantly reduced.

Figures 6A, 6B:
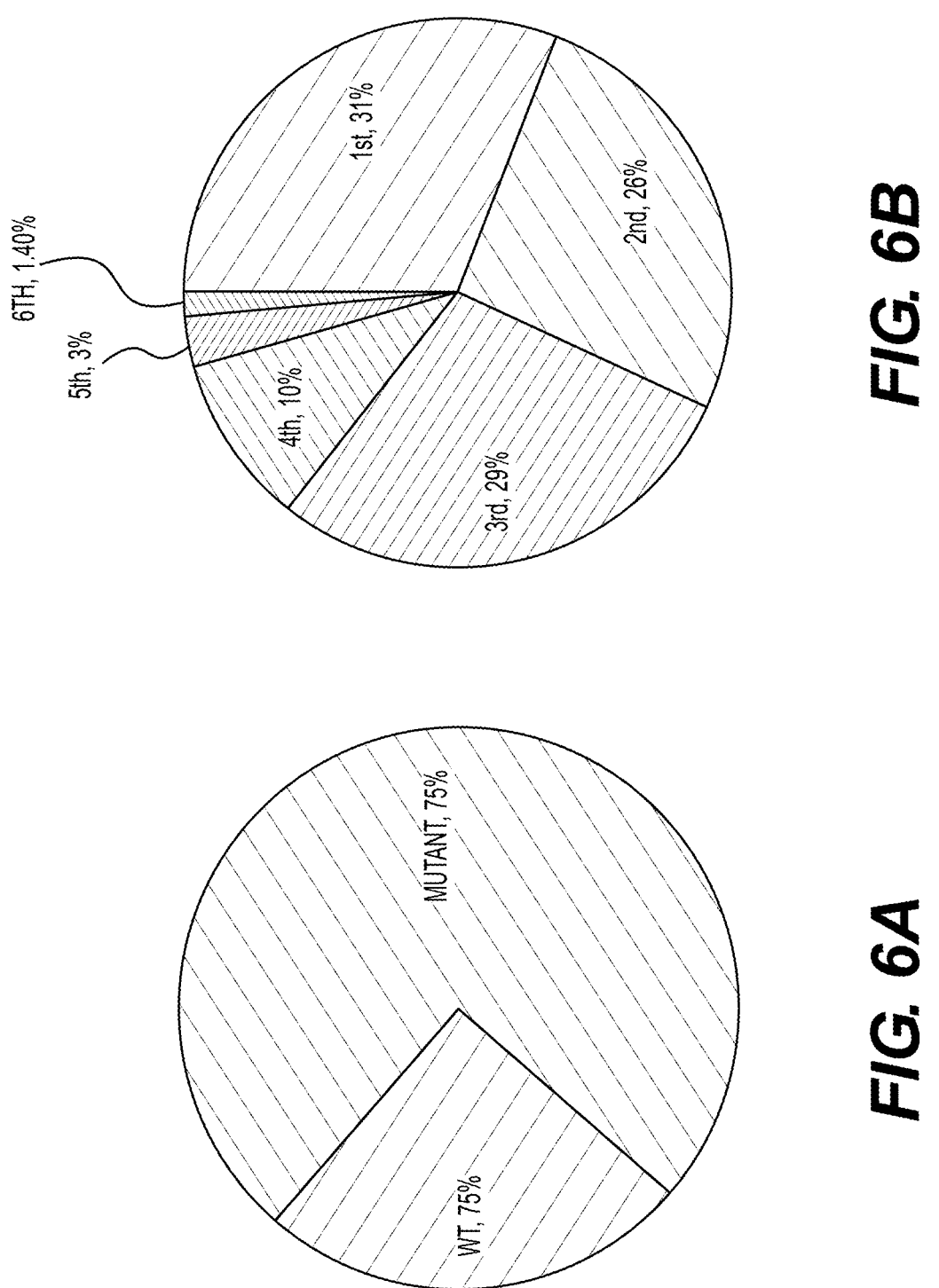
FIGS. 6A and 6B are pie charts showing sequencing analysis of gene targeted embryo and estimated timing of mutation at 1st to 6th cell division after fertilization.

To evaluate targeting efficiency of SHANK3-gRNA in rhesus macaque pre-implantation embryos, rhesus one-cell embryos (zygotes) were co-injected with both SHANK3-gRNA and Cas9 mRNA into the cytoplasm followed by in vitro culture. A total of 96 pre-implantation embryos were analyzed for indel mutations by Genescan analysis. Earlier embryos (1-2 cell stages) were analyzed up to later stages (blastocyst) to determine gene targeting rate and time (FIG. 6A-6B). Among a total of 96 embryos screened, 72 embryos had a mutation (75%) (FIG. 6A).

CRISP-ID and TIDE were used to decompose the sequencing data and delineate the timing of when mutation might have occurred. The timing of the mutation was deduced based on the percentage of the WT-allele in the sequencing data: 0-50% ($1^{st}$ cell division), 51-75% ($2^{nd}$ cell division), 76-87.5% ($3^{rd}$ cell division), 88.5-93.75% ($4^{th}$ cell division), 94.75-96.875% ($5^{th}$ cell division), and >97.875%

($6^{th}$ cell division). Among 72 embryos with mutant allele, 31% had mutation occurring at the $1^{st}$ cell division, 26% at the $2^{nd}$ cell division, 29% at the $3^{rd}$ cell division, 10% at the $4^{th}$ cell division, 3% at the $5^{th}$ cell division and 1.4% at the $6^{th}$ cell division or later (FIG. 6B).

Figure 7:
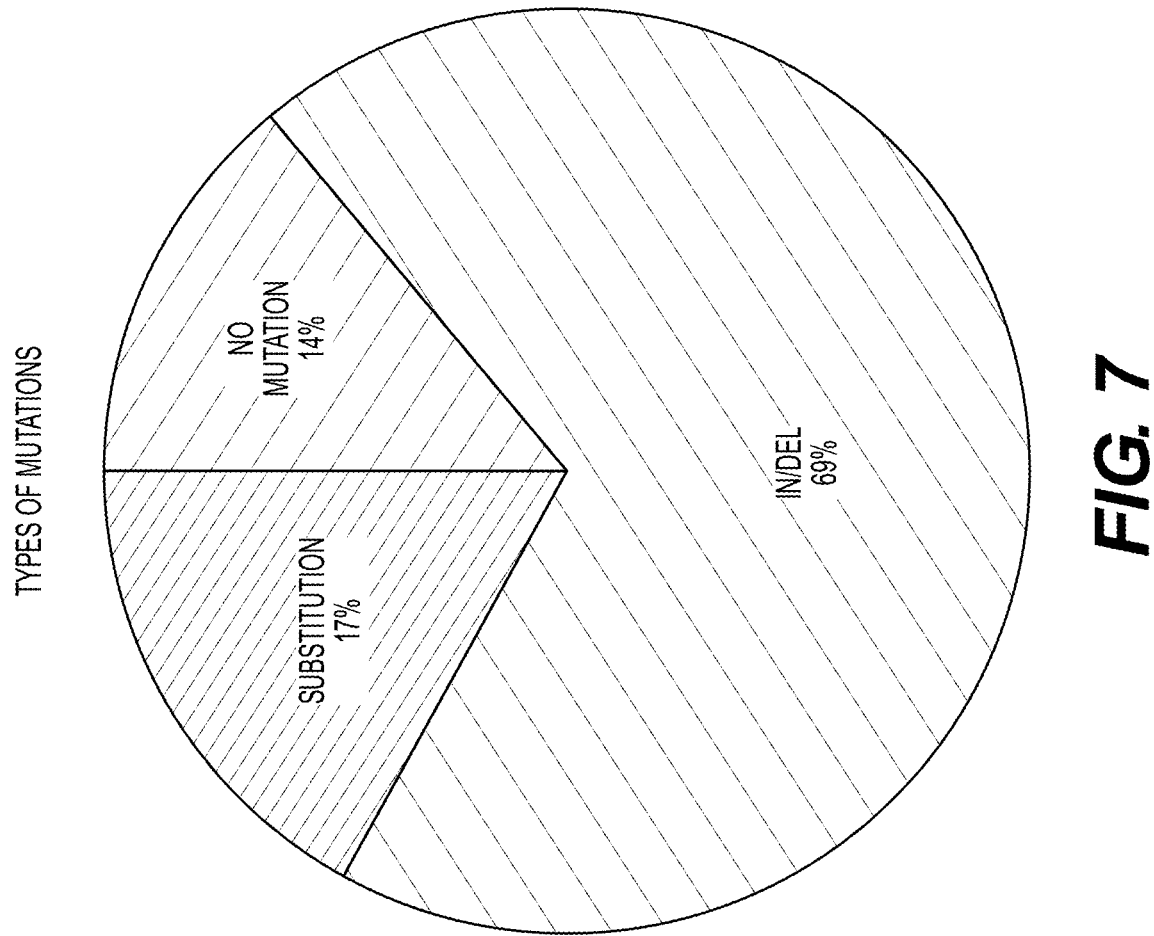
FIG. 7 is a pie chart showing the break down of types of mutations (substitutions, insertion/deletions, or no mutation) that occurred by SHANK3 CRISPR-Cas9-mediated gene editing. n=96.

As CRISPR-Cas9 induces double strand break (DSB), the main mode of mutation is through non-homologous end joining (NHEJ). NHEJ typically introduces insertions/deletions (InDels) to the sequences. The most common mutation was In/Dels (69%) (FIG. 7). Also, imperfect repair can introduce base-pair substitutions, and 17% substitutions were found in this data (FIG. 7).

Collectively, these results show that that SHANK3 can be successfully targeted in rhesus embryo using CRISPR/Cas9 efficiently and with no significant impact on early embryo development compared to WT-embryo control.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

---

We claim:

1. A method of improving embryo development comprising administering a compound that increases bioavailability of a TET protein into (i) an oocyte or a male gamete and contacting the oocyte and male gamete to form a fertilized embryo, or (ii) a fertilized embryo formed by contacting an oocyte and a male gamete, in an effective amount to improve development of the fertilized embryo.

2. The method of claim 1, wherein the compound is administered into the oocyte before, during, or after fertilization.

3. The method of claim 1, wherein the compound is administered by injection.

4. The method of claim 1, wherein the compound is administered by intracytoplasmic injection.

5. The method of claim 4, wherein the compound and the male gamete are administered in combination into the oocyte by intracytoplasmic sperm injection (ICSI).

6. The method of claim 1, wherein the TET protein is TET1, TET2, TET3, or a combination thereof.

7. The method of claim 1, wherein the compound is a small molecule, a TET polypeptide or protein, a fusion protein including a TET polypeptide or protein, an isolated nucleic acid encoding a TET polypeptide or protein or TET fusion protein, or an agent that increases endogenous expression of a TET polypeptide or protein.

8. The method of claim 7, wherein the compound increases bioavailability of TET3.

9. The method of claim 8, wherein the compound is a TET3 polypeptide or protein, a fusion protein including a TET3 polypeptide or protein, an isolated nucleic acid encoding a TET3 polypeptide or protein or TET3 fusion protein, or an agent that increases endogenous expression of a TET3 polypeptide or protein.

10. The method of claim 9, wherein the TET3 polypeptide or protein is full-length TET3.

11. The method of claim 9, wherein the TET3 polypeptide or protein is human TET3 or a variant thereof comprising at least 85% sequence identity to human TET3.

12. The method of claim 1, wherein the male gamete is a round spermatid, an elongating spermatid, a condensing spermatid, or a condensed spermatid.

13. The method of claim 1, wherein the male gamete is prepared by differentiating an embryonic stem cell, an induced pluripotent stem cell, or a spermatogonia stem cell.

14. The method of claim 1, further comprising administering into the oocyte, the male gamete, or the fertilized embryo an effective amount of a gene editing composition,
    wherein the oocyte, the male gamete, or the fertilized embryo comprises a gene mutation or anomaly in the genome thereof, and
    wherein the gene editing composition corrects the gene mutation or anomaly.

15. The method of claim 1, wherein the male gamete is prepared by a method of differentiating a cell selected from the group consisting of an embryonic stem cell, an induced pluripotent stem cell, and a spermatogonia stem cell into a round spermatid, an elongating spermatid, a condensing spermatid, or a condensed spermatid.

16. The method of claim 15, wherein the method of differentiating a cell does not include feeder cells.

17. The method of claim 1, further comprising administering into the oocyte, male gamete, or fertilized embryo a sperm extract.

18. The method of claim 1, further comprising administering into the oocyte, male gamete, or fertilized embryo trichostatin A (TSA).

19. A composition comprising a male gamete and a compound that increases bioavailability of a TET protein to improve development of a subsequent embryo resulting from fertilization of an oocyte by the male gamete.

20. The composition of claim 19, further comprising trichostatin A (TSA).

* * * * *

SEQUENCE LISTING

```
Sequence total quantity: 15
SEQ ID NO: 1            moltype = AA  length = 1660
FEATURE                Location/Qualifiers
source                 1..1660
                       mol_type = protein
                       organism = Homo sapiens
SEQUENCE: 1
MDSGPVYHGD SRQLSASGVP VNGAREPAGP SLLGTGGPWR VDQKPDWEAA PGPAHTARLE   60
DAHDLVAFSA VAEAVSSYGA LSTRLYETFN REMSREAGNN SRGPRPGPEG CSAGSEDLDT  120
LQTALALARH GMKPPNCNCD GPECPDYLEW LEGKIKSVVM EGGEERPRLP GPLPPGEAGL  180
PAPSTRPLLS SEVPQISPQE GLPLSQSALS IAKEKNISLQ TAIAIEALTQ LSSALPQPSH  240
STPQASCPLP EALSPPAPFR SPQSYLRAPS WPVVPPEEHS SFAPDSSAFP PATPRTEFPE  300
AWGTDTPPAT PRSSWPMPRP SPDPMAELEQ LLGGSASDYIQ SVFKRPEALP TKPKVKVEAP  360
SSSPAPAPSP VLQREAPTPS SEPDTHQKAQ TALQQHLHHK RSLFLEQVHD TSFPAPSEPS  420
APGWWPPPSS PVPRLPDRPP KEKKKKLPTP AGGPVGTEKA APGIKPSVRK PIQIKKSRPR  480
EAQPLFPPVR QIVLEGLRSP ASQEVQAHPP APLPASQGSA VPLPPEPSLA LFAPSPSRDS  540
LLPPTQEMRS PSPMTALQPG STGPLPPADD KLEELIRQFE AEFGDSFGLP GPPSVPIQDP  600
ENQQTCLPAP ESPFATRSPK QIKIESSGAV TVLSTTCFHS EEGGQEATPT KAENPLTPTL  660
SGFLESPLKY LDTPTKSLLD TPAKRAQAEF PTCDCVEQIV EKDEGPYYTH LGSGPTVASI  720
RELMEERYGE KGKAIRIEKV IYTGKEGKSS RGCPIAKWVI RRHTLEEKLL CLVRHRAGHH  780
CQNAVIVILI LAWEGIPRSL GDTLYQELTD TLRKYGNPTS RRCGLNDDRT CACQGKDPNT  840
CGASFSFGCS WSMYFNGCKY ARSKTPRKFR LAGDNPKEEE VLRKSFQDLA TEVAPLYKRL  900
APQAYQNQVT NEEIAIDCRL GLKEGRPFAG VTACMDFCAH AHKDQHNLYN GCTVVCTLTK  960
EDNRCVGKIP EDEQLHVLPL YKMANTDEFG SEENQNAKVG SGAIQVLTAF PREVRRLPEP 1020
AKSCRQRQLE ARKAAAEKKK IQKEKLSTPE KIKQEALELA GITSDPGLSL KGGLSQQGLK 1080
PSLKVEPQNH FSSFKYSGNA VVESYSVLGN CRPSDPYSMN SVYSYHSYYA QPSLTSVNGF 1140
HSKYALPSFS YYGFPSSNPV FPSQFLGPGA WGHSGSSGSF EKKPDLHALH NSLSPAYGGA 1200
EFAELPSQAV PTDAHHPTPH HQQPAYPGPK EYLLPKAPLL HSVSRDPSPF AQSSNCYNRS 1260
IKQEPVDPLT QAEPVPRDAG KMGKTPLSEV SQNGGPSHLW GQYSGGPSMS PKRTNGVGGS 1320
WGVFSSGESP AIVPDKLSSF GASCLAPSHF TDGQWGLFPG EGQQAASHSG GRLRGKPWSP 1380
CKFGNSTSAL AGPSLTEKPW ALGAGDFNSA LKGSPGFQDK LWNPMKGEEG RIPAAGASQL 1440
DRAWQSFGLP LGSSEKLFGA LKSEEKLWDP FSLEEGPAEE PPSKGAVKEE KGGGGAEEEE 1500
EELWSDSEHN FLDENIGGVA VAPAHGSILI ECARRELHAT TPLKKPNRCH PTRISLVFYQ 1560
HKNLNQPNHG LALWEAKMKQ LAERARARQE EAARLGLGQQ EAKLYGKKRK WGGTVVAEPQ 1620
QKEKKGVVPT RQALAVPTDS AVTVSSYAYT KVTGPYSRWI                      1660

SEQ ID NO: 2            moltype = DNA  length = 5388
FEATURE                Location/Qualifiers
source                 1..5388
                       mol_type = unassigned DNA
                       organism = Homo sapiens
SEQUENCE: 2
atgagccagt ttcaggtgcc cctggccgtc cagccggacc tgccaggcct ttatgacttc   60
cctcagcgcc aggtgatggt agggagcttc ccggggtctg ggctctccat ggctgggagt  120
```

```
gagtcccaac tccgagggggg tggagatggt cgaaagaaac ggaaacggtg tggtacttgt    180
gagccctgcc ggcggctgga aaactgtggc gcttgcacta gctgtaccaa ccgccgcacg    240
caccagatct gcaaactgcg aaaatgtgag gtgctgaaga aaaaagtagg gcttctcaag    300
gaggtggaaa taaaggctgg tgaaggagcc gggccgtggg gacaaggagc ggctgtcaag    360
acaggctcag agctcagccc agttgatgga cctgttccag gtcagatgga ctcagggcca    420
gtgtaccatg gggactcacg gcagctaagc gcctcagggg tgccggtcaa tggtgctaga    480
gagcccgctg gacccagtct gctgggggact ggggtcctt ggcgggtaga ccaaaagccc    540
gactgggagg ctgccccagg cccagctcat actgctcgcc tggaagatgc ccacgatctg    600
gtggcctttt cggctgtggc cgaagctgtg tcctcttatg gggccccttag cacccggctc    660
tatgaaacct tcaaccgtga gatgagtcgt gaggctggga acaacagcag gggaccccgg    720
ccagggcctg agggctgctc tgctggcagc gaagaccttg acacactgca gacggccctg    780
gccctcgcgc ggcatggtat gaaaccaccc aactgcaact gcgatggccc agaatgccct    840
gactacctcg agtggctgga gggaagatc aagtctgtgg tcatggaagg aggggaggag    900
cggcccaggc tcccagggcc tctgcctcct ggtgaggccg gcctcccagc accaagcacc    960
aggccactcc tcagctcaga ggtgcccag atctctcccc aagagggcct gccctgtcc    1020
cagagtgccc tgagcattgc caaggaaaaa aacatcagct tgcagaccgc cattgccatt    1080
gaggccctca cacagctctc ctctgccctc ccgcagcctt ctcattccac cccccaggct    1140
tcttgcccc ttcctgaggc cttgtcacct cctgcccctt tcagatctcc ccagtcttac    1200
ctccggggctc cctcatggcc tgtggttcct cctgaagagc actcatcttt tgctcctgat    1260
agctctgcct tccctccagc aactcctaga actgagttcc ctgaagcctg gggcactgac    1320
accccctccag caacgccccg gagctcctgg cccatgcctc gcccaagccc cgatcccatg    1380
gctgaactgg agcagttgtt gggcagcgcc agtgattaca tccagtcagt attcaagcgg    1440
cctgaggccc tgcctaccaa gcccaaggtc aaggtggagg caccctcttc ctcccccggcc    1500
ccggccccat cccctgtact tcagagggag gctcccacgc catcctcgga gcccgacacc    1560
caccagaagg cccagaccgc cctgcagcag cacctccacc acaagcgcag cctcttccta    1620
gaacaggtgc acgacacctc cttccctgct ccttcagagc cttctgctcc tggctggtgg    1680
ccccaccaa gttcacctgt cccacggctt ccagacagac cacccaagga gaagaagaag    1740
aagctcccaa caccagctgg aggtcccgtg ggaacggaga aagctgcccc tgggatcaag    1800
cccagtgtcc gaaagcccat tcagatcaag aagtccaggc cccgggaagc acagcccctc    1860
ttcccacctg tccgacagat tgtcctggaa gggcttaggt cccagctcct ccaggaagtg    1920
caggctcatc caccggcccc tctgcctgcc tcacagggct ctgctgtgcc cctgccccca    1980
gaaccttctc ttgcgctatt tgcacctagt ccctccaggg acagcctgct gcccctact    2040
caggaaatga ggtcccccag ccccatgaca gccttgcagc caggctccac tggccctctt    2100
ccccctgccg atgacaagct ggaagagctc atccggcagt ttgaggctga atttggagat    2160
agctttgggc ttcccggccc cccttctgtg cccattcagg accccgagaa ccagcaaaca    2220
tgtctcccag cccctgagag ccccctttgct acccgttccc ccaagcaaat caagattgag    2280
tcttcgggggg ctgtgactgt gctctcaacc acctgcttcc attcagagga gggaggacag    2340
gaggccacac ccaccaaggc tgagaaccca ctcacaccca ccctcagtgg cttcttggag    2400
tcacctctta agtacctgga cacacccacc aagagtctgc tggacacacc tgccaagaga    2460
gcccaggccg agttccccac ctgcgattgc gtcgaacaaa tagtggagaa agatgaaggt    2520
ccatattata ctcacttggg atctggcccc acggtcgcct ctatccggga actcatggag    2580
gagcggtatg gagagaaggg gaaagccatc cggatcgaga aggtcatcta cacggggaag    2640
gagggaaaga gctcccgcgg ttgcccccatt gcaaagtggg tatccgcag gcacacgctg    2700
gaggagaagc tactctgcct ggtgcggcac cgggcaggcc accactgcca gaacgctgtg    2760
atcgtcatcc tcatcctggc ctgggagggc attccccgta gcctcggaga caccctctac    2820
caggagctca ccgacaccct ccggaagtat gggaaccccca ccagccggag atgcggcctc    2880
aacgatgacc ggacctgcgc ttgccaaggc aaagacccaa acacctgtgg tgcctccttc    2940
tcctttggtt gttcctggag catgtacttc aacggctgca agtatgctcg gagcaagaca    3000
cctcgcaagt tccgcctcgc aggggacaat cccaaagagg aagaagtgct ccggaagagt    3060
ttccaggacc tggccaccga agtcgctccc ctgtacaagc gactggcccc tcaggcctat    3120
cagaaccagg tgaccaacga ggaaatagcg attgactgcc gtctgggggct gaaggaagga    3180
cggcccttcg cgggggtcac ggcctgcatg gacttctgtg cccacgccca caaggaccag    3240
cataacctct acaatgggtg caccgtggtc tgcaccctga ccaaggaaga caatcgctgc    3300
gtgggcaaga ttcccgagga tgagcagctg catgttctcc ccctgtacaa gatggccaac    3360
acggatgagt ttggtagcga ggagaaccag aatgcaaagg tgggcagcgg agccatccag    3420
gtgctcaccg ccttccccccg cgaggtccga cgcctgcccg agcctgccaa gtcctgccgc    3480
cagcggcagc tggaagccag aaaaggcagca gccgagaaga agaagattca gaaggagaag    3540
ctgagcactc cggagaagat caagcaggag gccctggagc tggcgggcat tacgtcggac    3600
ccaggcctgt ctctgaaggg tggattgtcc cagcaaggcc tgaagccctc cctcaaggtg    3660
gagccgcaga accacttcag ctccttcaag tacagcgaca acggtggt ggagagctac    3720
tcggtgctgg gcaactgccg gccctccgac ccttacagca tgaacagcgt gtactcctac    3780
cactcctact atgcacagcc cagcctgacc tccgtcaatg gcttccactc caagtacgct    3840
ctcccgtctt ttagctacta tggctttcca tccagcaacc ccgtcttccc ctctcagttc    3900
ctgggtctgc gtgcctgggg gcacagtggc agcagtgcc gttttgagaa gaagccagac    3960
ctccacgctc tgcacaacag cctgagcccg gcctacggtg gtgctgagtt tgccgagctg    4020
cccagccagg ctgttcccac agacgcccac caccccactc ctcaccacca gcagcctgcg    4080
tacccaggcc ccaaggagta tctgcttccc aaggcccccc tactccactc agtgtccagg    4140
gacccctccc cctttgccca gagctccaac tgctacaaca gatccatcaa gcaagagcca    4200
gtagaccccgc tgaccaggcc tgagcctgtg cccagagacg ctggcaagat gggcaagaca    4260
cctctgtccg aggtgtctca gaatggagga cccagtcacc tttggggaca gtactcagga    4320
ggcccaagca tgtccccccaa gaggactaac ggtgtgggtg gcagctgggg tgtgttctcg    4380
tctggggaga gtcctgccat cgtccctgac aagctcagtt cctttgggggc cagctgcctg    4440
gccccttccc acttcacaga tggccagtgg gggctgttcc ccggtgaggg gcagcaggca    4500
gcttcccact ctggaggacg gctgcgaggc aaaccgtgca gccctgcaa gtttgggaac    4560
agcacctccg cctttggctgg gcccagcctg actgagaagc cgtgggcgct ggggggcaggg    4620
gatttcaact cggccctgaa aggtagtcct gggttccaag acaagctgtg gaaccccatg    4680
aaaggagagg agggcaggat tccagccgca ggggccagcc agctggacag ggcctggcag    4740
tcctttggtc tgccctgggg atccagcgag aagctgtttg gggctctgaa gtcagaggag    4800
aagctgtggg accccttcag cctggaggag gggccggctg aggagccccc cagcaaggga    4860
```

-continued

```
gcggtgaagg aggagaaggg cggtggtggt gcggaggagg aagaggagga gctgtggtcg    4920
gacagtgaac acaacttcct ggacgagaac atcggcggcg tggccgtggc cccagcccac    4980
ggctccatcc tcatcgagtg tgcccggcgg gagctgcacg ccaccacgcc gcttaagaag    5040
cccaaccgct gccacccac ccgcatctcg ctggtcttct accagcacaa gaacctcaac     5100
cagcccaacc acgggctggc cctctgggaa gccaagatga agcagctggc ggagagggca    5160
cgggcacggc aggaggaggc tgcccggctg ggcctgggcc agcaggaggc caagctctac    5220
gggaagaagc gcaagtgggg gggcactgtg gttgctgagc cccagcagaa agagaagaag    5280
ggggtcgtcc ccaccggca ggcactggct gtgcccacag actcggcggt caccgtgtcc     5340
tcctatgcct acacgaaggt cactggcccc tacagccgct ggatctag               5388
```

```
SEQ ID NO: 3               moltype = AA   length = 136
FEATURE                    Location/Qualifiers
REGION                     1..136
                           note = synthetic polypeptide
source                     1..136
                           mol_type = protein
                           organism = synthetic construct
SEQUENCE: 3
MSQFQVPLAV QPDLPGLYDF PQRQVMVGSF PGSGLSMAGS ESQLRGGGDG RKKRKRCGTC   60
EPCRRLENCG ACTSCTNRRT HQICKLRKCE VLKKKVGLLK EVEIKAGEGA GPWGQGAAVK   120
TGSELSPVDG PVPGQM                                                   136
```

```
SEQ ID NO: 4               moltype = DNA   length = 24
FEATURE                    Location/Qualifiers
misc_feature               1..24
                           note = synthetic polynucleotide
source                     1..24
                           mol_type = other DNA
                           organism = synthetic construct
SEQUENCE: 4
cctgcagaaa cgggaccacg aggg                                          24
```

```
SEQ ID NO: 5               moltype = DNA   length = 24
FEATURE                    Location/Qualifiers
misc_feature               1..24
                           note = synthetic polynucleotide
source                     1..24
                           mol_type = other DNA
                           organism = synthetic construct
SEQUENCE: 5
cctgcagaaa cgggaccatg aggg                                          24
```

```
SEQ ID NO: 6               moltype = DNA   length = 23
FEATURE                    Location/Qualifiers
misc_feature               1..23
                           note = synthetic polynucleotide
variation                  21
                           note = n is a, c, g, or t
source                     1..23
                           mol_type = other DNA
                           organism = synthetic construct
SEQUENCE: 6
gctgcagaaa cgggaccacg ngg                                           23
```

```
SEQ ID NO: 7               moltype = DNA   length = 35
FEATURE                    Location/Qualifiers
misc_feature               1..35
                           note = synthetic polynucleotide
source                     1..35
                           mol_type = other DNA
                           organism = synthetic construct
SEQUENCE: 7
cctgcagaaa cgggaccatg agggctttgg ttttg                              35
```

```
SEQ ID NO: 8               moltype = DNA   length = 29
FEATURE                    Location/Qualifiers
misc_feature               1..29
                           note = synthetic polynucleotide
source                     1..29
                           mol_type = other DNA
                           organism = synthetic construct
SEQUENCE: 8
cctgcagaaa cgggaccatt ttggttttg                                     29
```

```
SEQ ID NO: 9               moltype = AA   length = 2002
FEATURE                    Location/Qualifiers
source                     1..2002
                           mol_type = protein
                           organism = Homo sapiens
```

```
SEQUENCE: 9
MEQDRTNHVE GNRLSPFLIP SPPICQTEPL ATKLQNGSPL PERAHPEVNG DTKWHSFKSY   60
YGIPCMKGSQ NSRVSPDFTQ ESRGYSKCLQ NGGIKRTVSE PSLSGLLQIK KLKQDQKANG  120
ERRNFGVSQE RNPGESSQPN VSDLSDKKES VSSVAQENAV KDFTSFSTHN CSGPENPELQ  180
ILNEQEGKSA NYHDKNIVLL KNKAVLMPNG ATVSASSVEH THGELLEKTL SQYYPDCVSI  240
AVQKTTSHIN AINSQATNEL SCEITHPSHT SGQINSAQTS NSELPPKPAA VVSEACDADD  300
ADNASKLAAM LNTCSFQKPE QLQQQKSVFE ICPSPAENNI QGTTKLASGE EFCSGSSSNL  360
QAPGGSSERY LKQNEMNGAY FKQSSVFTKD SFSATTTPPP PSQLLLSPPP PLPQVPQLPS  420
EGKSTLNGGV LEEHHHYPNQ SNTTLLREVK IEGKPEAPPS QSPNPSTHVC SPSPMLSERP  480
QNNCVNRNDI QTAGTMTVPL CSEKTRPMSE HLKHNPPIFG SSGELQDNCQ QLMRNKEQEI  540
LKGRDKEQTR DLVPPTQHYL KPGWIELKAP RFHQAESHLK RNEASLPSIL QYQPNLSNQM  600
TSKQYTGNSN MPGGLPRQAY TQKTTQLEHK SQMYQVEMNQ GQSQGTVDQH LQFQKPSHQV  660
HFSKTDHLPK AHVQSLCGTR FHFQQRADSQ TEKLMSPVLK QHLNQQASET EPFSNSHLLQ  720
HKPHKQAAQT QPSQSSHLPQ NQQQQQKLQI KNKEEILQTF PHPQSNNDQQ REGSFFGQTK  780
VEECFHGENQ YSKSSEFETH NVQMGLEEVQ NINRRNSPYS QTMKSSACKI QVSCSNNTHL  840
VSENKEQTTH PELFAGNKTQ NLHHMQYFPN NVIPKQDLLH RCFQEQEQKS QQASVLQGYK  900
NRNQDMSGQQ AAQLAQQRYL IHNHANVFPV PDQGGSHTQT PPQKDTQKHA ALRWHLLQKQ  960
EQQQTQQPQT ESCHSQMHRP IKVEPGCKPH ACMHTAPPEN KTWKKVTKQE NPPASCDNVQ 1020
QKSIIETMEQ HLKQFHAKSL FDHKALTLKS QKQVKVEMSG PVTVLTRQTT AAELDSHTPA 1080
LEQQTTSSEK TPTKRTAASV LNNFIESPSK LLDTPIKNLL DTPVKTQYDF PSCRCVEQII 1140
EKDEGPFYTH LGAGPNVAAI REIMEERFGQ KGKAIRIERV IYTGKEGKSS QGCPIAKWVV 1200
RRSSSEEKLL CLVRERAGHT CEAAVIVILI LVWEGIPLSL ADKLYSELTE TLRKYGTLTN 1260
RRCALNEERT CACQGLDPET CGASFSFGCS WSMYYNGCKF ARSKIPRKFK LLGDDPKEEE 1320
KLESHLQNLS TLMAPTYKKL APDAYNNQIE YEHRAPECRL GLKEGRPFSG VTACLDFCAH 1380
AHRDLHNMQN GSTLVCTLTR EDNREFGGKP EDEQLHVLPL YKVSDVDEFG SVEAQEEKKR 1440
SGAIQVLSSF RRKVRMLAEP VKTCRQRKLE AKKAAAEKLS SLENSSNKNE KEKSAPSRTK 1500
QTENASQAKQ LAELLRLSGP VMQQSQQPQP LQKQPPQPQQ QQRPQQQQPH HPQTESVNSY 1560
SASGSTNPYM RRPNPVSPYP NSSHTSDIYG STSPMNFYST SSQAAGSYLN SSNPMNPYPG 1620
LLNQNTQYPS YQCNGNLSVD NCSPYLGSYS PQSQPMDLYR YPSQDPLSKL SLPPIHTLYQ 1680
PRFGNSQSFT SKYLGYGNQN MQGDGFSSCT IRPNVHHVGK LPPYPTHEMD GHFMGATSRL 1740
PPNLSNPNMD YKNGEHHSPS HIIHNYSAAP GMFNSSLHAL HLQNKENDML SHTANGLSKM 1800
LPALNHDRTA CVQGGLHKLS DANGQEKQPL ALVQGVASGA EDNDEVWSDS EQSFLDPDIG 1860
GVAVAPTHGS ILIECAKREL HATTPLKNPN RNHPTRISLV FYQHKSMNEP KHGLALWEAK 1920
MAEKAREKEE ECEKYGPDYV PQKSHGKKVK REPAEPHETS EPTYLRFIKS LAERTMSVTT 1980
DSTVTTSPYA FTRVTGPYNR YI                                          2002

SEQ ID NO: 10           moltype = AA   length = 2136
FEATURE                 Location/Qualifiers
source                  1..2136
                        mol_type = protein
                        organism = Homo sapiens
SEQUENCE: 10
MSRSRHARPS RLVRKEDVNK KKKNSQLRKT TKGANKNVAS VKTLSPGKLK QLIQERDVKK   60
KTEPKPPVPV RSLLTRAGAA RMNLDRTEVL FQNPESLTCN GFTMALRSTS LSRRLSQPPL  120
VVAKSKKVPL SKGLEKQHDC DYKILPALGV KHSENDSVPM QDTQVLPDIE TLIGVQNPSL  180
LKGKSQETTQ FWSQRVEDSK INIPTHSGPA AEILPGPLEG TRCGEGLFSE ETLNDTSGSP  240
KMFAQDTVCA PFPQRATPKV TSQGNPSIQL EELGSRVESL KLSDSYLDPI KSEHDCYPTS  300
SLNKVIPDLN LRNCLALGGS TSPTSVIKFL LAGSKQATLG AKPDHQEAFE ATANQQEVSD  360
TTSFLGQAFG AIPHQWELPG ADPVHGEALG ETPDLPEIPG AIPVQGEVFG TILDQQETLG  420
MSGSVVPDLP VFLPVPPNPI ATFNAPSKWP EPQSTVSYGL AVQGAIQILP LGSGHTPQSS  480
SNSEKNSLPP VMAISNVENE KQVHISFLPA NTQGFPLAPE RGLFHASLGI AQLSQAGPSK  540
SDRGSSQVSV TSTVHVVNTT VVTMPVPMVS TSSSSYTTLL PTLEKKKRKR CGVCEPCQQK  600
TNCGECTYCK NRKNSHQICK KRKCEELKKK PSVVVPLEVI KENKRPQREK KPKVLKADFD  660
NKPVNGPKSE SMDYSRCGHG EEQKLELNPH TVENVTKNED SMTGIEVEKW TQNKKSQLTD  720
HVKGDFSANV PEAEKSKNSE VDKKRTKSPK LFVQTVRNGI KHVHCLPAET NVSFKKFNIE  780
EFGKTLENNS YKFLKDTANH KNAMSSVATD MSCDHLKGRS NVLVFQQPGF NCSSIPHSSH  840
SIINHHASIH NEGDQPKTPE NIPSKEPKDG SPVQPSLLSL MKDRRLTLEQ VVAIEALTQL  900
SEAPSENSSP SKSEKDEESE QRTASLLNSC KAILYTVRKD LQDPNLQGEP PKLNHCPSLE  960
KQSSCNTVVF NGQTTTLSNS HINSATNQAS TKSHEYSKVT NSLSLFIPKS NSSKIDTNKS 1020
IAQGIITLDN CSNDLHQLPP RNNEVEYCNQ LLDSSKKLDS DDLSCQDATH TQIEEDVATQ 1080
LTQLASIIKI NYIKPEDKKV ESTPTSLVTC NVQQKYNQEK GTIQQKPPSS VHNNHGSSLT 1140
KQKNPTQKKT KSTPSRDRRK KKPTVVSYQE NDRQKWEKLS YMYGTICDIW IASKFQNFGQ 1200
FCPHDFPTVF GKISSSTKIW KPLAQTRSIM QPKTVFPPLT QIKLQRYPES AEEKVKVEPL 1260
DSLSLFHLKT ESNGKAFTDK AYNSQVQLTV NANQKAHPLT QPSSPPNQCA NVMAGDDQIR 1320
FQQVVKEQLM HQRLPTLPGI SHETPLPESA LTLRNVNVVC SGGITVVSTK SEEEVCSSSF 1380
GTSEFSTVDS AQKNFNDYAM NFFTNPTKNL VSITKDSELP TCSCLDRVIQ KDKGPYYTHL 1440
GAGPSVAAVR EIMENRYGQK GNAIRIEIVV YTGKEGKSSH GCPIAKWVLR RSSDEEKVLC 1500
LVRQRTGHHC PTAVMVVLIM VWDGIPLPMA DRLYTELTEN LKSYNGHPTD RRCTLNENRT 1560
CTCQGIDPET CGASFSFGCS WSMYFNGCKF GRSPSPRRFR IDPSSPLHEK NLEDNLQSLA 1620
TRLAPIYKQY APVAYQNQVE YENVARECRL GSKEGRPFSG VTACLDFCAH PHRDIHNMNN 1680
GSTVVCTLTR EDNRSLGVIP QDEQLHVLPL YKLSDTDEFG SKEGMEAKIK SGAIEVLAPR 1740
RKKRTCFTQP VPRSGKKRAA MMTEVLAHKI RAVEKKPIPR IKRKNNSTTT NNSKPSSLPT 1800
LGSNTETVQP EVKSETEPHF ILKSSDNTKT YSLMPSAPHP VKEASPGFSW SPKTASATPA 1860
PLKNDATASC GFSERSSTPH CTMPSGRLSG ANAAAADGPG ISQLGEVAPL PTLSAPVMEP 1920
LINSEPSTGV TEPLTPHQPN HQPSFLTSPQ DLASSPMEED EQHSEADEPP SDEPLSDDPL 1980
SPAEEKLPHI DEYWSDSEHI FLDANIGGVA IAPAHGSVLI ECARRELHAT TPVEHPNRNH 2040
PTRLSLVFYQ HKNLNKPQHG FELNKIKFEA KEAKNKKMKA SEQKDQAANE GPEQSSEVNE 2100
LNQIPSHKAL TLTHDNVVTV SPYALTHVAG PYNHWV                           2136
```

-continued

```
SEQ ID NO: 11          moltype =   length =
SEQUENCE: 11
000

SEQ ID NO: 12          moltype = DNA   length = 5469
FEATURE                Location/Qualifiers
misc_feature           1..5469
                       note = synthetic polynucleotide
source                 1..5469
                       mol_type = other DNA
                       organism = synthetic construct
SEQUENCE: 12
atggactaca aggacgacga tgacaagctc gatggaggat accccctacga cgtgcccgac  60
tacgccggag gactcgacag ccagtttcag gtgcccctgg ccgtccagcc ggacctgcca  120
ggcctttatg acttccctca gcgccaggtg atggtaggga gcttcccggg gtctgggctc  180
tccatggctg ggagtgagtc ccaactccga gggggtggga tggtcgaaa gaaacggaaa  240
cggtgtggta cttgtgagcc ctgccggcgg ctggaaaact gtggcgcttg cactagctgt  300
accaaccgcc gcacgcacca gatctgcaaa ctgcgaaaat gtgaggtgct gaagaaaaaa  360
gtagggcttc tcaaggaggt ggaaataaag gctggtgaag gagccgggcc gtggggacaa  420
ggagcggctg tcaagacagg ctcagagctc agcccagttg atggacctgt tccaggtcag  480
atggactcag ggccagtgta ccatggggac tcacggcagc taagcgcctc aggggtgccg  540
gtcaatggtg ctagagagcc cgctggaccc agtctgctgg ggactggggg tccttggcgg  600
gtagaccaaa agcccgactg ggaggctgcc ccaggcccag ctcatactgc tcgcctggaa  660
gatgcccacg atctggtggc cttttcggct gtggccgaag ctgtgtcctc ttatggggcc  720
cttagcaccc ggctctatga aaccttcaac cgtgagatga gtcgtgaggc tgggaacaac  780
agcaggggac cccggccagg gcctgagggc tgctctgctg gcagcgaaga ccttgacaca  840
ctgcagacgg ccctgccct cgcgcggcat ggtatgaaac cacccaactg caactgcgat  900
ggcccagaat gccctgacta cctcgagtgg ctggagggga agatcaagtc tgtggtcatg  960
gaaggagggg aggagcggcc caggctccca gggcctctgc ctcctggtga ggccggcctc  1020
ccagcaccaa gcaccaggcc actcctcagc tcagaggtgc cccagatctc tccccaagag  1080
ggcctgcccc tgtcccagag tgccctgagc attgccaagg aaaaaaacat cagcttgcag  1140
accgccattg ccattgaggc cctcacacag ctctcctctg ccctcccgca gccttctcat  1200
tccaccccc aggcttcttg ccccccttcct gaggccttgt cacctcctgc cccttttcaga  1260
tctccccagt cttacctccg ggctccctca tggcctgtgg ttcctcctga agagcactca  1320
tcttttgctc ctgatagctc tgccttccct ccagcaactc ctagaactga gttccctgaa  1380
gcctggggca ctgacacccc tccagcaacg ccccggagct cctggcccat gcctcgccca  1440
agccccgatc ccatggctga actggagcag ttgttgggca gcgccagtga ttacatccag  1500
tcagtattca agcggcctga ggccctgcct accaagccca aggtcaaggt ggaggcaccc  1560
tcttcctccc cggccccggc cccatccect gtacttcaga gggaggctcc cacgccatcc  1620
tcggagcccg acacccacca gaaggcccag accgccctgc agcagcacct ccaccacaag  1680
cgcagcctct tcctagaaca ggtgcacgac acctccttcc ctgctccttc agagccttct  1740
gctcctggct ggtggccccc accaagttca cctgtcccac ggcttccaga cagaccaccc  1800
aaggagaaga agaagaagct cccaacacca gctggaggtc ccgtgggaac ggagaaagct  1860
gcccctggga tcaagcccag tgtccgaaag cccattcaga tcaagaagtc caggcccccg  1920
gaagcacagc ccctcttccc acctgtccga cagattgtcc tggaagggct taggtcccca  1980
gcctcccagg aagtgcaggc tcatccaccg gcccctctgc ctgcctcaca gggctctgct  2040
gtgccctgc cccagaacc ttctcttgcg ctatttgcac ctagtccctc cagggacagc  2100
ctgctgcccc ctactcagga aatgaggtcc cccagcccca tgacagcctt gcagccaggc  2160
tccactggcc ctcttcccc tgccgatgac aagctggaag agctcatccg gcagtttgag  2220
gctgaatttg gagatagctt tgggcttccc ggcccccctt ctgtgcccat tcaggacccc  2280
gagaaccagc aaacatgtct cccagcccct gagagcccct ttgctacccg ttccccaag  2340
caaatcaaga ttgagtcttc gggggctgtg actgtgctct caaccacctg cttccattca  2400
gaggagggag gacaggaggc cacacccacc aaggctgaga acccactcac acccaccctc  2460
agtggcttct tggagtcacc tcttaagtac ctggacacac ccaccaagag tctgctggac  2520
acacctgcca agagagccca ggccgagttc cccacctgcg attgcgtcga acaaatagtg  2580
gagaaagatg aaggtccata ttatactcac ttgggatctg gccccacggt cgcctctatc  2640
cgggaactca tggaggagcg gtatggagag aaggggaaag ccatccggat cgagaaggtc  2700
atctacacgg ggaaggaggg aaagagctcc cgcggttgcc ccattgcaaa gtgggtgatc  2760
cgcaggcaca cgctggagga gaagctactc tgctccggtg gcggcacgggc aggccaccac  2820
tgccagaacg ctgtgatcgt catcctcatc ctggcctgga agggcattcc ccgtagcctc  2880
ggagacaccc tctaccagga gctcaccgac accctccgga agtatgggaa ccccaccagc  2940
cggagatgcg gcctcaacga tgaccggacc tgcgcttgcc aaggcaaaga ccccaacacc  3000
tgtggtgcct ccttctcctt tggttgttcc tggagcatgt acttcaacgg ctgcaagtat  3060
gctcggagca agacacctcg caagttccgc ctcgcaggga acaatcccaa agaggaagaa  3120
gtgctccgga gagtttcca ggacctggcc accgaagtcg ctccctgta caagcgactg  3180
gccctcagg cctatcagaa ccaggtgacc aacgaggaaa tagcgattga ctgccgtctg  3240
gggctgaagg aaggacggcc cttcgcgggg gtcacggcct gcatggactt ctgtgcccac  3300
gcccacaagg accagcataa cctctacaat gggtgcaccg tggtctgcac cctgaccaag  3360
gaagacaatc gctgcgtggg caagattccc gaggatggac agctgcatgt tctccccctg  3420
tacaagatgg ccaacacgga tgagtttggt agcgaggaga accagaatgc aaaggtgggc  3480
agcggagcca tccaggtgct caccgccttc ccccgcgagg tccgacgcct gcccgagcct  3540
gccaagtcct gccgccagcg gcagctggaa gccagaaagg cagcagccga gaagaagaag  3600
attcagaagg agaagctgag cactccggag aagatcaagc aggaggccct ggagctggcg  3660
ggcattacgt cggacccagg cctgtctctg aagggtggat tgtccagca aggcctgaag  3720
ccctccctca aggtggagcc gcagaaccac ttcagctcct tcaagtacag cggcaacgcg  3780
gtggtggaga gctactcggt gctgggcaac tgccggcccc ccgacccta cagcatgaac  3840
agcgtgtact cctaccactc ctactatgca cagcccagcc tgacctccgt caatggcttc  3900
cactccaagt acgctctccc gtctttagc tactatggct ttccatccag caaccccgtc  3960
ttcccctctc agttcctggg tcctggtgcc tggggggcata gtggcagcag tggcagtttt  4020
```

```
gagaagaagc cagacctcca cgctctgcac aacagcctga gcccggccta cggtggtgct    4080
gagtttgccg agctgcccag ccaggctgtt cccacagacg cccaccaccc cactcctcac    4140
caccagcagc ctgcgtaccc aggccccaag gagtatctgc ttcccaaggc cccctactc     4200
cactcagtgt ccagggaccc ctcccccttt gcccagagct ccaactgcta caacagatcc    4260
atcaagcaag agccagtaga cccgctgacc caggctgagc ctgtgcccag agacgctggc    4320
aagatgggca agacacctct gtccgaggtg tctcagaatg gaggacccag tcacctttgg    4380
ggacagtact caggaggccc aagcatgtcc cccaagagga ctaacggtgt gggtggcagc    4440
tggggtgtgt tctcgtctgg ggagagtcct gccatcgtcc ctgacaagct cagttccttt    4500
ggggccagct gcctggcccc ttcccacttc acagatggcc agtgggggct gttccccggt    4560
gaggggcagc aggcagcttc ccactctgga ggacggctgc gaggcaaacc gtggagcccc    4620
tgcaagtttg ggaacagcac ctcggccttg gctgggccca gctgactga gaagccgtgg     4680
gcgctggggg caggggattt caactcggcc ctgaaaggta gtcctgggtt ccaagacaag    4740
ctgtggaacc ccatgaaagg agaggagggc aggattccag ccgcagggc cagccagctg     4800
gacagggcct ggcagtcctt tggtctgccc ctgggatcca gcgagaagct gtttgggct     4860
ctgaagtcag aggagaagct gtgggacccc ttcagcctgg aggagggcc ggctgaggag      4920
ccccccagca agggagcggt gaaggaggag aagggcggtg gtggtgcgga ggaggaagag    4980
gaggagcgtg ggtcggacag tgaacacaac ttcctggacg agaacatcgg cggcgtggcc    5040
gtggccccag cccacggctc catcctcatc gagtgtgccc ggcggagctg cacgccacc     5100
acgccgctta agaagcccaa ccgctgccac cccacccgca tctcgctggt cttctaccag    5160
cacaagaacc tcaaccagcc caaccacggg ctggccctct gggaagccaa gatgaagcag    5220
ctggcggaga gggcacgggc acggcaggag gaggctgccc ggctgggcct gggccagcag    5280
gaggccaag tctacgggaa gaagcccaag tgggggggca ctgtggttgc tgagcccag      5340
cagaaagaga agaaggggt cgtccccacc cggcaggcac tggctgtgcc cacagactcg     5400
gcggtcaccg tgtcctccta tgcctacacg aaggtcactg cccctacag ccgctggatc      5460
tagtctaga                                                              5469
```

```
SEQ ID NO: 13              moltype = AA   length = 1820
FEATURE                    Location/Qualifiers
REGION                     1..1820
                           note = synthetic polypeptide
source                     1..1820
                           mol_type = protein
                           organism = synthetic construct
SEQUENCE: 13
MDYKDDDDKL DGGYPYDVPD YAGGLDSQFQ VPLAVQPDLP GLYDFPQRQV MVGSFPGSGL    60
SMAGSESQLR GGGDGRKKRK RCGTCEPCRR LENCGACTSC TNRRTHQICK LRKCEVLKKK    120
VGLLKEVEIK AGEGAGPWGQ GAAVKTGSEL SPVDGPVPGQ MDSGPVYHGD SRQLSASGVP    180
VNGAREPAGP SLLGTGGPWR VDQKPDWEAA PGPAHTARLE DAHDLVAFSA VAEAVSSYGA    240
LSTRLYETFN REMSREAGNN SRGPRPGPEG CSAGSEDLDT LQTALALARH GMKPPNCNCD    300
GPECPDYLEW LEGKIKSVVM EGGEERPRLP GPLPPGEAGL PAPSTRPLLS SEVPQISPQE    360
GLPLSQSALS IAKEKNISLQ TAIAIEALTQ LSSALPQPSH STPQASCPLP EALSPPAPFR    420
SPQSYLRAPS WPVVPPEEHS SFAPDSSAFP PATPRTEFPE AWGTDTPPAT PRSSWPMPRP    480
SPDPMAELEQ LLGSASDYIQ SVFKRPEALP TKPKVKVEAP SSSPAPAPSP VLQREAPTPS    540
SEPDTHQKAQ TALQQHLHHK RSLFLEQVHD TSFPAPSEPS APGWWPPPSS PVPRLPDRPP    600
KEKKKKLPTP AGGPVGTEKA APGIKPSVRK PIQIKKSRPR EAQPLFPPVR QIVLEGLRSP    660
ASQEVQAHPP APLPASQGSA VPLPPEPSLA LFAPSPSRDS LLPPTQEMRS PSPMTALQPG    720
STGPLPPADD KLEELIRQFE AEFGDSFGLP GPPSVPIQDP AQQTCLPAP ESPFATRSPK     780
QIKIESSGAV TVLSTTCFHS EEGGQEATPT KAENPLTPTL SGFLESPLKY LDTPTKSLLD    840
TPAKRAQAEF PTCDCVEQIV EKDEGPYYTH LGSGPTVASI RELMEERYGE KGKAIRIEKV    900
IYTGKEGKSS RGCPIAKWVI RRHTLEEKLL CLVRHRAGHH CQNAVIVILI LAWEGIPRSL    960
GDTLYQELTD TLRKYGNPTS RRCGLNDDRT CACQGKDPNT CGASFSFGCS WSMYFNGCKY    1020
ARSKTPRKFR LAGDNPKEEE VLRKSFQDLA TEVAPLYKRL APQAYQNQVT NEEIAIDCRL    1080
GLKEGRPFAG VTACMDFCAH AHKDQHNLYN GCTVVCTLTK EDNRCVGKIP EDEQLHVLPL    1140
YKMANTDEFG SEENQNAKVG SGAIQVLTAF PREVRRLPEP AKSCRQRQLE ARKAAAEKKK    1200
IQKEKLSTPE KIKQEALELA GITSDPGLSL KGGLSQQGLK PSLKVEPQNH FSSFKYSGNA    1260
VVESYSVLGN CRPSDPYSMN SVYSYHSYYA QPSLTSVNGF HSKYALPSFS YYGFPSSNPV    1320
FPSQFLGPGA WGHSGSSGSF EKKPDLHALH NSLSPAYGGA EFAELPSQAV PTDAHHPTPH    1380
HQQPAYPGPK EYLLPKAPLL HSVSRDPSPF AQSSNCYNRS IKQEPVDPLT QAEPVPRDAG    1440
KMGKTPLSEV SQNGGPSHLW GQYSGGPSMS PKRTNGVGGS WGVFSSGESP AIVPDKLSSF    1500
GASCLAPSHF TDGQWGLFPG EGQQAASHSG GRLRGKPWSP CKFGNSTSAL AGPSLTEKPW    1560
ALGAGDFNSA LKGSPGFQDK LWNPMKGEEG RIPAAGASQL DRAWQSFGLP LGSSEKLFGA    1620
LKSEEKLWDP FSLEEGPAEE PPSKGAVKEE KGGGGAEEEE EELWSDSEHN FLDENIGGVA    1680
VAPAHGSILI ECARRELHAT TPLKKPNRCH PTRISLVFYQ HKNLNQPNHG LALWEAKMKQ    1740
LAERARARQE EAARLGLGQQ EAKLYGKKRK WGGTVVAEPQ QKEKKGVVPT RQALAVPTDS    1800
AVTVSSYAYT KVTGPYSRWI                                                 1820
```

```
SEQ ID NO: 14              moltype = DNA   length = 18
FEATURE                    Location/Qualifiers
misc_feature               1..18
                           note = synthetic polynucleotide
source                     1..18
                           mol_type = other DNA
                           organism = synthetic construct
SEQUENCE: 14
cccaagagg aagaagtg                                                     18
```

```
SEQ ID NO: 15              moltype = DNA   length = 18
FEATURE                    Location/Qualifiers
misc_feature               1..18
```

-continued

```
                    note = synthetic polynucleotide
source              1..18
                    mol_type = other DNA
                    organism = synthetic construct
SEQUENCE: 15
gcagtcaatc gctatttc                                        18
```